United States Patent
Loose et al.

(10) Patent No.: US 10,383,881 B2
(45) Date of Patent: Aug. 20, 2019

(54) 1,5-DIHYDRO-2H-PYRROL-2-ONE COMPOUNDS AND METHODS OF USING SAME

(71) Applicant: Frequency Therapeutics, Inc., Woburn, MA (US)

(72) Inventors: Christopher Loose, Winchester, MA (US); Bradley Tait, Malden, MA (US); Rajesh Manchanda, Acton, MA (US); Will McLean, North Haven, CT (US)

(73) Assignee: Frequency Therapeutics, Inc., Woburn, MA (US)

( * ) Notice: Subject to any disclaimer, the term of this patent is extended or adjusted under 35 U.S.C. 154(b) by 8 days.

(21) Appl. No.: 15/852,889

(22) Filed: Dec. 22, 2017

(65) Prior Publication Data

US 2018/0214458 A1    Aug. 2, 2018

Related U.S. Application Data

(60) Provisional application No. 62/441,063, filed on Dec. 30, 2016.

(51) Int. Cl.
| | | |
|---|---|---|
| *A61K 31/5517* | (2006.01) | |
| *A61K 31/553* | (2006.01) | |
| *A61P 43/00* | (2006.01) | |
| *A61P 1/04* | (2006.01) | |

(52) U.S. Cl.
CPC ........ *A61K 31/5517* (2013.01); *A61K 31/553* (2013.01); *A61P 1/04* (2018.01); *A61P 43/00* (2018.01)

(58) Field of Classification Search
CPC ... A61K 31/5517; A61K 31/553; A61P 43/00; A61P 1/04
See application file for complete search history.

(56) References Cited

U.S. PATENT DOCUMENTS

2017/0071937 A1    3/2017   Karp et al.

FOREIGN PATENT DOCUMENTS

| DE | 10 2007 032 977 A1 | 1/2009 |
|---|---|---|
| WO | WO 02/46183 A2 | 6/2002 |
| WO | 2009002806 * | 12/2008 |
| WO | WO 2009/002806 A1 | 12/2008 |
| WO | WO 2009/010542 A1 | 1/2009 |
| WO | WO 2014/159356 A1 | 10/2014 |
| WO | WO 2017/120543 A1 | 7/2017 |

OTHER PUBLICATIONS

Bellina F. et al. "Synthesis and biological activity of pyrrole, pyrroline and pyrrolidine derivatives with two aryl groups on adjacent positions", Tetrahedron, (2006), vol. 62, p. 7213-7256.
Bhuiyan, M. et al. "Microwave Assisted Knoevenagel Condensation: Synthesis and Antimicrobial Activities of Some Arylidenemalononitriles", Chemistry Journal (2012), vol. 2, Issue 1, p. 31-37.
Bruning, J. et al. "The First Regioselective Synthesis of a Monosubstituted Staurosporine Precursor", Synthesis, (1994), p. 25-27.
Chen W. et al. "Structure-Guided Design of a Highly Selective Glycogen Synthase Kinase-3b Inhibitor: a Superior Neuroprotective Pyrazolone Showing Antimania Effects", ChemMedChem, (2011), vol. 6, No. 9, p. 1587-1592.
Eils S. et al. "Complete Regioselectivity in Staurosporine Chromophore Formation", Synthesis (1999), p. 275-281.
Mogilaiah K. et al. "Knoevenagel condensation of a,b-unsaturated aromatic aldehydes with barbituric acid under non-catalytic and solvent-free conditions", Indian Journal of Chemistry (2010), vol. 49B, p. 390-393.
Nagaraju S. et al. "On-water' catalyst-free, one-pot synthesis of quaternary centered and spiro-tetrahydrothiophene-barbiturate hybrids", Tetrahedron Letters, (2017), vol. 58, p. 2865-2871.
Peifer C. et al. "Design, Synthesis, and Biological Evaluation of Novel 3-Aryl-4-(1H-indole-3yl)-1,5-dihydro-2H-pyrrole-2-ones as Vascular Endothelial Growth Factor Receptor (VEGF-R) Inhibitors", J. Med. Chem. (2008), vol. 51, p. 3814-3824.
Reddy C. et al. "Knoevenagel condensation of α, β-unsaturated aromatic aldehydes with barbituric acid under non-catalytic and solvent-free conditions", Chinese Chemical Letters, (2007), vol. 18, p. 1431-1435.
Schneider, E. et al. "Base-free Knoevenagel condensation catalyzed by copper metal surfaces", Chem. Communication, (2015), vol. 51, p. 10695-10698.
Wilson, L. et al. "Synthetic staurosporines via a ring closing metathesis strategy as potent JAK3 inhibitors and modulators of allergic responses", Bioorganic & Medicinal Chemistry Letters, (2009), vol. 19, p. 3333-3338.
Wilson L. et al. "Novel cycloalkene indole carbazole alkaloids via the ring closing metathesis reaction", Tetrahedron Letters, (2007), vol. 48, p. 7399-7403.
Zhang P. et al. "Design and Syntheses of Permethyl Ningalin B Analogues: Potent Multidrug Resistance (MDR) Reversal Agents of Cancer Cells", Journal of Medicinal Chemistry, (2010), vol. 53, p. 5108-5120.

* cited by examiner

*Primary Examiner* — Alexander R Pagano
*Assistant Examiner* — Ebenezer O Sackey
(74) *Attorney, Agent, or Firm* — Cooley LLP; J. Dean Farmer; Xixi Sun

(57) ABSTRACT

The present invention relates to 1,5-dihydro-2H-pyrrol-2-one compounds and methods of using them to induce self-renewal of stem/progenitor supporting cells, including inducing the stem/progenitor cells to proliferate while maintaining, in the daughter cells, the capacity to differentiate into tissue cells.

39 Claims, 1 Drawing Sheet

1,5-DIHYDRO-2H-PYRROL-2-ONE COMPOUNDS AND METHODS OF USING SAME

RELATED APPLICATION

This application claims priority to U.S. Application No. 62/441,063, filed Dec. 30, 2016, the entire contents of each of which are incorporated herein by reference.

FIELD OF THE INVENTION

The present invention relates to 1,5-dihydro-2H-pyrrol-2-one compounds and methods of using them to induce self-renewal of stem/progenitor supporting cells, including inducing the stem/progenitor cells to proliferate while maintaining, in the daughter cells, the capacity to differentiate into tissue cells.

BACKGROUND OF THE INVENTION

Stem cells exhibit an extraordinary ability to generate multiple cell types in the body. Besides embryonic stem cells, tissue specific stem cells serve a critical role during development as well as in homeostasis and injury repair in the adult. Stem cells renew themselves through proliferation as well as generate tissue specific cell types through differentiation. The characteristics of different stem cells vary from tissue to tissue, and are determined by their intrinsic genetic and epigenetic status. However, the balance between self-renewal and differentiation of different stem cells are all stringently controlled. Uncontrolled self-renewal may lead to overgrowth of stem cells and possibly tumor formation, while uncontrolled differentiation may exhaust the stem cell pool, leading to an impaired ability to sustain tissue homeostasis. Thus, stem cells continuously sense their environment and appropriately respond with proliferation, differentiation or apoptosis. It would be desirable to drive regeneration by controlling the timing and extent of stem cell proliferation and differentiation. Controlling the proliferation with small molecules that are cleared over time would allow for control of the timing and extent of stem cell proliferation and differentiation. Remarkably, tissue stem cells from different tissues share a limited number of signaling pathways for the regulation of their self-renewal and differentiation, albeit in a very context dependent manner. Some of these pathways are the Wnt and GSK3 pathways.

Lgr5 is expressed across a diverse range of tissues and has been identified as a biomarker of adult stem cells in a variety of tissues such as the gut epithelia (Barker et al. 2007), kidney, hair follicle, and stomach (Barker et al, 2010; Haegebarth & Clevers, 2009). For example, it was first published in 2011, that mammalian inner ear hair cells are derived from LGR5+ cells (Chai et al, 2011, Shi et al. 2012). Lgr5 is a known component of the Wnt/beta-catenin pathway, which has been shown to play major roles in differentiation, proliferation, and inducing stem cell characteristics (Barker et al. 2007).

Permanent damage to the hair cells of the inner ear results in sensorineural hearing loss, leading to communication difficulties in a large percentage of the population. Hair cells are the receptor cells that transduce the acoustic stimulus. Regeneration of damaged hair cells would provide an avenue for the treatment of a condition that currently has no therapies other than prosthetic devices. Although hair cells do not regenerate in the mammalian cochlea, new hair cells in lower vertebrates are generated from epithelial cells, called supporting cells, that surround hair cells.

Prior work has focused on transdifferentiation of supporting cells into hair cells through activation or forced expression of genes that lead to hair cell formation, with a particular focus on mechanisms to enhance expression of Atoh1 (Bermingham et al., 1999; Zheng and Gao, 2000; Izumikawa et al., 2005; Mizutari et al., 2013). Interestingly, cells transduced with Atoh1 vectors have been shown to acquire vestibular phenotypes (Kawamoto et al., 2003; Huang et al., 2009; Yang et al., 2012, 2013), and lack complete development. As mentioned, upregulating Atoh1 via gene insertion has been shown to create non-cochlear cell types that behave in a manner that is not found within the native cochlea. In addition, these methods increase hair cell numbers but decrease supporting cell numbers. Since supporting cells are known to have specialized roles (Ramirez-Camancho 2006, Dale and Jagger 2010), loss of these cells could create problems in proper cochlear function.

Thus, there remains a long felt need for new compounds that can preserve/promote the function of existing cells after injury.

SUMMARY OF THE INVENTION

The present disclosure provides compounds of Formula (I) or (I'),

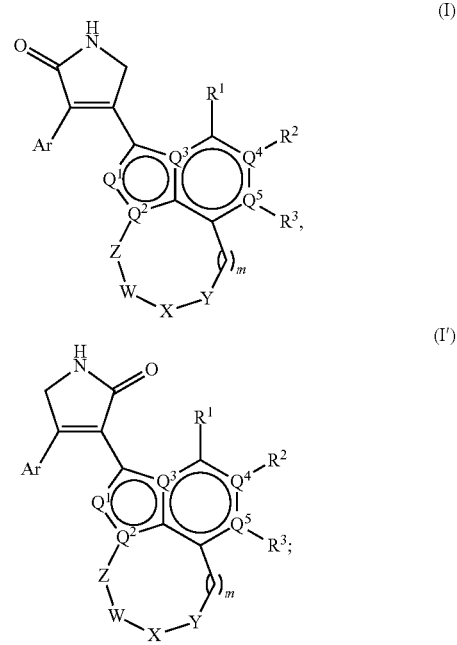

and pharmaceutically acceptable salts or tautomers thereof, wherein:

$Q^1$ is CH or N;
$Q^2$ is C or N;
$Q^3$ is C or N;
$Q^4$ is C or N;
$Q^5$ is C or N;
wherein one to two of $Q^1$, $Q^2$, $Q^3$, $Q^4$, and $Q^5$ is N;
$R^1$ is selected from the group consisting of hydrogen, halo, $C_1$-$C_4$alkyl, $C_1$-$C_4$alkenyl, $C_1$-$C_4$alkynyl, —CN, —OH, —O—$C_1$-$C_4$alkyl, —NH$_2$, —NHC(O)$R^{1a}$, and —S(O)₂NH₂; wherein the alkyl is optionally substituted with one to 3 substituents independently selected from the group consisting of halo and —OH; and wherein $R^{1a}$ is $C_1$-$C_4$alkyl;

$R^2$ is selected from the group consisting of hydrogen, halo, $C_1$-$C_4$alkyl, $C_1$-$C_4$alkenyl, $C_1$-$C_4$alkynyl, —CF₃, —CN, —OH, —O—$C_1$-$C_4$alkyl, —NH₂, —NH($C_1$-$C_4$alkyl), —N($C_1$-$C_4$alkyl)₂, —NHC(O)R²a, and —S(O)₂NH₂; wherein the alkyl is optionally substituted with one to 3 substituents independently selected from the group consisting of halo and —OH; and wherein $R^{2a}$ is $C_1$-$C_4$alkyl; or $R^2$ is absent, if $Q^4$ is N; $R^3$ is selected from the group consisting of hydrogen, halo, $C_1$-$C_4$alkyl, $C_1$-$C_4$alkenyl, $C_1$-$C_4$alkynyl, —CN, —OH, —O—$C_1$-$C_4$alkyl, —NH₂, —NHC(O)$R^{3a}$, and —S(O)₂NH₂; wherein the alkyl is optionally substituted with one to 3 substituents independently selected from the group consisting of halo and —OH; and wherein $R^{3a}$ is $C_1$-$C_4$alkyl; or $R^3$ is absent, if $Q^5$ is N;

Ar is selected from the group consisting of aryl, heteroaryl,

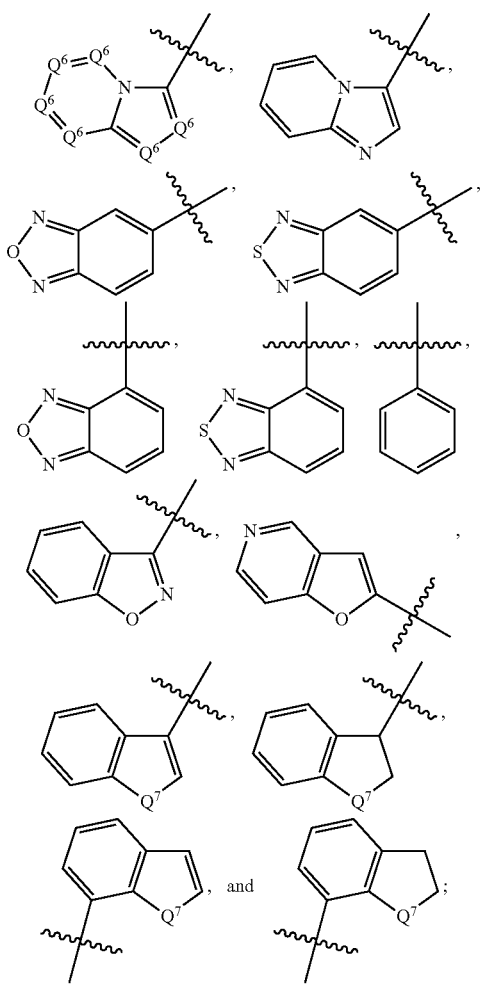

wherein Ar is optionally substituted with deuterium, halo, alkyl, alkoxy, aminoalkoxy, CF₃, and CN;

each $Q^6$ is independently selected from $CR^{Q6}$ and N; wherein $R^{Q6}$ is hydrogen, halo, —CN, lower alkyl, or substituted alkyl;

each $Q^7$ is independently selected from S, O, CH₂, $NR^{Q7}$; where $R^{Q7}$ is hydrogen or optionally substituted $C_1$-$C_4$alkyl;
—Z—W—X—Y— is —C(R^Z)₂—C(R^W)₂—N(R^X)—C(R^Y)₂—, —C(R^Z)₂—C(R^W)₂—CH(R^X)—C(R^Y)₂—, or —C(R^W)₂—CH(R^X)—C(R^Y)₂—;

each $R^Z$ is independently selected from the group consisting of hydrogen, deuterium, halo, and $C_1$-$C_4$alkyl, or both $R^Z$ groups together form $C_3$-$C_6$cycloalkyl or oxo;

each $R^W$ is independently selected from the group consisting of hydrogen, deuterium, halo, and $C_1$-$C_4$alkyl, or both $R^W$ groups together form $C_3$-$C_6$cycloalkyl or oxo;

or $R^Z$ and $R^W$ together with the carbons to which they are attached form a $C_3$-$C_6$cycloalkyl;

$R^X$ is selected from the group consisting of $R^{X1}$, —COR^{X1}, —SO₂R^{X1}, —CON(R^{X2})₂, and —($C_1$-$C_4$alkylene)-$R^{X1}$, and wherein the —($C_1$-$C_4$alkylene)-$R^{X1}$ is optionally substituted with one to four halo on the $C_1$-$C_4$alkylene;

wherein $R^{X1}$ is $C_3$-$C_8$cycloalkyl, heteroaryl, or heterocyclic, wherein the heterocyclic is optionally substituted with one to twelve substituents independently selected from the group consisting of deuterium, halo, —CF₃, —[C(R^{X1a})₂]_p—CN, $C_1$-$C_4$alkyl, —[C(R^{X1a})₂]_p—OH, —[C(R^{X1a})₂]_p—O—$C_1$-$C_4$alkyl, —[C(R^{X1a})₂]_p—NHCOC₁-$C_4$alkyl, —[C(R^{X1a})₂]_p—N($C_1$-$C_4$alkyl)-COC₁-$C_4$alkyl, —[C(R^{X1a})₂]_p—NH₂, —[C(R^{X1a})₂]_p—NH—$C_1$-$C_4$alkyl, —[C(R^{X1a})₂]_p—N—($C_1$-$C_4$alkyl)₂, —[C(R^{X1a})₂]_p—CON—($C_1$-$C_4$alkyl)₂; wherein p is 0, 1, 2, or 3; wherein each $R^{X1a}$ is independently selected from the group consisting of hydrogen, deuterium, halo, —CF₃, and $C_1$-$C_4$alkyl, or both $R^{X1a}$ groups together form $C_3$-$C_6$cycloalkyl;

wherein each $R^{X2}$ is independently hydrogen or $C_1$-$C_4$alkyl;

each $R^Y$ is independently selected from the group consisting of hydrogen, deuterium, halo, and $C_1$-$C_4$alkyl, or both $R^Y$ groups together form $C_3$-$C_6$cycloalkyl or oxo; and m is 0, 1, or 2.

In one aspect the present disclosure provides a method for proliferation of stem cells comprising administering to a cell population an effective amount of a composition provided herein. In some embodiments, proliferation occurs in the absence of a notch activator or an HDAC inhibitor.

Among the various aspects of the present disclosure, therefore, may be noted a method for activating the Wnt pathway in a cell population to increase the capacity of the population for self-renewal, i.e., the capacity for repeated generation of daughter cells with equivalent proliferation and 'cell fate specification' potential, and differentiation, i.e., the capacity for generation of daughter cells specified for differentiation. In one embodiment, the cell population is a cochlear supporting cell population. Preferably, the Wnt pathway is activated upstream of the c-myc gene in members of the population and without any genetic modification of the population. Instead, the Wnt pathway is preferably activated by small molecules that transiently induce such activity. Additionally, the supporting cell population preferably includes supporting cells that are LGR5⁺ and endogenous to the Organ of Corti.

A further aspect of the present disclosure is a method for inducing the self-renewal of stem/progenitor supporting cells comprised by a cochlear cell population. That is, the stem/progenitor supporting cells are induced to proliferate (i.e., divide and form daughter cells) while maintaining, in the daughter cells, the capacity to differentiate into hair cells. In contrast, if the stem/progenitor supporting cells were merely induced to proliferate (without maintaining multipotency), the daughter cells would lack the capacity to divide into hair cells. Further, merely enforcing differentiation of a pre-existing stem/progenitor cell population has the potential to exhaust the stem cell pool. Proliferation is preferably activated by small molecules that transiently induce such activity. Additionally, in certain embodiments the supporting cell population preferably includes supporting cells that are LGR5+ and endogenous to the Organ of Corti.

In a first aspect, methods of using 1,5-dihydro-2H-pyrrol-2-one compounds for inducing the self-renewal of stem/progenitor supporting cells are provided. In some embodiments, 1,5-dihydro-2H-pyrrol-2-one compounds are compounds of Formula (I).

In certain embodiments, therefore, the present disclosure provides methods to induce self-renewal of a population of supporting cells by activating pathways and mechanisms that are known to be involved in inducing stem cell properties, such as those used to create "induced pluripotent stem cells". Preferably, the pathways are activated with small molecules. For example, a compound when applied in vitro to a supporting cell population induces the population to proliferate to a high degree and in high purity in a Stem Cell Proliferation Assay, and also allows the population to differentiate into a high purity population of a tissue cell in a Stem Cell Differentiation Assay. In one such embodiment, the compound induces and maintains stem cell properties by proliferating to produce stem cells that can divide for many generations and maintain the ability to have a high proportion of the resulting cells differentiate into tissue cells. Further, the proliferating stem cells express stem cell markers which may include one or more of Lgr5, Sox2, Opeml, Phex, lin28, Lgr6, cyclin D1, Msx1, Myb, Kit, Gdnf3, Zic3, Dppa3, Dppa4, Dppa5, Nanog, Esrrb, Rexl, Dnmt3a, Dnmt3b, Dnmt31, Utfl, Tell, Oct4, Klf4, Pax6, Six2, Zic1, Zic2, Otx2, Bmi1, CDX2, STAT5, Smad1, Smad2, smad2/3, smad4, smad5, and smad7.

In certain embodiments, the disclosure provides a method for expanding a population of cochlear cells in a cochlear tissue comprising a parent population of cells. In this embodiment, the method comprises contacting the cochlear tissue with a stem cell proliferator to form an expanded population of cells in the cochlear tissue, wherein the stem cell proliferator is capable of (i) forming a proliferation assay final cell population from a proliferation assay initial cell population over a proliferation assay time period in a stem cell proliferation assay and (ii) forming a differentiation assay final cell population from a differentiation assay initial cell population over a differentiation assay time period in a stem cell differentiation assay wherein:

(a) the proliferation assay initial cell population has (i) a proliferation assay initial number of total cells, (ii) a proliferation assay initial number of Lgr5$^+$ cells, (iii) a proliferation assay initial number of hair cells, (iv) a proliferation assay initial Lgr5$^+$ cell fraction that equals the ratio of the proliferation assay initial number of Lgr5$^+$ cells to the proliferation assay initial number of total cells, and (v) a proliferation assay initial hair cell fraction that equals the ratio of the proliferation assay initial number of hair cells to the proliferation assay initial number of total cells;

(b) the proliferation assay final cell population has (i) a proliferation assay final number of total cells, (ii) a proliferation assay final number of Lgr5$^+$ cells, (iii) a proliferation assay final number of hair cells, (iv) a proliferation assay final Lgr5$^+$ cell fraction that equals the ratio of the proliferation assay final number of Lgr5$^+$ cells to the proliferation assay final number of total cells and (v) a proliferation assay final hair cell fraction that equals the ratio of the proliferation assay final number of hair cells to the proliferation assay final number of total cells;

(c) the differentiation assay initial cell population has (i) a differentiation assay initial number of total cells, (ii) a differentiation assay initial number of Lgr5$^+$ cells, (iii) a differentiation assay initial number of hair cells, (iv) a differentiation assay initial Lgr5$^+$ cell fraction that equals the ratio of the differentiation assay initial number of Lgr5$^+$ cells to the differentiation assay initial number of total cells, and (v) a differentiation assay initial hair cell fraction that equals the ratio of the differentiation assay initial number of hair cells to the differentiation assay initial number of total cells;

(d) the differentiation assay final cell population has (i) a differentiation assay final number of total cells, (ii) a differentiation assay final number of Lgr5$^+$ cells, (iii) a differentiation assay final number of hair cells, (iv) a differentiation assay final Lgr5$^+$ cell fraction that equals the ratio of the differentiation assay final number of Lgr5$^+$ cells to the differentiation assay final number of total cells, and (v) a differentiation assay final hair cell fraction that equals the ratio of the differentiation assay final number of hair cells to the differentiation assay final number of total cells;

(e) the proliferation assay final number of Lgr5$^+$ cells exceeds the proliferation assay initial number of Lgr5$^+$ cells by a factor of at least 10; and (f) the differentiation assay final number of hair cells is a non-zero number.

The assay described above does not include applying a notch activator or an HDAC inhibitor.

In certain embodiments, the disclosure provides a method for increasing the cell density of supporting cells in a population of cochlear cells. The method comprises activating pathways and mechanisms that induce stem cell properties in the supporting cells, proliferating the activated supporting cells (while maintaining the multi-potent character of the supporting cells in the newly formed daughter cells) and thereafter allowing (or even inducing) the expanded population to differentiate into hair cells to form an expanded cochlear cell population wherein the cell density of hair cells in the expanded cochlear cell population exceeds the cell density of hair cells in the original (non-expanded) cochlear cell population. In some embodiments, such proliferation occurs in the absence of a notch activator or an HDAC inhibitor. In some embodiments, the supporting cell population is an in vitro supporting cell population. In other embodiments, the supporting cell population is an in vivo supporting cell population. Additionally, the proliferation stage is preferably controlled to substantially maintain the native organization of the cochlear structure. The proliferation is induced by the compound described herein that transiently induces such activity rather than by induction of c-myc and without any genetic modification of the population. In some embodiments, such proliferation occurs in the absence of a notch activator or an HDAC inhibitor. Additionally, in certain embodiments the supporting cell population preferably includes supporting cells that are LGR5$^+$ and endogenous to the Organ of Corti.

In certain embodiments, the disclosure provides a method for increasing the cell density of Lgr5$^+$ supporting cells in a population of cochlear cells. The method comprises activating pathways and mechanisms that induce or maintain stem cell properties in the Lgr5$^+$ supporting cells, proliferating the activated Lgr5$^+$ supporting cells (while maintaining such stem cell properties) and thereafter allowing (or even inducing) the expanded population to differentiate into hair cells to form an expanded cochlear cell population wherein the cell density of hair cells in the expanded cochlear cell population exceeds the cell density of hair cells in the original (non-expanded) cochlear cell population. In some embodiments for increasing the cell density of $Lgr5^+$ supporting cells in a population of cochlear cells, such increasing of the cell density occurs in the absence of a notch activator or an HDAC inhibitor. In some embodiments, the $Lgr5^+$ supporting cell population is an in vitro $Lgr5^+$ stem cell population. In other embodiments, the $Lgr5^+$ supporting cell population is an in vivo supporting cell population. Additionally, in certain embodiments the proliferation stage is preferably controlled to substantially maintain the native organization of the cochlear structure.

In certain embodiments, the disclosure provides a method for increasing the cell density of hair cells in an initial population of cochlear cells, the initial population (which may be an in vivo or an in vitro population) comprises hair cells, $Lgr5^-$ supporting cells, and $Lgr5^+$ supporting cells. In some embodiments for increasing the cell density of hair cells in an initial population of cochlear cells, such increasing of the cell density occurs in the absence of a notch activator or an HDAC inhibitor. The method comprises administering to the initial population a compound described herein.

In certain embodiments, the method produces stem cells in a Stem Cell Proliferation Assay that express stem cells markers $Lgr5^+$. In certain embodiments, if a mixed population of $Lgr5^+$ and non-$Lgr5^+$ stems are placed in a Stem Cell Proliferation Assay, the method increases the fraction of cells in the population that are $Lgr5^+$. In some embodiments, such production of stem cells in a Stem Cell Proliferation Assay occurs in the absence of a notch activator or an HDAC inhibitor.

Expanding supporting cell populations to a degree that destroys the native organization of the cochlear structure could inhibit cochlear function. Driving proliferation of existing supporting cells with a small molecule signal may allow for a more controlled regeneration of hair cells than using gene delivery, which is incapable of targeting a specific cell type and permanently alters a cell's genetic information. An approximately normal cochlear structure is desired with rows of hair cells that have supporting cells between them, and hair cells do not contact other hair cells. Further, it would be desirable to avoid using genetic modification to drive proliferation to create large cell aggregations in the cochlea that disrupt the organ's anatomy.

In certain embodiments, the disclosure provides a method for increasing the cell density of hair cells in an initial population of cochlear cells comprising hair cells and supporting cells. The method comprises selectively expanding the number of supporting cells in the initial population to form an intermediate cochlear cell population wherein the ratio of the number of supporting cells to hair cells in the intermediate cochlear cell population exceeds the ratio of the number of supporting cells to hair cells in the initial cochlear cell population. The method further comprises generating hair cells in the intermediate cochlear cell population to form an expanded cochlear cell population wherein the ratio of the number of hair cells to supporting cells in the expanded cochlear cell population exceeds the ratio of the number of hair cells to supporting cells in the intermediate cochlear cell population. In some embodiments, the method does not comprise the use of a notch activator or an HDAC inhibitor.

In certain embodiments, the disclosure provides a method for increasing the number of $Lgr5^+$ supporting cells or increasing the $Lgr5^+$ activity in an initial population of cochlear cells, wherein the initial population comprises supporting cells and hair cells. For example, in one such method an intermediate population is formed in which the number of $Lgr5^+$ supporting cells is expanded relative to the initial population. Alternatively, in one such method an intermediate population is formed in which the $Lgr5^+$ activity of the supporting cells relative to the initial population is increased. Alternatively, a method where the number of $Lgr5^+$ cells is increased relative to the initial cell population by activating $Lgr5^+$ expression in cell types that normally lack or have very low levels of $Lgr5^+$. In some embodiments, these alternative methods do not comprise the use of a notch activator or an HDAC inhibitor. By way of further example, an intermediate population is formed in which the number of $Lgr5^+$ supporting cells is expanded and the Lgr5 activity is increased relative to the initial cochlear cell population. Thereafter, hair cells in the intermediate cochlear cell population may be generated to form an expanded cochlear cell population wherein the ratio of hair cells to supporting cells in the expanded cochlear cell population exceeds the ratio of the number of hair cells to supporting cells in the intermediate cochlear cell population.

In each of the aforementioned embodiments of the present disclosure, stemness is induced by activating Wnt or inhibiting GSK3 activity. In some embodiments, inducing stemness does not comprise the use of a notch activator or an HDAC inhibitor.

In certain embodiments, the disclosure provides methods for preventing and treating auditory dysfunction. For example, in certain embodiments, the disclosure provides methods for preventing or treating auditory impairments in a subject comprising administering to said subject an effective amount of a compound provided herein.

In certain embodiments, the present disclosure also relates to ex-vivo uses of cells described herein. For example, approaches described herein can be used for high throughput screen and for discovery purposes. For example, certain embodiments of the present disclosure are useful for identifying agents that proliferate hair cell progenitors and/or increase numbers of hair cells, and also agents that protect supporting cells and/or hair cells (e.g. to support their survival), and also for identifying agents that are toxic or not toxic to supporting cells or differentiated progeny including hair cells.

In certain embodiments, the disclosure provides for methods for inhibiting the loss or death of the cells of the auditory system in a subject comprising administering to said subject an effective amount of the compound described herein or derivative thereof or pharmaceutically acceptable salt thereof and an acceptable carrier or excipient, thereby inhibiting loss or death of the cells of the auditory system in the subject. In some embodiments, the method does not comprise the use of a notch activator or an HDAC inhibitor.

In certain embodiments, the disclosure provides methods for maintaining or promoting the growth of cells of the auditory system in a subject comprising administering to said subject the compound described herein or derivative thereof or pharmaceutically acceptable salt thereof in an effective amount so as to augment or initiate endogenous repair, thereby maintaining or promoting the growth of cells of the auditory system in the subject.

Also described herein is a method for expanding a population of cochlear cells in a cochlear tissue comprising a parent population of cells, the parent population including supporting cells and a number of $Lgr5^+$ cells, the method comprising contacting the cochlear tissue with a stem cell proliferator to form an expanded population of cells in the cochlear tissue, wherein the stem cell proliferator is capable (i) in a stem cell proliferation assay of increasing the number of Lgr5$^+$ cells in a stem cell proliferation assay cell population by a factor of at least 10 and (ii) in a stem cell differentiation assay of forming hair cells from a cell population comprising Lgr5$^+$ cells. In some embodiments for expanding a population of cochlear cells, the method does not comprise the use of a notch activator or an HDAC inhibitor.

Also described herein is a method for expanding a population of cochlear cells in a cochlear tissue comprising a parent population of cells, the parent population including supporting cells, the method comprising contacting the cochlear tissue with a stem cell proliferator to form an expanded population of cells in the cochlear tissue. The stem cell proliferator can be capable of (i) forming a proliferation assay final cell population from a proliferation assay initial cell population over a proliferation assay time period in a stem cell proliferation assay and (ii) forming a differentiation assay final cell population from a differentiation assay initial cell population over a differentiation assay time period in a stem cell differentiation assay wherein: (a) the proliferation assay initial cell population has (i) a proliferation assay initial number of total cells, (ii) a proliferation assay initial number of Lgr5$^+$ cells, (iii) a proliferation assay initial number of hair cells, (iv) a proliferation assay initial Lgr5$^+$ cell fraction that equals the ratio of the proliferation assay initial number of Lgr5$^+$ cells to the proliferation assay initial number of total cells, and (v) a proliferation assay initial hair cell fraction that equals the ratio of the proliferation assay initial number of hair cells to the proliferation assay initial number of total cells; (b) the proliferation assay final cell population has (i) a proliferation assay final number of total cells, (ii) a proliferation assay final number of Lgr5$^+$ cells, (iii) a proliferation assay final number of hair cells, (iv) a proliferation assay final Lgr5$^+$ cell fraction that equals the ratio of the proliferation assay final number of Lgr5$^+$ cells to the proliferation assay final number of total cells and (v) a proliferation assay final hair cell fraction that equals the ratio of the proliferation assay final number of hair cells to the proliferation assay final number of total cells; (c) the differentiation assay initial cell population has (i) a differentiation assay initial number of total cells, (ii) a differentiation assay initial number of Lgr5$^+$ cells, (iii) a differentiation assay initial number of hair cells, (iv) a differentiation assay initial Lgr5$^+$ cell fraction that equals the ratio of the differentiation assay initial number of Lgr5$^+$ cells to the differentiation assay initial number of total cells, and (v) a differentiation assay initial hair cell fraction that equals the ratio of the differentiation assay initial number of hair cells to the differentiation assay initial number of total cells; (d) the differentiation assay final cell population has (i) a differentiation assay final number of total cells, (ii) a differentiation assay final number of Lgr5$^+$ cells, (iii) a differentiation assay final number of hair cells, (iv) a differentiation assay final Lgr5$^+$ cell fraction that equals the ratio of the differentiation assay final number of Lgr5$^+$ cells to the differentiation assay final number of total cells, and (v) a differentiation assay final hair cell fraction that equals the ratio of the differentiation assay final number of hair cells to the differentiation assay final number of total cells; (e) the proliferation assay final number of Lgr5$^+$ cells exceeds the proliferation assay initial number of Lgr5$^+$ cells by a factor of at least 10; and (f) the differentiation assay final number of hair cells is a non-zero number. In some embodiments of the assay described above, the assay does not comprise the use of a notch activator or an HDAC inhibitor.

The proliferation assay final number of Lgr5$^+$ cells can be greater than the proliferation assay initial number of Lgr5$^+$ cells by a factor of at least 50, or by a factor of at least 100. The expanded population of cells in the cochlear tissue can include a greater number of hair cells than does the parent population. The proliferation assay final Lgr5$^+$ cell fraction can be greater than the differentiation assay initial Lgr5$^+$ cell fraction by at least a factor of 2. The differentiation assay final hair cell fraction can be greater than the proliferation assay initial hair cell fraction by at least a factor of 2. The proliferation assay final hair cell fraction can be at least 25% less than the proliferation assay initial hair cell fraction. The proliferation assay final Lgr5$^+$ cell fraction can be at least 10% greater than proliferation assay initial Lgr5$^+$ cell fraction. One of more morphological characteristics of the cochlear tissue can be maintained. Native morphology can be maintained. The stem cell proliferator can be dispersed in a biocompatible matrix, which can be a biocompatible gel or foam. The cochlear tissue can be an in vivo cochlear tissue or an ex vivo cochlear tissue. The method can produce a population of Lgr5$^+$ cells that are in s-phase. The cochlear tissue can be in a subject, and contacting the cochlear tissue with the compound can be achieved by administering the compound trans-tympanically to the subject. Contacting the cochlear tissue with the compound can result in improved auditory functioning of the subject.

Also described herein is a method of treating a subject who has, or is at risk of developing, hearing loss. The method can include trans-tympanically administering to a cochlear tissue of the subject compound provided herein.

Also described herein is a method of generating Myo7a+ cochlear cells. The method can include contacting Lgr5+ cochlear cells with a compound provided herein, thereby generating an expanded population of Lgr5+ cells, thereby generating Myo7a+ cochlear cells.

Other objects and features will be in part apparent and in part pointed out hereinafter.

Definitions

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration" refers to introducing a substance into a subject. In some embodiments, administration is auricular, intraauricular, intracochlear, intravestibular, or transtympanically, e.g., by injection. In some embodiments, administration is directly to the inner ear, e.g. injection through the round or oval, otic capsule, or vestibular canals. In some embodiments, administration is directly into the inner ear via a cochlear implant delivery system. In some embodiments, the substance is injected transtympanically to the middle ear. In certain embodiments "causing to be administered" refers to administration of a second component after a first component has already been administered (e.g., at a different time and/or by a different actor).

An "antibody" refers to an immunoglobulin polypeptide, or fragment thereof, having immunogen binding ability.

As used herein, an "agonist" is an agent that causes an increase in the expression or activity of a target gene, protein, or a pathway, respectively. Therefore, an agonist can bind to and activate its cognate receptor in some fashion, which directly or indirectly brings about this physiological effect on the target gene or protein. An agonist can also increase the activity of a pathway through modulating the activity of pathway components, for example, through inhibiting the activity of negative regulators of a pathway. Therefore, a "Wnt agonist" can be defined as an agent that increases the activity of Wnt pathway, which can be measured by increased TCF/LEF-mediated transcription in a cell. Therefore, a "Wnt agonist" can be a true Wnt agonist that bind and activate a Frizzled receptor family member, including any and all of the Wnt family proteins, an inhibitor of intracellular beta-catenin degradation, and activators of TCF/LEF.

An "antagonist" refers to an agent that binds to a receptor, and which in turn decreases or eliminates binding by other molecules.

"Anti-sense" refers to a nucleic acid sequence, regardless of length, that is complementary to the coding strand or mRNA of a nucleic acid sequence. Antisense RNA can be introduced to an individual cell, tissue or organanoid. An anti-sense nucleic acid can contain a modified backbone, for example, phosphorothioate, phosphorodithioate, or other modified backbones known in the art, or may contain non-natural internucleoside linkages.

As referred to herein, a "complementary nucleic acid sequence" is a nucleic acid sequence capable of hybridizing with another nucleic acid sequence comprised of complementary nucleotide base pairs. By "hybridize" is meant pair to form a double-stranded molecule between complementary nucleotide bases (e.g., adenine (A) forms a base pair with thymine (T), as does guanine (G) with cytosine (C) in DNA) under suitable conditions of stringency. (See, e.g., Wahl, G. M. and S. L. Berger (1987) Methods Enzymol. 152:399; Kimmel, A. R. (1987) Methods Enzymol. 152: 507).

"Auricular administration" refers to a method of using a catheter or wick device to administer a composition across the tympanic membrane to the inner ear of the subject. To facilitate insertion of the wick or catheter, the tympanic membrane may be pierced using a suitably sized syringe or pipette. The devices could also be inserted using any other methods known to those of skill in the art, e.g., surgical implantation of the device. In particular embodiments, the wick or catheter device may be a stand-alone device, meaning that it is inserted into the ear of the subject and then the composition is controllably released to the inner ear. In other particular embodiments, the wick or catheter device may be attached or coupled to a pump or other device that allows for the administration of additional compositions. The pump may be automatically programmed to deliver dosage units or may be controlled by the subject or medical professional.

"Biocompatible Matrix" as used herein is a polymeric carrier that is acceptable for administration to humans for the release of therapeutic agents. A Biocompatible Matrix may be a biocompatible gel or foam.

"Cell Aggregate" as used herein shall mean a body cells in the Organ of Corti that have proliferated to form a cluster of a given cell type that is greater than 40 microns in diameter and/or produced a morphology in which greater than 3 cell layers reside perpendicular to the basilar membrane. A "Cell Aggregate" can also refer a process in which cell division creates a body of cells that cause one or more cell types to breach the reticular lamina, or the boundary between endolymph and perilymph "Cell Density" as used herein in connection with a specific cell type is the mean number of that cell type per area in a Representative Microscopy Sample. The cell types may include but are not limited to $Lgr5^+$ cells, hair cells, or supporting cells. The Cell Density may be assessed with a given cell type in a given organ or tissue, including but not limited to the cochlea or Organ of Corti. For instance, the $Lgr5^+$ Cell Density in the Organ of Corti is the Cell Density of $Lgr5^+$ cells as measured across the Organ of Corti. Typically, supporting cells and $Lgr5^+$ cells will be enumerated by taking cross sections of the Organ of Corti. Typically, hair cells will be enumerated by looking down at the surface of the Organ of Corti, though cross sections may be used in some instances, as described in a Representative Microscopy Sample. Typically, Cell Density of $Lgr5^+$ cells will be measured by analyzing whole mount preparations of the Organ of Corti and counting the number of Lgr5 cells across a given distance along the surface of the epithelia, as described in a Representative Microscopy Sample. Hair cells may be identified by their morphological features such as bundles or hair cell specific stains (e.g., Myosin VIIa, Prestin, vGlut3, Pou4f3, Espin, conjugated-Phalloidin, PMCA2, Ribeye, Atoh1, etc). $Lgr5^+$ cells may be identified by specific stains or antibodies (e.g. Lgr5-GFP transgenic reporter, anti-Lgr5 antibody, etc.)

"Cochlear Concentration" as used herein will be the concentration of a given agent as measured through sampling cochlear fluid. Unless otherwise noted, the sample should contain a substantial enough portion of the cochlear fluid so that it is approximately representative of the average concentration of the agent in the cochlea. For example, samples may be drawn from a vestibular canal, and a series of fluid samples drawn in series such that individual samples are comprised of cochlear fluid in specified portions of the cochlea "Complementary nucleic acid sequence" refers to a nucleic acid sequence capable of hybridizing with another nucleic acid sequence comprised of complementary nucleotide base pairs.

"Cross-Sectional Cell Density" as used herein in connection with a specific cell type is the mean number of that cell type per area of cross section through a tissue in a Representative Microscopy Sample. Cross sections of the Organ of Corti can also be used to determine the number of cells in a given plane. Typically, hair cells Cross-sectional Cell Density will be measured by analyzing whole mount preparations of the Organ of Corti and counting the number of hair cells across a given distance in cross sections taken along a portion of the epithelia, as described in a Representative Microscopy Sample. Typically, Cross-sectional Cell Density of $Lgr5^+$ cells will be measured by analyzing whole mount preparations of the Organ of Corti and counting the number of $Lgr5^+$ cells across a given distance in cross sections taken along a portion of the epithelia, as described in a Representative Microscopy Sample. Hair cells may be identified by their morphological features such as bundles or hair cell specific stains (suitable stains include e.g., Myosin VIIa, Prestin, vGlut3, Pou4f3, conjugated-Phalloidin, PMCA2, Atoh1, etc.). $Lgr5^+$ cells may be identified by specific stains or antibodies (suitable stains and antibodies include fluorescence in situ hybridization of Lgr5 mRNA, Lgr5-GFP transgenic reporter system, anti-Lgr5 antibodies, etc.).

"Decreasing" refers to decreasing by at least 5%, for example, 5, 6, 7, 8, 9, 10, 15, 20, 25, 30, 35, 40, 45, 50, 55, 60, 65, 70, 75, 80, 85, 90, 95, 99 or 100%, for example, as compared to the level of reference.

"Decreases" also means decreases by at least 1-fold, for example, 1, 2, 3, 4, 5, 6, 7, 8, 9, 10, 15, 20, 30, 40, 50, 60, 70, 80, 90, 100, 200, 500, 1000-fold or more, for example, as compared to the level of a reference.

"Differentiation Period" as used herein is the duration of time in which there is an Effective Stemness Driver Concentration without an Effective Differentiation Inhibition Concentration.

"Effective Concentration" may be the Effective Stemness Driver Concentration for a Stemness Driver or the Effective Diffusion Inhibition Concentration for a Diffusion Inhibitor.

"Effective Differentiation Inhibition Concentration" is the minimum concentration of a Differentiation Inhibitor that does not allow more than a 50% increase in the fraction of the total population of cells that are hair cells at the end of the Stem Cell Proliferation Assay compared to the start of the Stem Cell Proliferation Assay In measuring the Effective Differentiation Inhibition Concentration, a Hair Cell stain for cells may be used with flow cytometry to quantify hair cells for a mouse strain that is not an Atoh1-GFP mouse. Alternatively, and Atoh1-GFP mouse strain may be used.

"Effective Release Rate" (mass/time) as used herein is the Effective Concentration (mass/volume)*30 uL/1 hour.

"Effective Stemness Driver Concentration" is the minimum concentration of a Stemness Driver that induces at least 1.5-fold increase in number of LGR5+ cells in a Stem Cell Proliferation Assay compared to the number of Lgr5+ cells in a Stem Cell Proliferation Assay performed without the Stemness Driver and with all other components present at the same concentrations.

"Eliminate" means to decrease to a level that is undetectable.

"Engraft" or "engraftment" refers to the process of stem or progenitor cell incorporation into a tissue of interest in vivo through contact with existing cells of the tissue. "Epithelial progenitor cell" refers to a multipotent cell which has the potential to become restricted to cell lineages resulting in epithelial cells.

"Epithelial stem cell" refers to a multipotent cell which has the potential to become committed to multiple cell lineages, including cell lineages resulting in epithelial cells.

"Fragment" refers to a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"GSK3 inhibitor" is a composition that inhibits the activity of GSK3, GSK-3alpha, and/or GSK-3beta.

"GSK3beta," "GSK3β," and "GSK3B" as used interchangeably herein are acronyms for glycogen synthase kinase 3 beta, "GSK3beta inhibitor" is a composition that inhibits the activity of GSK3beta.

"Hybridize" refers to pairing to form a double-stranded molecule between complementary nucleotide bases (e.g., adenine (A) forms a base pair with thymine (T), as does guanine (G) with cytosine (C) in DNA) under suitable conditions of stringency. (See, e.g., Wahl, G. M. and S. L. Berger (1987) Methods Enzymol. 152:399; Kimmel, A. R. (1987) Methods Enzymol. 152:507).

An "inhibitor" refers to an agent that causes a decrease in the expression or activity of a target gene or protein, respectively. An "antagonist" can be an inhibitor, but is more specifically an agent that binds to a receptor, and which in turn decreases or eliminates binding by other molecules.

As used herein, an "inhibitory nucleic acid" is a double-stranded RNA, RNA interference, miRNA, siRNA, shRNA, or antisense RNA, or a portion thereof, or a mimetic thereof, that when administered to a mammalian cell results in a decrease in the expression of a target gene. Typically, a nucleic acid inhibitor comprises at least a portion of a target nucleic acid molecule, or an ortholog thereof, or comprises at least a portion of the complementary strand of a target nucleic acid molecule. Typically, expression of a target gene is reduced by 10%, 25%, 50%, 75%, or even 90-100%.

"In Vitro Lgr5 activity" refers to the level of expression or activity of Lgr5 in an in vitro population of cells. It may be measured, for example, in cells derived from a Lgr5-GFP expressing mouse such as a B6.129P2-Lgr5tm1(cre/ERT2) Cle/J mouse (also known as Lgr5-EGFP-IRES-creERT2 or Lgr5-GFP mouse, Jackson Lab Stock No: 008875) by dissociating cells to single cells, staining with propidium iodide (PI), and analyzing the cells using a flow cytometer for Lgr5-GFP expression. Inner ear epithelial cells from wild-type (non-Lgr5-GFP) mice that passing the same culturing and analyzing procedures can be used as a negative control. Typically, two population of cells are shown in the bivariate plot with GFP/FITC as one variable, which include both GFP positive and GFP negative populations. Lgr5-positive cells are identified by gating GFP positive cell population. The percentage of Lgr5-positive cells are measured by gating GFP positive cell population against both GFP negative population and the negative control. The number of Lgr5-positive cells is calculated by multiplying the total number of cells by the percentage of Lgr5-positive cells. For cells derived from non-Lgr5-GFP mice, Lgr5 activity can be measured using an anti-Lgr5 antibody or quantitative-PCR on the Lgr5 gene.

"In Vivo Lgr5 activity" as used herein is the level of expression or activity of Lgr5 in a subject. It may be measured, for example, by removing an animal's inner ear and measuring Lgr5 protein or Lgr5 mRNA. Lgr5 protein production can be measured using an anti-Lgr5 antibody to measure fluorescence intensity as determined by imaging cochlear samples, where fluorescence intensity is used as a measure of Lgr5 presence. Western blots can be used with an anti-Lgr5 antibody, where cells can be harvested from the treated organ to determine increases in Lgr5 protein. Quantitative-PCR or RNA in situ hybridization can be used to measure relative changes in Lgr5 mRNA production, where cells can be harvested from the inner ear to determine changes in Lgr5 mRNA. Alternatively, Lgr5 expression can be measured using an Lgr5 promoter driven GFP reporter transgenic system, where the presence or intensity GFP fluoresce can be directly detected using flow cytometry, imaging, or indirectly using an anti-GFP antibody.

"Increases" also means increases by at least 1-fold, for example, 1, 2, 3, 4, 5, 6, 7, 8, 9, 10, 15, 20, 30, 40, 50, 60, 70, 80, 90, 100, 200, 500, 1000-fold or more, for example, as compared to the level of a as compared to the level of a reference standard.

"Increasing" refers to increasing by at least 5%, for example, 5, 6, 7, 8, 9, 10, 15, 20, 25, 30, 35, 40, 45, 50, 55, 60, 65, 70, 75, 80, 85, 90, 95, 99, 100% or more, for example, as compared to the level of a reference.

"Intraauricular administration" refers to administration of a composition to the middle or inner ear of a subject by directly injecting the composition.

"Intracochlear" administration refers to direct injection of a composition across the tympanic membrane and across the round or oval membrane into the cochlea.

"Intravestibular" administration refers to direct injection of a composition across the tympanic membrane and across the round or oval membrane into the vestibular organs.

"Isolated" refers to a material that is free to varying degrees from components which normally accompany it as found in its native state. "Isolate" denotes a degree of separation from original source or surroundings.

"Lgr5" is an acronym for the Leucine-rich repeat-containing G-protein coupled receptor 5, also known as G-protein coupled receptor 49 (GPR49) or G-protein coupled receptor 67 (GPR67). It is a protein that in humans is encoded by the Lgr5 gene.

"Lgr5 activity" is defined as the level of activity of Lgr5 in a population of cells. In an in vitro cell population, Lgr5 activity may be measured in an in vitro Lgr5 Activity assay. In an in vivo cell population, Lgr5 activity may be measured in an in vivo Lgr5 Activity assay.

"Lgr5$^+$ cell" or "Lgr5-positive cell" as used herein is a cell that expresses Lgr5. "Lgr5$^+$ cell" as used herein is a cell that is not Lgr5$^+$.

"Lineage Tracing" as used herein is using a mouse line that enables fate tracing of any cell that expresses a target gene at the time of reporter induction. This can include hair cell or supporting cells genes (Sox2, Lgr5, MyosinVIIa, Pou4f3, etc). For example, lineage tracing may use an Lgr5-EGFP-IRES-creERT2 mouse crossed with a reporter mouse, which upon induction, allows one to trace the fate of cells that expressed Lgr5 at the time of induction. By further example, Lgr5 cells can be isolated into single cells and cultured in a Stem Cell Proliferation Assay to generate colonies, then subsequently differentiated in a Differentiation Assay and analyzed for cell fate by staining for hair cell and/or supporting cell proteins and determining the reporter colocalization with either hair cell or supporting cell staining to determine the Lgr5 cells' fate. In addition, lineage tracing can be performed in cochlear explants to track supporting cell or hair cell fate within the intact organ after treatment. For example, Lgr5 cell fate can be determined by isolating the cochlea from a Lgr5-EGFP-IRES-creERT2 mouse crossed with a reporter mouse, and inducing the reporter in Lgr5 cells before or during treatment. The organ can then be analyzed for cell fate by staining for hair cell and/or supporting cell proteins and determining the reporter colocalization with either hair cell or supporting cell staining to determine the Lgr5 cells' fate. In addition, lineage tracing can be performed in vivo track supporting cell or hair cell fate within the intact organ after treatment. For example, Lgr5 cell fate can be determined inducing a reporter in an Lgr5-EGFP-IRES-creERT2 mouse crossed with a reporter mouse, treating the animal, then isolating the cochlea. The organ can then be analyzed for cell fate by staining for hair cell and/or supporting cell proteins and determining the reporter colocalization with either hair cell or supporting cell staining to determine the Lgr5 cells' fate. Lineage tracing may be performed using alternative reporters of interest as is standard in the art.

"Mammal" refers to any mammal including but not limited to human, mouse, rat, sheep, monkey, goat, rabbit, hamster, horse, cow or pig.

"Mean Release Time" as used herein is the time in which one-half of an agent is released into phosphate buffered saline from a carrier in a Release Assay.

"Native Morphology" as used herein is means that tissue organization largely reflects the organization in a healthy tissue.

"Non-human mammal", as used herein, refers to any mammal that is not a human.

As used in relevant context herein, the term "number" of cells can be 0, 1, or more cells.

"Organ of Corti" as used herein refers to the sensory cells (inner and outer hair cells) of the hearing organ located in the cochlea.

"Organoid" or "epithelial organoid" refers to a cell cluster or aggregate that resembles an organ, or part of an organ, and possesses cell types relevant to that particular organ.

"Population" of cells refers to any number of cells greater than 1, but is preferably at least $1\times10^3$ cells, at least $1\times10^4$ cells, at least at least $1\times10^5$ cells, at least $1\times10^6$ cells, at least $1\times10^7$ cells, at least $1\times10^8$ cells, at least $1\times10^9$ cells, or at least $1\times10^{10}$ cells.

"Progenitor cell" as used herein refers to a cell that, like a stem cell, has the tendency to differentiate into a specific type of cell, but is already more specific than a stem cell and is pushed to differentiate into its "target" cell.

"Reference" means a standard or control condition (e.g., untreated with a test agent or combination of test agents).

"Release Assay" as used herein is a test in which the rate of release of an agent from a Biocompatible Matrix through dialysis membrane to a saline environment. An exemplary Release Assay may be performed by placing 30 microliters of a composition in 1 ml Phosphate Buffered Saline inside saline dialysis bag with a suitable cutoff, and placing the dialysis bag within 10 ml of Phosphate Buffered Saline at 37° C. The dialysis membrane size may be chosen based on agent size in order to allow the agent being assessed to exit the membrane. For small molecule release, a 3.5-5 kDa cutoff may be used. The Release Rate for a composition may change over time and may be measured in 1 hour increments.

"Representative Microscopy Sample" as used herein describes a sufficient number of fields of view within a cell culture system, a portion of extracted tissue, or an entire extracted organ that the average feature size or number being measured can reasonably be said to represent the average feature size or number if all relevant fields were measured. For example, in order to assess the hair cell counts at a frequency range on the Organ of Corti, ImageJ software (NIH) can used to measure the total length of cochlear whole mounts and the length of individual counted segments. The total number of inner hair cells, outer hair cells, and supporting cells can be counted in the entire or fraction of any of the four cochlear segments of 1200-1400 µm (apical, mid-apical, mid-basal, and basal) at least 3 fields of view at 100 µm field size would be reasonably considered a Representative Microscopy Sample. A Representative Microscopy sample can include measurements within a field of view, which can be measured as cells per a given distance. A Representative Microscopy sample can be used to assess morphology, such as cell-cell contacts, cochlear architecture, and cellular components (e.g., bundles, synapses).

"Rosette Patterning" is a characteristic cell arrangement in the cochlea in which <5% hair cells are adjacent to other hair cells.

The term "sample" refers to a volume or mass obtained, provided, and/or subjected to analysis. In some embodiments, a sample is or comprises a tissue sample, cell sample, a fluid sample, and the like. In some embodiments, a sample is taken from (or is) a subject (e.g., a human or animal subject). In some embodiments, a tissue sample is or comprises brain, hair (including roots), buccal swabs, blood, saliva, semen, muscle, or from any internal organs, or cancer, precancerous, or tumor cells associated with any one of these. A fluid may be, but is not limited to, urine, blood, ascites, pleural fluid, spinal fluid, and the like. A body tissue can include, but is not limited to, brain, skin, muscle, endometrial, uterine, and cervical tissue or cancer, precancerous, or tumor cells associated with any one of these. In an embodiment, a body tissue is brain tissue or a brain tumor or cancer. Those of ordinary skill in the art will appreciate that, in some embodiments, a "sample" is a "primary sample" in that it is obtained from a source (e.g., a subject); in some embodiments, a "sample" is the result of processing of a primary sample, for example to remove certain potentially contaminating components and/or to isolate or purify certain components of interest.

"Self-renewal" refers to the process by which a stem cell divides to generate one (asymmetric division) or two (symmetric division) daughter cells with development potentials that are indistinguishable from those of the mother cell. Self-renewal involves both proliferation and the maintenance of an undifferentiated state.

"siRNA" refers to a double stranded RNA. Optimally, an siRNA is 18, 19, 20, 21, 22, 23 or 24 nucleotides in length and has a 2 base overhang at its 3' end. These dsRNAs can be introduced to an individual cell or culture system. Such siRNAs are used to downregulate mRNA levels or promoter activity.

"Stem cell" refers to a multipotent cell having the capacity to self-renew and to differentiate into multiple cell lineages.

"Stem Cell Differentiation Assay" as used herein is an assay to determine the differentiation capacity of stem cells. In an exemplary Stem Cell Differentiation Assay, the number of cells for an initial cell population is harvested from a Atoh1-GFP mouse between the age of 3 to 7 days, by isolating the Organ of Corti sensory epithelium, dissociating the epithelium into single cells, and passing the cells through a 40 um cell strainer. Approximately 5000 cells are entrapped in 40 µl of culture substrate (for example: Matrigel (Corning, Growth Factor Reduced)) and placed at the center of wells in a 24-well plate with 500 µl of an appropriate culture media, growth factors and agent being tested. Appropriate culture media and growth factors include Advanced DMEM/F12 with media Supplements (1×N2, 1×B27, 2 mM Glutamax, 10 mM HEPES, 1 mM N-acetylcysteine, and 100 U/ml Penicillin/100 µg/ml Streptomycin) and growth factors (50 ng/ml EGF, 50 ng/ml bFGF, and 50 ng/ml IGF-1) as well as the agent(s) being assessed are added into each well. Cells are cultured for 10 days in a standard cell culture incubator at 37° C. and 5% $CO_2$, with media change every 2 days. These cells are then cultured by removing the Stem Cell Proliferation Assay agents and replacing with Basal culture media and molecules to drive differentiation. An appropriate Basal culture media is Advanced DMEM/F12 supplemented with 1×N2, 1×B27, 2 mM Glutamax, 10 mM HEPES, 1 mM N-acetylcysteine, and 100 U/ml Penicillin/100 µg/ml Streptomycin and appropriate molecules to drive differentiation are 3 µM CHIR99021 and 5 µM DAPT for 10 days, with media change every 2 days. The number of hair cells in a population may be measured by using flow cytometry for GFP. Hair cell differentiation level can further be assessed using qPCR to measure hair cell marker (e.g., Myo7a) expression level normalized using suitable and unregulated references or housekeeping genes (e.g., Hprt). Hair cell differentiation level can also be assessed by immunostaining for hair cell markers (eg. Myosin7a, vGlut3, Espin, PMCAs, Ribeye, conjugated-phalloidin, Atoh1, Pou4f3, etc). Hair cell differentiation level can also be assessed by Western Blot for Myosin7a, vGlut3, Espin, PMCAs, Prestin, Ribeye, Atoh1, Pou4f3.

"Stem Cell Assay" as used herein is an assay in which a cell or a cell population are tested for a series of criteria to determine whether the cell or cell population are stem cells or enriched in stem cells or stem cell markers. In a stem cell assay, the cell/cell population are tested for stem cell characteristics such as expression of Stem Cell Markers, and further optionally are tested for stem cell function, including the capacity of self-renewal and differentiation.

"Stem Cell Proliferator" as used herein is a compound that induces an increase in a population of cells which have the capacity for self-renewal and differentiation.

"Stem Cell Proliferation Assay" as used herein is an assay to determine the capacity for agent(s) to induce the creation of stem cells from a starting cell population. In an exemplary Stem Cell Proliferation Assay, the number of cells for an initial cell population is harvested from a Lgr5-GFP mouse such as a B6.129P2-Lgr5tm1(cre/ERT2)Cle/J mouse (also known as Lgr5-EGFP-IRES-creERT2 or Lgr5-GFP mouse, Jackson Lab Stock No: 008875) between the age of 3 to 7 days, by isolating the Organ of Corti sensory epithelium and dissociating the epithelium into single cells. Approximately 5000 cells are entrapped in 40 µl of culture substrate (for example: Matrigel (Corning, Growth Factor Reduced)) and placed at the center of wells in a 24-well plate with 500 µl of an appropriate culture media, growth factors and agent being tested. Appropriate culture media and growth factors include Advanced DMEM/F12 with media Supplements (1×N2, 1×B27, 2 mM Glutamax, 10 mM HEPES, 1 mM N-acetylcysteine, and 100 U/ml Penicillin/100 µg/ml Streptomycin) and growth factors (50 ng/ml EGF, 50 ng/ml bFGF, and 50 ng/ml IGF-1) as well as the agent(s) being assessed are added into each well. Cells are cultured for 10 days in a standard cell culture incubator at 37° C. and 5% $CO_2$, with media change every 2 days. The number of $Lgr5^+$ cells is quantified by counting the number of cells identified as Lgr5+ in an In Vitro Lgr5 activity assay. The fraction of cells that are $Lgr5^+$ is quantified by dividing the number of cells identified as $Lgr5^+$ in a cell population by the total number of cells present in the cell population. The average $Lgr5^+$ activity of a population is quantified by measuring the average mRNA expression level of Lgr5 of the population normalized using suitable and unregulated references or housekeeping genes (e.g., Hprt). The number of hair cells in a population may be measured by staining with hair cell marker (e.g., MyosinVIIa), or using an endogenous reporter of hair cell genes (eg. Pou4f3-GFP, Atoh1-nGFP) and analyzing using flow cytometry. The fraction of cells that are hair cells is quantified by dividing the number of cells identified as hair cells in a cell population by the total number of cells present in the cell population. Lgr5 activity can be measured by qPCR.

"Stem Cell Markers" as used herein can be defined as gene products (e.g. protein, RNA, etc) that specifically expressed in stem cells. One type of stem cell marker is gene products that are directly and specifically support the maintenance of stem cell identity. Examples include Lgr5 and Sox2. Additional stem cell markers can be identified using assays that were described in the literatures. To determine whether a gene is required for maintenance of stem cell identity, gain-of-function and loss-of-function studies can be used. In gain-of-function studies, over expression of specific gene product (the stem cell marker) would help maintain the stem cell identity. While in loss-of-function studies, removal of the stem cell marker would cause loss of the stem cell identity or induced the differentiation of stem cells. Another type of stem cell marker is gene that only expressed in stem cells but does not necessary to have specific function to maintain the identity of stem cells. This type of markers can be identified by comparing the gene expression signature of sorted stem cells and non-stem cells by assays such as micro-array and qPCR. This type of stem cell marker can be found in the literature. (e.g. Liu Q. et al., *Int J Biochem Cell Biol*. 2015 March; 60:99-111. http://www.ncbi.nlm.nih.gov/pubmed/25582750). Potential stem cell markers include Ccdc121, Gdf10, Opcm1, Phex, etc. The expression of stem cell markers such as Lgr5 or Sox2 in a given cell or cell population can be measure using assays such as qPCR, immunohistochemistry, western blot, and RNA hybridization. The expression of stem cell markers can also be measured using transgenic cells express reporters which can indicate the expression of the given stem cell markers, e.g. Lgr5-GFP or Sox2-GFP. Flow cytometry analysis can then be used to measure the activity of reporter expression. Fluorescence microscopy can also be used to directly visualize the expression of reporters. The expression of stem cell markers may further be determined using microarray analysis for global gene expression profile analysis. The gene expression profile of a given cell population or purified cell population can be compared with the gene expression profile of the stem cell to determine similarity between the 2 cell populations. Stem cell function can be measured by colony forming assay or sphere forming assay, self-renewal assay and differentiation assay. In colony (or sphere) forming assay, when cultured in appropriate culture media, the stem cell should be able to form colonies, on cell culture surface (e.g. cell culture dish) or embedded in cell culture substrate (e.g. Matrigel) or be able to form spheres when cultured in suspension. In colony/sphere forming assay, single stem cells are seeded at low cell density in appropriate culture media and allowed to proliferate for a given period of time (7-10 days). Colony formed are then counted and scored for stem cell marker expression as an indicator of stemness of the original cell. Optionally, the colonies that formed are then picked and passaged to test its self-renewal and differentiation potential. In self-renewal assay, when cultured in appropriate culture media, the cells should maintain stem cell marker (e.g. Lgr5) expression over at least one (e.g. 1, 2, 3, 4, 5, 10, 20, etc) cell divisions. In a Stem Cell Differentiation Assay, when cultured in appropriate differentiation media, the cells should be able to generate hair cell which can be identified by hair cell marker expression measured by qPCR, immunostaining, western blot, RNA hybridization or flow cytometry.

"Stemness Driver" as used herein is a composition that induces proliferation of LGR5$^+$ cells, upregulates Lgr5 in cells, or maintains Lgr5 expression in cells, while maintaining the potential for self-renewal and the potential to differentiate into hair cells. Generally, stemness drivers upregulate at least one biomarker of post-natal stem cells. Stemness Drivers include but are not limited to Wnt agonists and GSK3 inhibitors.

"Subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

"Supporting Cell" as used herein in connection with a cochlear epithelium comprises epithelial cells within the organ of Corti that are not hair cells. This includes inner pillar cells, outer pillar cells, inner phalangeal cells, Deiter cells, Hensen cells, Boettcher cells, and/or Claudius cells.

"Synergy" or "synergistic effect" is an effect which is greater than the sum of each of the effects taken separately; a greater than additive effect.

"TGF Beta inhibitor" as used herein is a composition that reduces activity of TgfBeta "Tissue" is an ensemble of similar cells from the same origin that together carry out a specific function including, for example, tissue of cochlear, such as the Organ of Corti.

"Transtympanic" administration refers to direct injection of a composition across the tympanic membrane into the middle ear.

"Treating" as used herein in connection with a cell population means delivering a substance to the population to effect an outcome. In the case of in vitro populations, the substance may be directly (or even indirectly) delivered to the population. In the case of in vivo populations, the substance may be delivered by administration to the host subject.

"Wnt activation" as used herein is an activation of the Wnt signaling pathway.

The term "alkyl" as used herein refers to a straight or branched saturated hydrocarbon. For example, an alkyl group can have 1 to 8 carbon atoms (i.e., ($C_1$-$C_8$)alkyl) or 1 to 6 carbon atoms (i.e., ($C_1$-$C_6$ alkyl) or 1 to 4 carbon atoms.

The term "alkenyl" as used herein refers to a linear or branched hydrocarbon radical which includes one or more double bonds and can include divalent radicals, having from 2 to about 15 carbon atoms. Examples of alkenyl groups include but are not limited to, ethenyl, propenyl, butenyl, and higher homologs and isomers.

The term "alkynyl" as used herein refers to a linear or branched hydrocarbon radical which includes one or more triple bonds and can include divalent radicals, having from 2 to about 15 carbon atoms. Examples of alkynyl groups include but are not limited to, ethynyl, propynyl, butynyl, and higher homologs and isomers.

The term "halo" or "halogen" as used herein refers to fluoro, chloro, bromo and iodo.

The term "aryl" as used herein refers to a single all carbon aromatic ring or a multiple condensed all carbon ring system wherein at least one of the rings is aromatic. For example, an aryl group can have 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems may be optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring.

The term "heteroaryl" as used herein refers to a single aromatic ring that has at least one atom other than carbon in the ring, wherein the atom is selected from the group consisting of oxygen, nitrogen and sulfur; the term also includes multiple condensed ring systems that have at least one such aromatic ring, which multiple condensed ring systems are further described below. Thus, the term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. The term also includes multiple condensed ring systems (e.g., ring systems comprising 2, 3 or 4 rings) wherein a heteroaryl group, as defined above, can be condensed with one or more rings selected from heteroaryls (to form for example a naphthyridinyl such as 1,8-naphthyridinyl), heterocycles, (to form for example a 1,2,3,4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system and at any suitable atom of the multiple condensed ring system including a carbon atom and heteroatom (e.g., a nitrogen).

The term "cycloalkyl" as used herein refers to a saturated or partially saturated ring structure having about 3 to about 8 ring members that has only carbon atoms as ring atoms and can include divalent radicals. Examples of cycloalkyl groups include but are not limited to, cyclopropyl, cyclobutyl, cyclopentyl, cyclohexyl, cyclohexene, cyclopentenyl, cyclohexenyl.

The terms "heterocyclyl" or "heterocyclic" refer to monocyclic or polycyclic 3 to 24-membered rings containing carbon and heteroatoms selected from oxygen, phosphorous, nitrogen, or sulfur and wherein there are no delocalized π electrons (aromaticity) shared among the ring carbon or heteroatoms. Examples of heterocyclyl include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. Examples of heterocyclyl also include, but are not limited to, fused rings, bridged rings (e.g., 2,5-diazabicyclo[2,2,1]heptane), and spirocyclic rings, (e.g., 2,8-diazaspiro[4,5]decane).

The use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid,/toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. For example, inorganic salts include, but are not limited to, ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Example organic bases used in certain embodiments include isopropylamine, diethylamine, ethanolamine, trimethylamine, dicyclohexylamine, choline and caffeine.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compounds or compositions described herein can be formulated in any manner suitable for a desired delivery route, e.g., transtympanic injection, transtympanic wicks and catheters, and injectable depots. Typically, formulations include all physiologically acceptable compositions including derivatives or prodrugs, solvates, stereoisomers, racemates, or tautomers thereof with any physiologically acceptable carriers, diluents, and/or excipients.

DETAILED DESCRIPTION OF THE INVENTION

Figure 1:
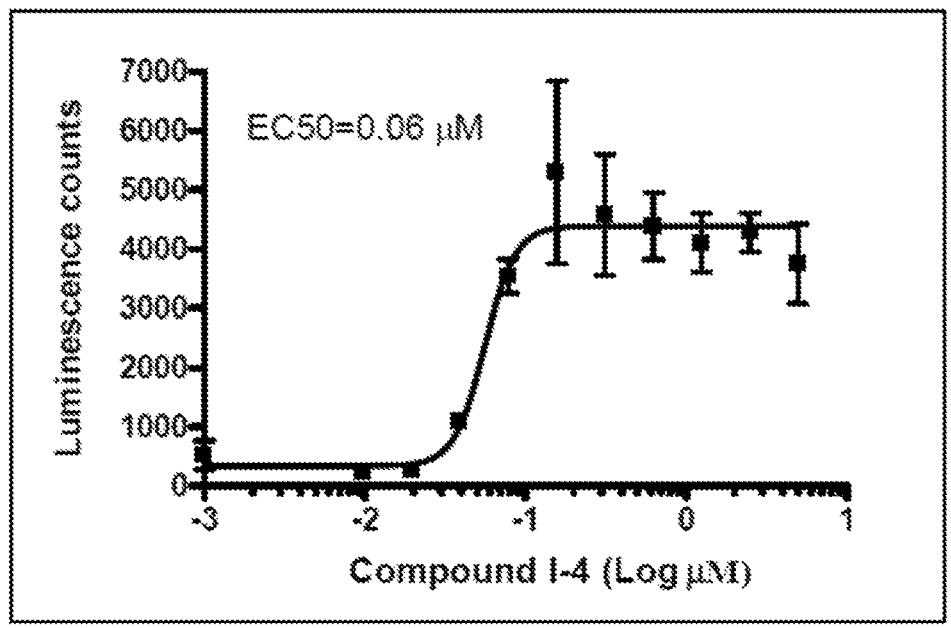
FIG. 1 is a diagram showing the activity of Compound I-4 in the assay performed using TCF/LEF reporter-HEK293 Recombinant cell lines.

A description of example embodiments of the invention follows.

Compounds

The present disclosure provides compounds of Formula (I) or (I'):

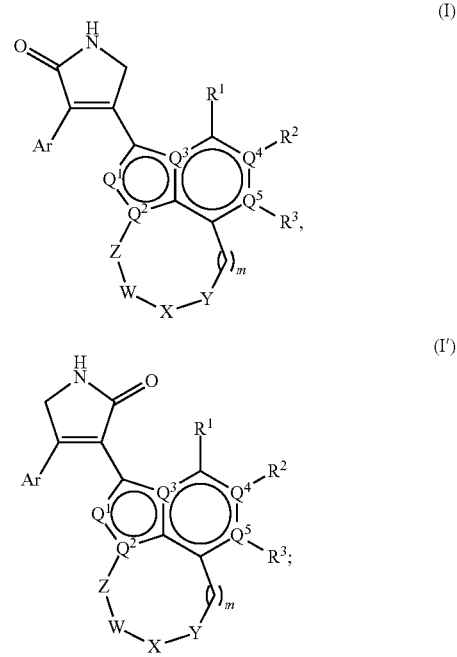

and pharmaceutically acceptable salts and tautomers thereof, wherein $Q^1$, $Q^2$, $Q^3$, $Q^4$, $Q^5$, $R^1$, $R^2$, $R^3$, Ar, —Z—W—X—Y— and m are as defined above for Formula (I).

In certain embodiments, one of $Q^1$, $Q^2$, $Q^3$, $Q^4$, and $Q^5$ is N. In certain embodiments, two of $Q^1$, $Q^2$, $Q^3$, $Q^4$, and $Q^5$ is N. In certain embodiments, $Q^1$ is CH; $Q^2$ is N; $Q^3$ is C; $Q^4$ is C; and $Q^5$ is C. In certain embodiments, $Q^1$ is N; $Q^2$ is C; $Q^3$ is N; $Q^4$ is C; and $Q^5$ is C. In certain embodiments, $Q^1$ is CH; $Q^2$ is C; $Q^3$ is N; $Q^4$ is C; and $Q^5$ is C. In certain embodiments, $Q^1$ is N; $Q^2$ is N; $Q^3$ is C; $Q^4$ is C; and $Q^5$ is C. In certain embodiments, $Q^1$ is CH; $Q^2$ is N; $Q^3$ is C; $Q^4$ is N; and $Q^5$ is C. In certain embodiments, $Q^1$ is CH; $Q^2$ is N; $Q^3$ is C; $Q^4$ is C; and $Q^5$ is N.

In certain embodiments, the

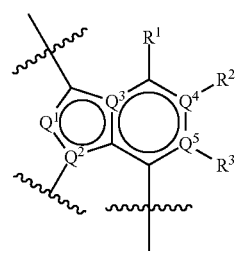

is selected from the group consisting of

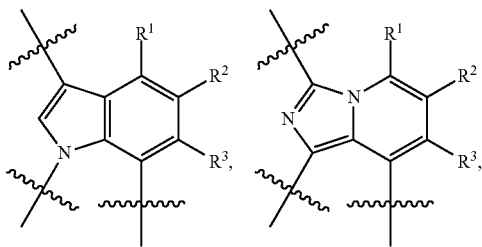

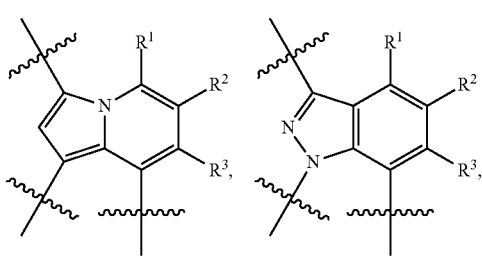

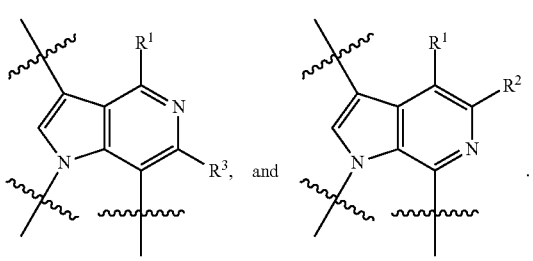

In certain embodiments, $R^1$ is hydrogen or halo. In certain embodiments, $R^1$ is $C_1$-$C_4$alkyl, wherein the alkyl is optionally substituted with one to 3 substituents independently selected from the group consisting of halo and —OH. In certain embodiments, $R^1$ is $C_1$-$C_4$alkynyl, —CN, —OH, or —S(O)$_2$NH$_2$. In certain embodiments, $R^1$ is —NH$_2$ or —NHC(O)$R^{1a}$, wherein $R^{1a}$ is $C_1$-$C_4$alkyl.

In certain embodiments, $R^2$ is hydrogen or halo. In certain embodiments, $R^2$ is $C_1$-$C_4$alkyl, wherein the alkyl is optionally substituted with one to 3 substituents independently selected from the group consisting of halo and —OH. In certain embodiments, $R^2$ is $C_1$-$C_4$alkynyl, —CN, —OH, or —S(O)$_2$NH$_2$. In certain embodiments, $R^2$ is —NH$_2$ or —NHC(O)$R^{2a}$, wherein $R^{2a}$ is $C_1$-$C_4$alkyl. In certain embodiments, $Q^4$ is N and $R^2$ is absent. In certain embodiments, $R^2$ is —S(O)$_2$NH$_2$.

In certain embodiments, $R^2$ is $C_1$-$C_4$alkenyl. In certain embodiments, $R^2$ is —O—$C_1$-$C_4$alkyl. In certain embodiments, $R^2$ is —NH$_2$, —NH($C_1$-$C_4$alkyl), or —N($C_1$-$C_4$alkyl)$_2$.

In certain embodiments, $R^3$ is hydrogen or halo. In certain embodiments, $R^3$ is $C_1$-$C_4$alkyl, wherein the alkyl is optionally substituted with one to 3 substituents independently selected from the group consisting of halo and —OH. In certain embodiments, $R^3$ is $C_1$-$C_4$alkynyl, —CN, —OH, or —S(O)$_2$NH$_2$. In certain embodiments, $R^3$ is —NH$_2$ or —NHC(O)$R^{3a}$, wherein $R^{1a}$ is $C_1$-$C_4$alkyl. In certain embodiments, $Q^5$ is N and $R^3$ is absent.

In certain embodiments, Ar is

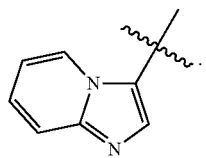

In certain embodiments, Ar is

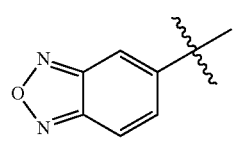

In certain embodiments, Ar is

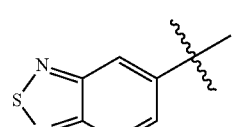

In certain embodiments, Ar is

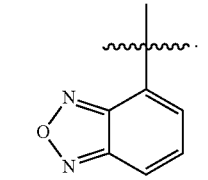

In certain embodiments, Ar is

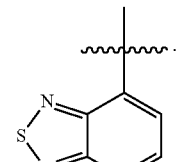

In certain embodiments, In certain embodiments, Ar is

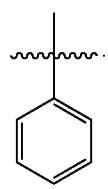

In certain embodiments, Ar is

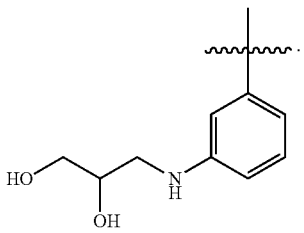 [SMILES: *c1cccc(NCC(O)CO)c1]

In certain embodiments, Ar is

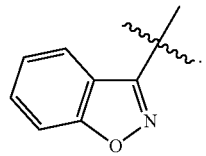 [SMILES: *c1noc2ccccc12]

In certain embodiments, Ar is

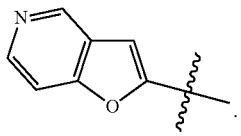 [SMILES: *c1cc2cnccc2o1]

In certain embodiments, Ar is

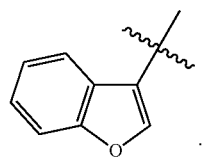 [SMILES: *c1coc2ccccc12]

In certain embodiments, Ar is

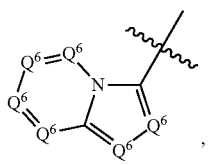

wherein each $Q^6$ is independently selected from $CR^{Q6}$ and N; wherein $R^{Q6}$ is hydrogen, halo, —CN, lower alkyl, or substituted alkyl.

In certain embodiments, Ar is

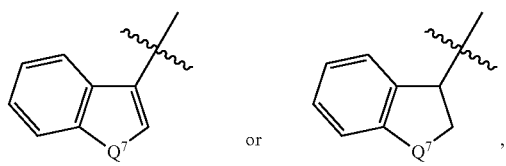

wherein $Q^7$ is selected from S, O, $CH_2$, and $NR^{Q7}$; wherein $R^{Q7}$ is hydrogen or optionally substituted $C_1$-$C_4$alkyl. In certain embodiments, Ar is

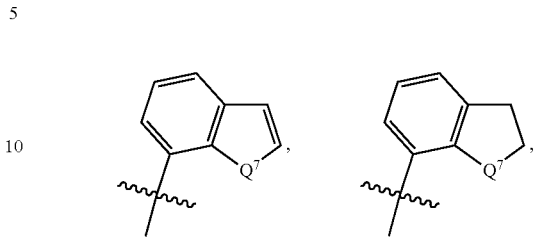

wherein $Q^7$ is selected from S, O, $CH_2$, and $NR^{Q7}$; wherein $R^{Q7}$ is hydrogen or optionally substituted $C_1$-$C_4$alkyl.

In certain embodiments, —Z—W—X—Y— is —C($R^Z$)$_2$—C($R^W$)$_2$—N($R^X$)—C($R^Y$)$_2$—. In certain embodiments, —Z—W—X—Y— is —C($R^Z$)$_2$—C($R^W$)$_2$—CH($R^X$)—C($R^Y$)$_2$—. In certain embodiments, —Z—W—X—Y— is —C($R^W$)$_2$—CH($R^X$)—C($R^Y$)$_2$—.

In certain embodiments, each $R^Z$ is independently selected from the group consisting of hydrogen and halo. In certain embodiments, both $R^Z$ groups together form $C_3$-$C_6$cycloalkyl, such as cyclopropyl, cyclobutyl, cyclopentyl, or cyclohexyl. In certain embodiments, both $R^Z$ groups together form oxo. In certain embodiments, $R^Z$ and $R^W$ together with the carbons to which they are attached form a $C_3$-$C_6$cycloalkyl, such as cyclopropyl, cyclobutyl, cyclopentyl, or cyclohexyl.

In certain embodiments, each $R^W$ is independently selected from the group consisting of hydrogen and halo. In certain embodiments, both $R^W$ groups together form $C_3$-$C_6$cycloalkyl, such as cyclopropyl, cyclobutyl, cyclopentyl, or cyclohexyl. In certain embodiments, both $R^W$ groups together form oxo. In certain embodiments, $R^Z$ and $R^W$ together with the carbons to which they are attached form a $C_3$-$C_6$cycloalkyl, such as cyclopropyl, cyclobutyl, cyclopentyl, or cyclohexyl.

In certain embodiments, each $R^Y$ is independently selected from the group consisting of hydrogen and halo. In certain embodiments, both $R^Y$ groups together form $C_3$-$C_6$cycloalkyl, such as cyclopropyl, cyclobutyl, cyclopentyl, or cyclohexyl. In certain embodiments, both $R^Y$ groups together form oxo.

In certain embodiments, $R^X$ is $R^{X1}$, which is $C_3$-$C_8$cycloalkyl, heteroaryl, or heterocyclic, wherein the heterocyclic is optionally substituted with one to twelve substituents independently selected from the group consisting of deuterium, halo, $C_1$-$C_4$alkyl, —$(CH_2)_p$—OH, —[C($R^{X1a}$)$_2$]$_p$—OH, —[C($R^{X1a}$)$_2$]$_p$—O—$C_1$-$C_4$alkyl, —NHCO$C_1$-$C_4$alkyl, —CONH$C_1$-$C_4$alkyl, —$(CH_2)_p$—NH$_2$, —[C($R^{X1a}$)$_2$]$_p$—NH$_2$, —[C($R^{X1a}$)$_2$]$_p$—NH—$C_1$-$C_4$alkyl, —[C($R^{X1a}$)$_2$]$_p$—N—($C_1$-$C_4$alkyl)$_2$; wherein p is 0, 1, 2, or 3; wherein each $R^{X1a}$ is independently selected from the group consisting of hydrogen, deuterium, halo, —$CF_3$, and $C_1$-$C_4$alkyl, or both $R^{X1a}$ groups together form $C_3$-$C_6$cycloalkyl.

In certain embodiments, $R^X$ is —$COR^{X1}$ or $R^X$ is —$SO_2R^{X1}$.

In certain embodiments, $R^X$ is selected from

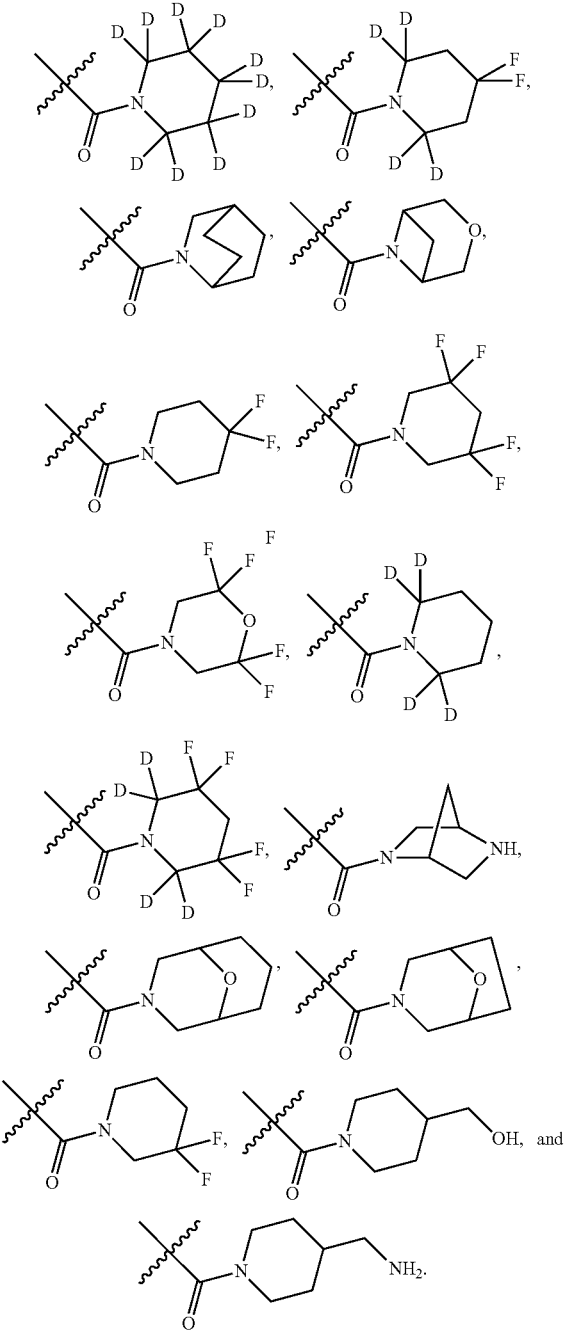
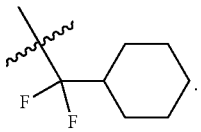 [SMILES: *C(F)(F)C1CCCCC1]

In certain embodiments, $R^{X1}$ is $C_3$-$C_8$cycloalkyl. In certain embodiments, $R^{X1}$ is cyclopropyl, cyclobutyl, cyclopentyl, or cyclohexyl.

In certain embodiments, $R^{X1}$ is heterocyclic, wherein the heterocyclic is optionally substituted with one to twelve substituents that is halo. In certain embodiments, $R^{X1}$ is heterocyclic which is deuterated. In certain embodiments, the heterocyclic is monocyclic or bicyclic. In certain embodiments, the heterocyclic contains one to three nitrogens (i.e., 1, 2, or 3 nitrogens) and/or one to three oxygens (i.e., 1, 2, or 3 oxygens). In certain embodiments, the heterocyclic contains one nitrogen and/or one oxygen. In certain embodiments, the heterocyclic contains one nitrogen. In certain embodiments, the heterocyclic contains two nitrogens. In certain embodiments, the heterocyclic contains one nitrogen and one oxygen.

In certain embodiments, $R^{X1}$ is heterocyclic, wherein the heterocyclic is the heterocyclic is optionally substituted with $C_1$-$C_4$alkyl, —$(CH_2)_p$—OH, or —$(CH_2)_p$—$NH_2$; wherein p is 1, 2, or 3. In certain embodiments, $R^{X1}$ is heterocyclic substituted with $C_1$-$C_4$alkyl. In certain embodiments, $R^{X1}$ is heterocyclic substituted with —$(CH_2)_p$—OH; wherein p is 1, 2, or 3. In certain embodiments, $R^{X1}$ is heterocyclic substituted with —$(CH_2)$—OH. In certain embodiments, $R^{X1}$ is heterocyclic substituted with —$(CH_2)_p$—$NH_2$; wherein p is 1, 2, or 3. In certain embodiments, $R^{X1}$ is heterocyclic substituted with —$(CH_2)$—$NH_2$.

In certain embodiments, $R^{X1}$ is heterocyclic, wherein the heterocyclic is the heterocyclic is optionally substituted with —$[C(R^{X1a})_2]_p$—CN. In certain embodiments, $R^{X1}$ is heterocyclic substituted with —$[C(R^{X1a})_2]_p$—OH, —$[C(R^{X1a})_2]_p$—O—$C_1$-$C_4$alkyl, —$NHCOC_1$-$C_4$alkyl, —$[C(R^{X1a})_2]_p$—$NH_2$, —$[C(R^{X1a})_2]_p$—NH—$C_1$-$C_4$alkyl, or —$[C(R^{X1a})_2]_p$—N—$(C_1$-$C_4$alkyl$)_2$. In certain embodiments, $R^{X1}$ is heterocyclic, wherein the heterocyclic is optionally substituted with —$[C(R^{X1a})_2]_p$—CN, —$[C(R^{X1a})_2]_p$—$NHCOC_1$-$C_4$alkyl, —$[C(R^{X1a})_2]_p$—$N(C_1$-$C_4$alkyl)-$COC_1$-$C_4$alkyl, or —$[C(R^{X1a})_2]_p$—CON—$(C_1$-$C_4$alkyl$)_2$.

In certain embodiments, each $R^{X1a}$ is independently selected from the group consisting of hydrogen and halo. In certain embodiments, both $R^{X1a}$ groups together form $C_3$-$C_6$cycloalkyl, such as cyclopropyl, cyclobutyl, cyclopentyl, or cyclohexyl.

In certain embodiments, $R^{X1}$ is heteroaryl. In certain embodiments, the heteroaryl is monocyclic or bicyclic. In certain embodiments, the heteroaryl contains one to three nitrogens (i.e., 1, 2, or 3 nitrogens) and/or one to three oxygens (i.e., 1, 2, or 3 oxygens). In certain embodiments, the heteroaryl contains one nitrogen and/or one oxygen. In certain embodiments, the heteroaryl contains one nitrogen. In certain embodiments, the heteroaryl contains two nitrogens. In certain embodiments, the heteroaryl contains one nitrogen and one oxygen. In certain embodiments, $R^{X1}$ is In certain embodiments, $R^X$ is —$(C_1$-$C_4$alkylene)-$R^{X1}$, wherein the —$(C_1$-$C_4$alkylene)$R^{X1}$ is optionally substituted with one to four halo on the $C_1$-$C_4$alkylene. In certain embodiments, the —$(C_1$-$C_4$alkylene)-$R^{X1}$ is substituted with one to four halo on the $C_1$-$C_4$alkylene. In certain embodiments, the —$(C_1$-$C_4$alkylene)-$R^{X1}$ is substituted with one or two halo on the $C_1$-$C_4$alkylene. In certain embodiments, $R^X$ is —$(C_1$-$C_4$alkylene)-$R^{X1}$, wherein the —$(C_1$-$C_4$alkylene)-$R^{X1}$ is optionally substituted with one or two halo on the $C_1$-$C_4$alkylene and wherein $R^{X1}$ is cyclopropyl, cyclobutyl, cyclopentyl, or cyclohexyl. In certain embodiments, $R^X$ is

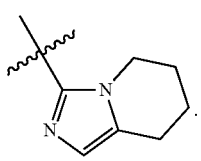 [SMILES: *c1ncc2n1CCCC2]

In certain embodiments, $R^X$ is —$CON(R^{X2})_2$. In certain embodiments, $R^X$ is —$CON(R^{X2})_2$, wherein $R^{X2}$ is hydrogen or methyl. In certain embodiments, $R^X$ is —$CONH_2$. In certain embodiments, $R^X$ is —$CON(R^{X2})_2$, wherein $R^{X2}$ is $C_1$-$C_4$alkyl. In certain embodiments, $R^X$ is —$CON(R^{X2})_2$, wherein $R^{X2}$ is methyl.

In certain embodiments, m is 0. In certain embodiments, m is 1. In certain embodiments, m is 2.

In one variation of Formula (I), Ar is

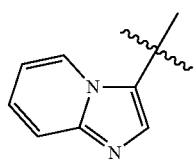 [SMILES: *c1cnc2ccccn12]

and $Q^1$ is CH; $Q^2$ is N; $Q^3$ is C; $Q^4$ is C; and $Q^5$ is C.

The present disclosure provides a compound of Formula (I) or (I'),

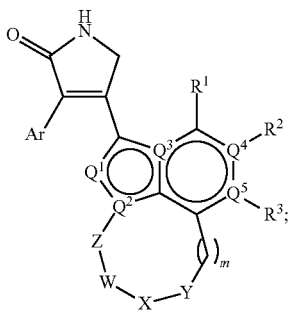
(I)

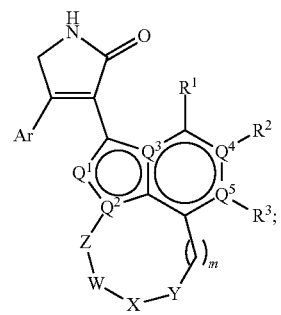
(I')

having one, two, three, or more of the following features:

a) Ar is

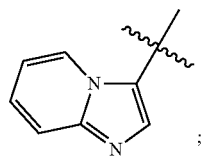 [SMILES: *c1cnc2ccccn12]
;

b) $Q^1$ is CH; $Q^2$ is N; $Q^3$ is C; $Q^4$ is C; and $Q^5$ is C;
c) $R^2$ is hydrogen or halo;
d) —Z—W—X—Y— is —$C(R^Z)_2$—$C(R^W)_2$—$N(R^X)$—$C(R^Y)_2$—;
e) $R^X$ is —$COR^{X1}$.

The present disclosure provides a compound of Formula (I) or (I'),

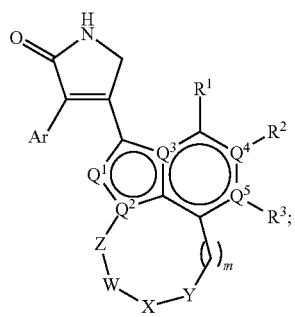
(I)

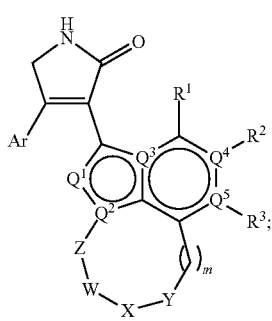
(I')

having one, two, three, or more of the following features:

a) Ar is

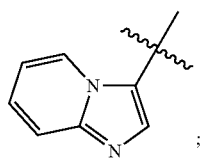 [SMILES: *c1cnc2ccccn12]
;

b) $Q^1$ is CH; $Q^2$ is N; $Q^3$ is C; $Q^4$ is C; and $Q^5$ is C;
c) $R^2$ is $C_1$-$C_4$alkyl, wherein the alkyl is optionally substituted with one to 3 substituents independently selected from the group consisting of halo and —OH;
d) —Z—W—X—Y— is —$C(R^Z)_2$—$C(R^W)_2$—$N(R^X)$—$C(R^Y)_2$—;
e) $R^X$ is —$COR^{X1}$.

The present disclosure provides a compound of Formula (I) or (I'),

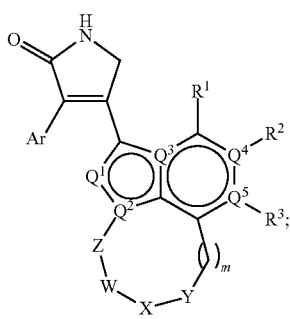
(I)
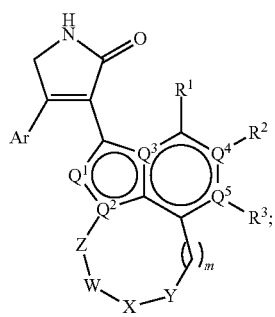
(I')
having one, two, three, or more of the following features:
a) Ar is
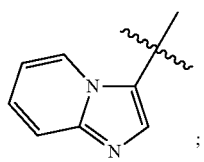 [SMILES: *c1cnc2ccccn12]
b) $Q^1$ is CH; $Q^2$ is N; $Q^3$ is C; $Q^4$ is C; and $Q^5$ is C;
c) $R^2$ is $C_1$-$C_4$alkynyl, —CN, —OH, —S(O)$_2$NH$_2$, —NH$_2$ or —NHC(O)$R^{2a}$;
d) —Z—W—X—Y— is —C($R^Z$)$_2$—C($R^W$)$_2$—N($R^X$)—C($R^Y$)$_2$—;
e) $R^X$ is —COR$^{X1}$.
Nonlimiting examples of compounds of the invention are presented below.
Compound I-1
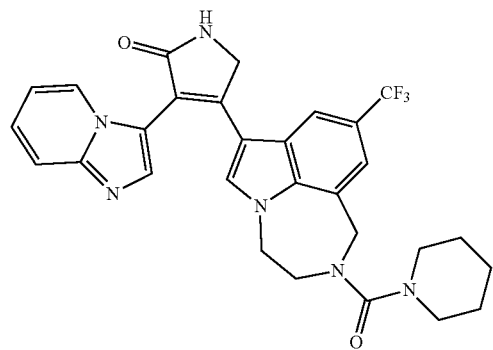
Compound I-2
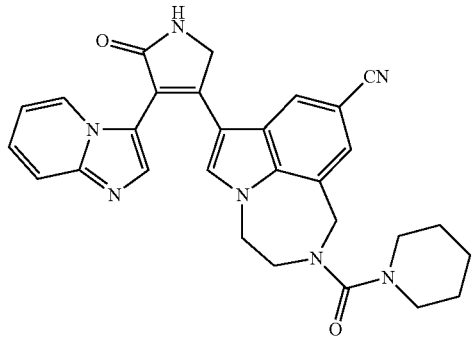
Compound I-3
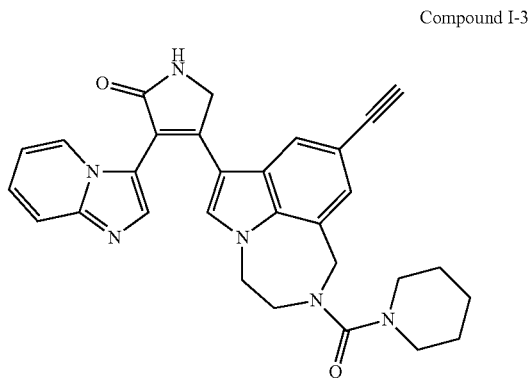
Compound I-4
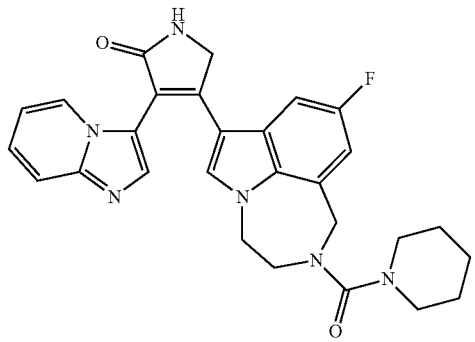
Compound I-5
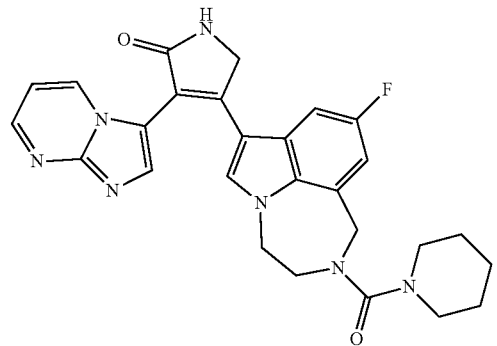

Compound I-6
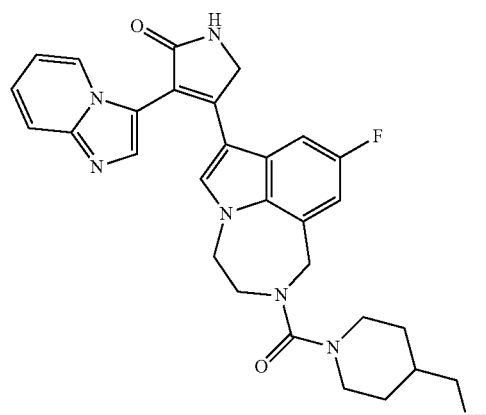
Compound I-7
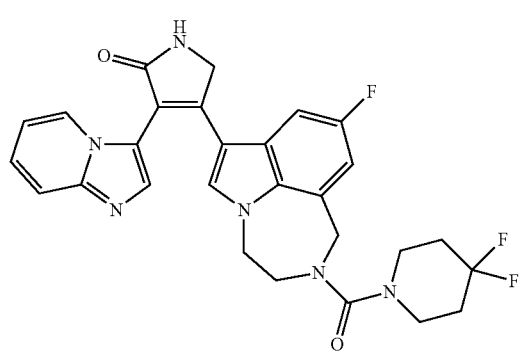
Compound I-8
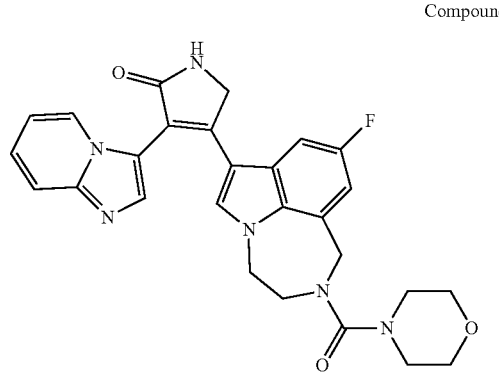
Compound I-9
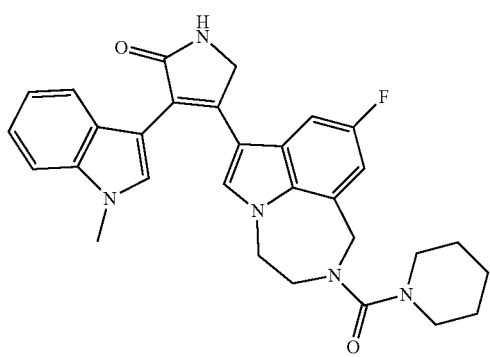
Compound I-10
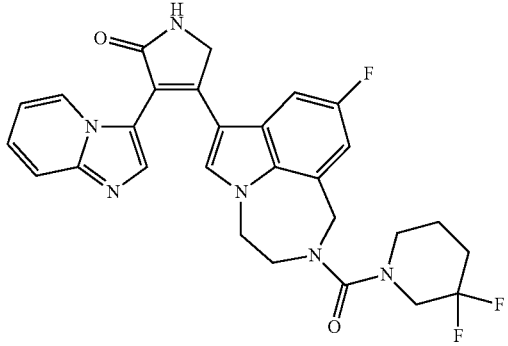
Compound I-11
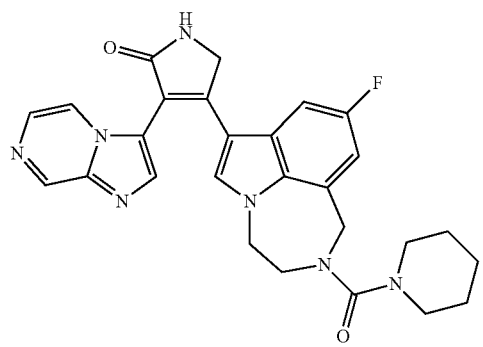
Compound I-12
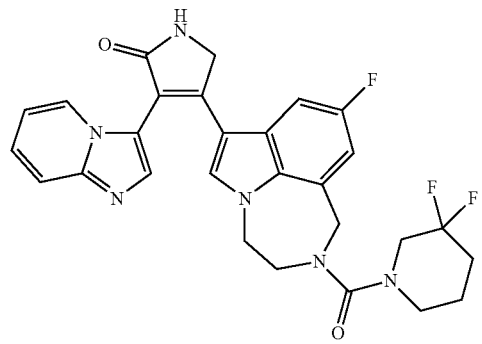
Compound I-13
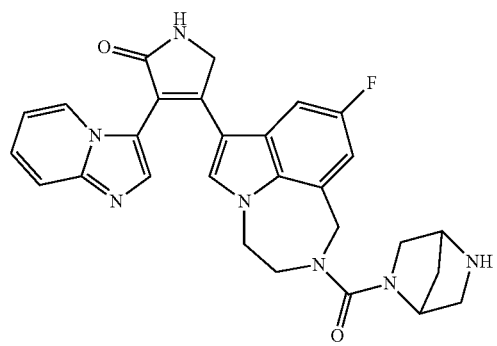

Compound I-14
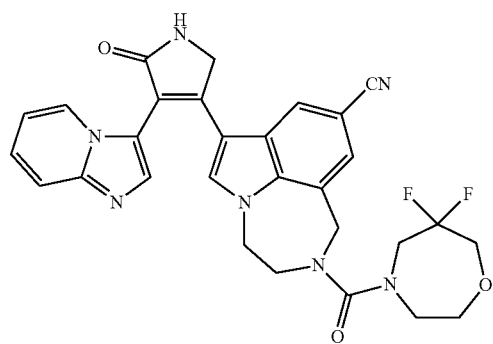
Compound I-15
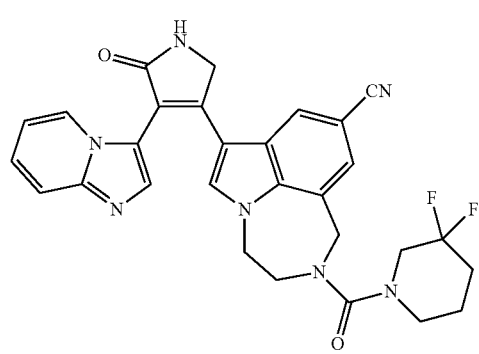
Compound I-16
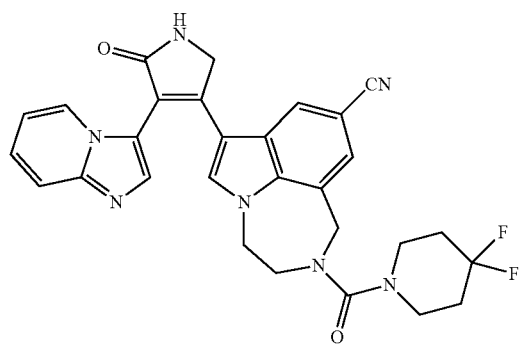
Compound I-17
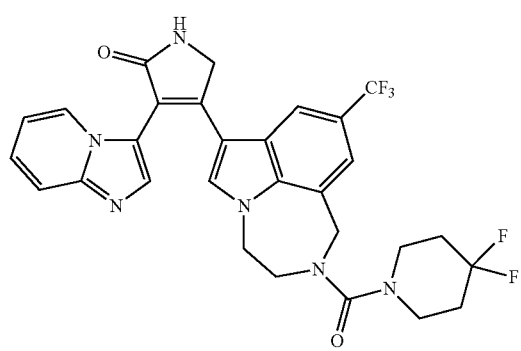
Compound I-18
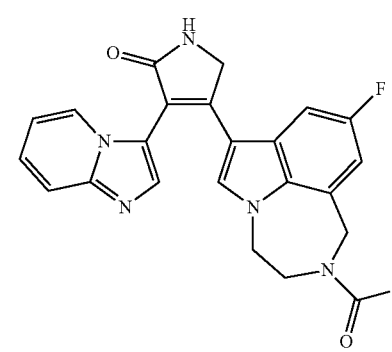
Compound I-19
Compound I-20
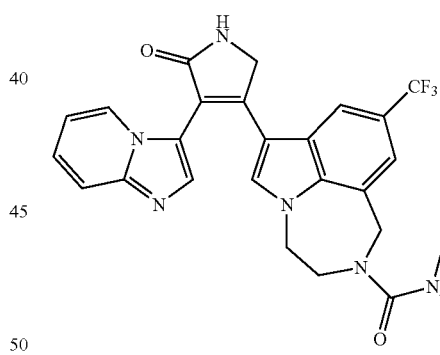
Compound I-21
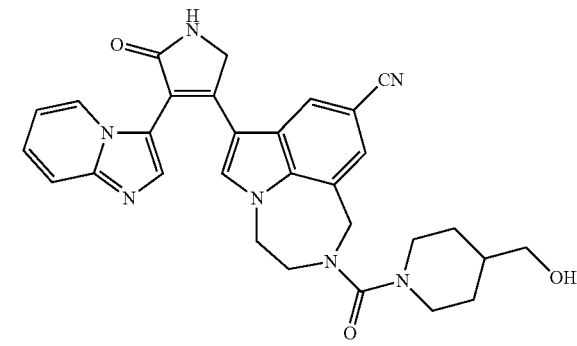

Compound I-22
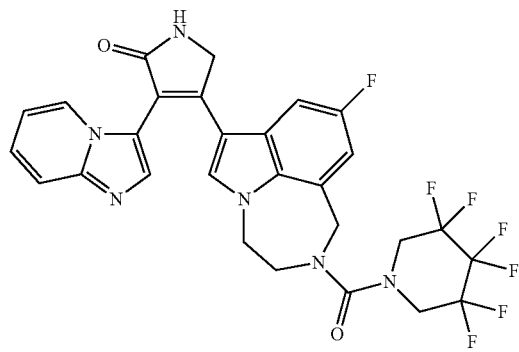
Compound I-23
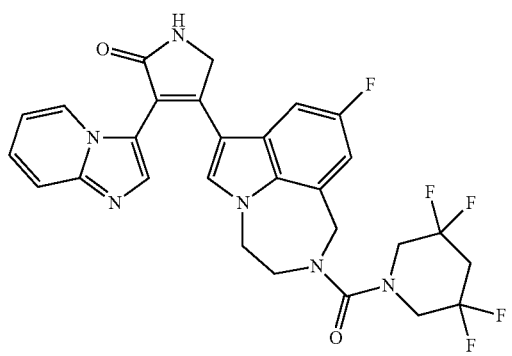
Compound I-24
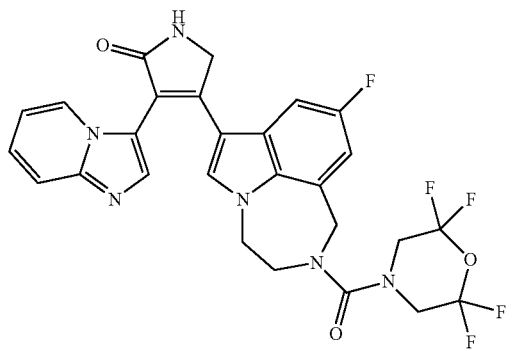
Compound I-25
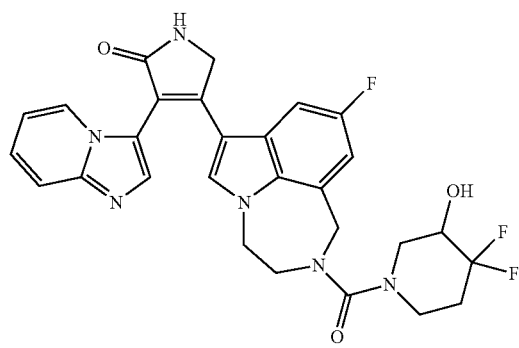
Compound I-26
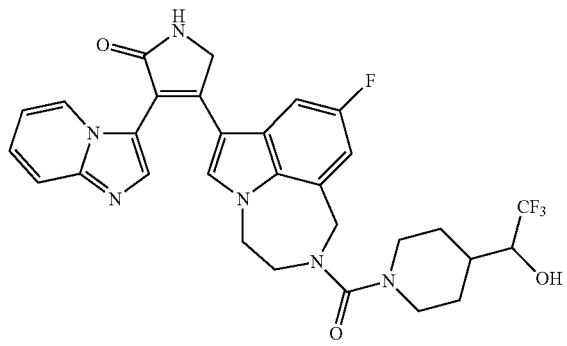
Compound I-27
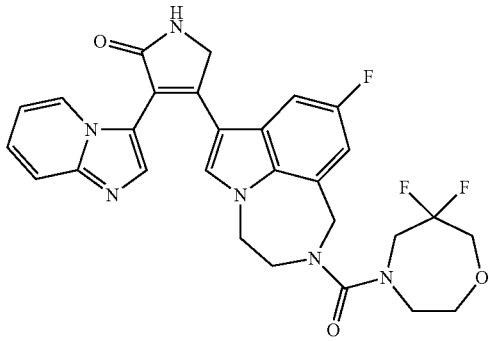
Compound I-28
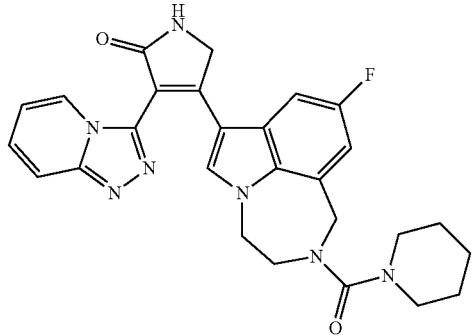
Compound I-29
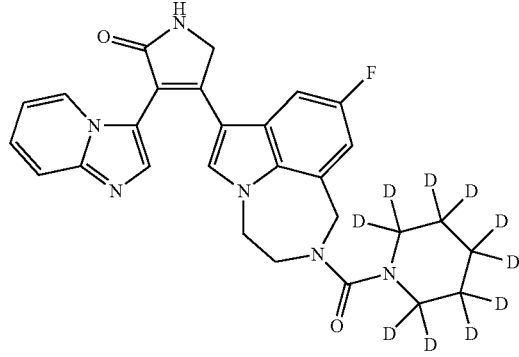

Compound I-30
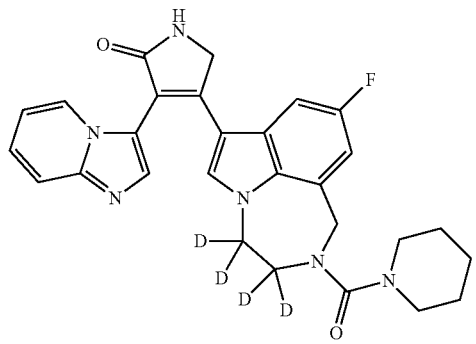
Compound I-34
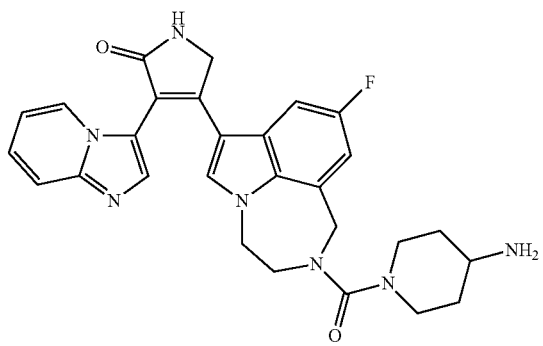
Compound I-31
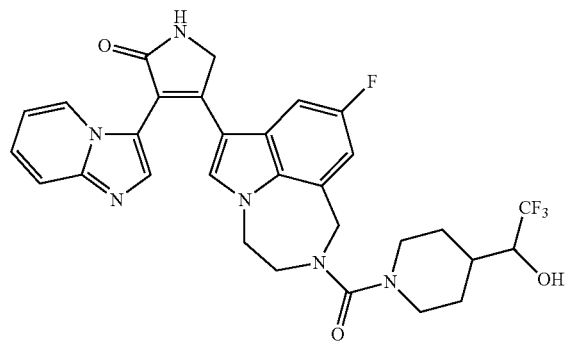
Compound I-35
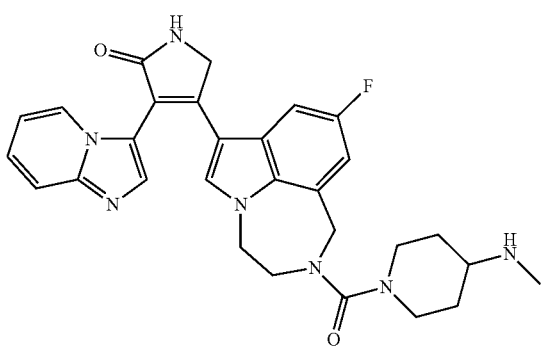
Compound I-32
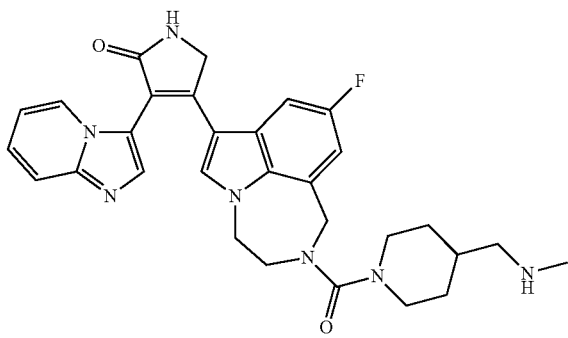
Compound I-36
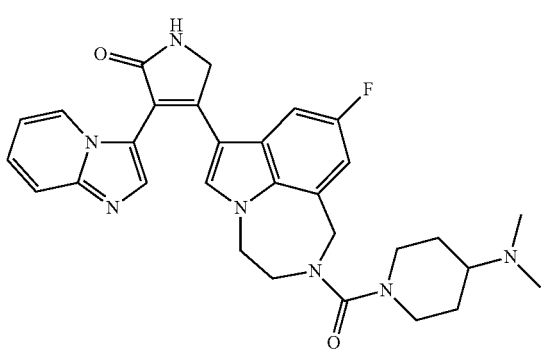
Compound I-33
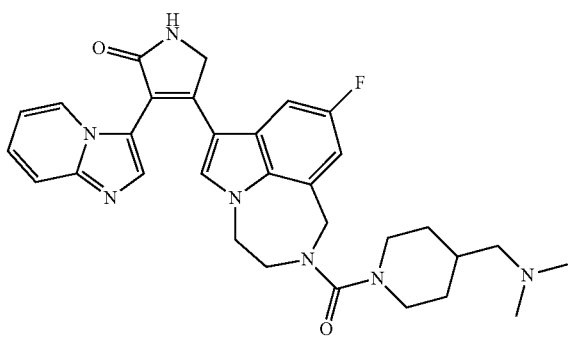
Compound I-37
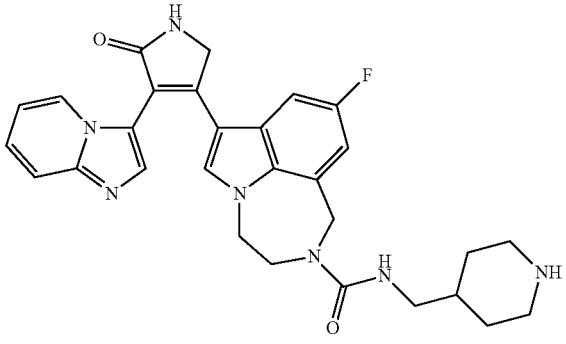

Compound I-38
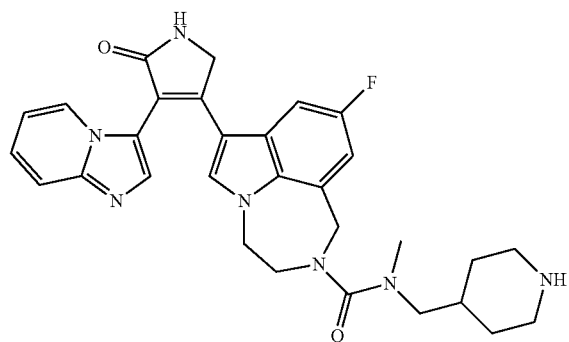
Compound I-42
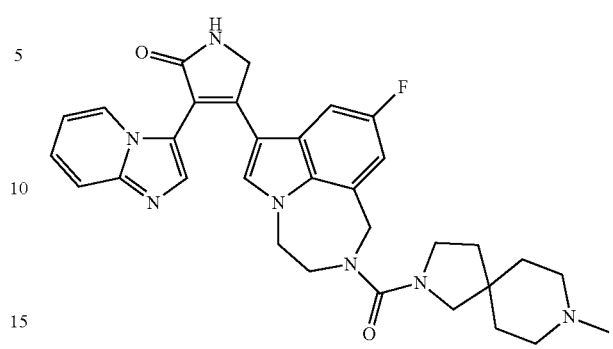
Compound I-39
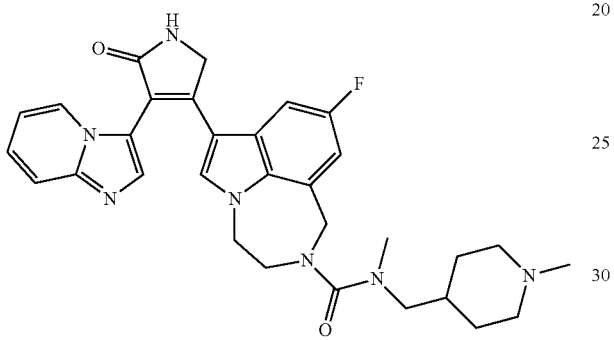
Compound I-43
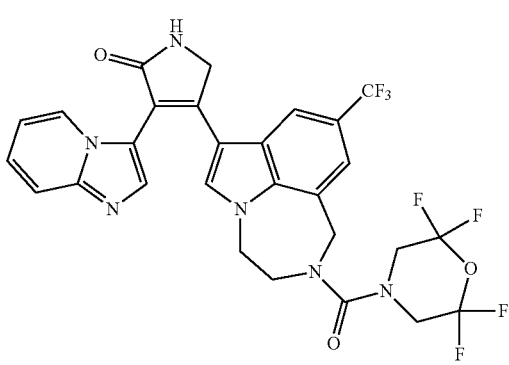
Compound I-40
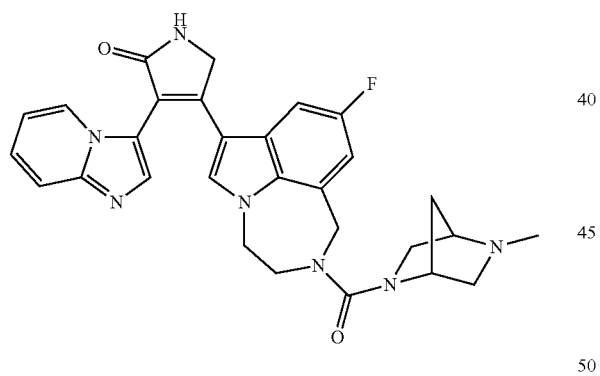
Compound I-44
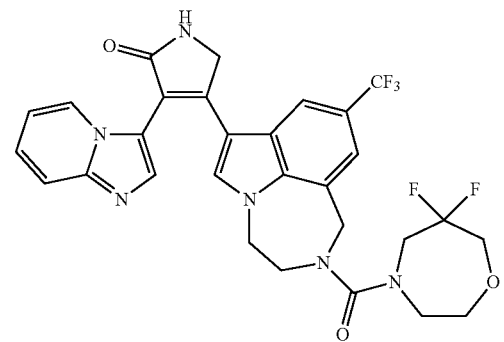
Compound I-41
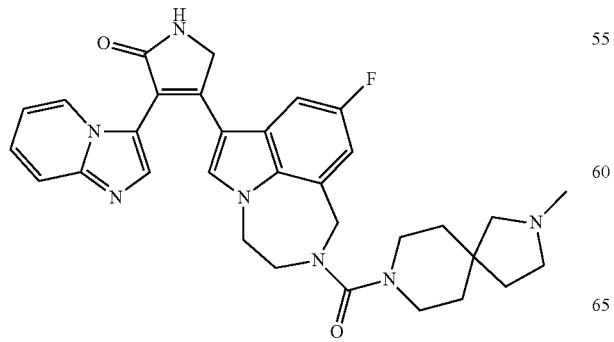
Compound I-45
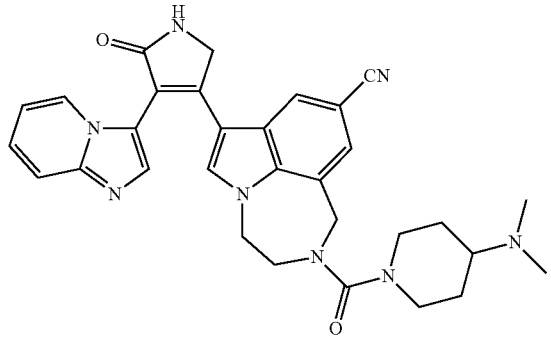

Compound I-46
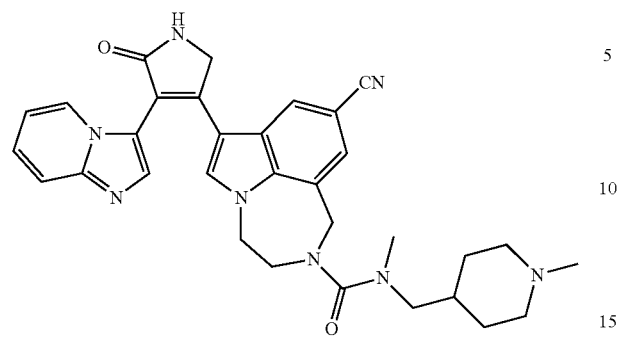
Compound I-50
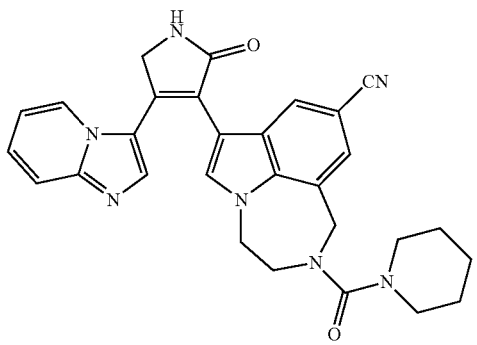
Compound I-47
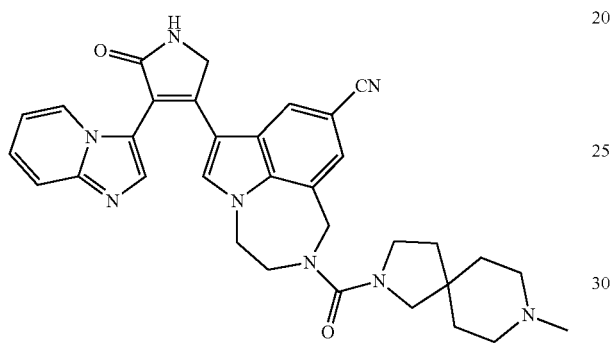
Compound I-51
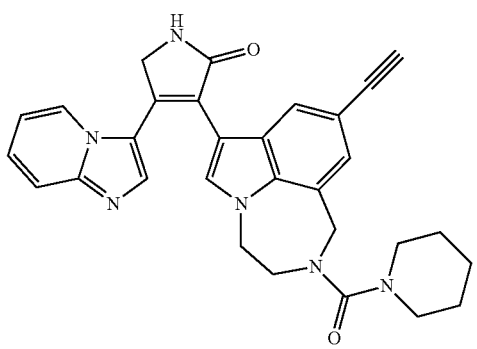
Compound I-48
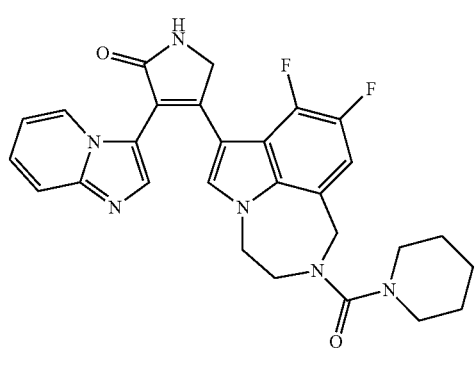
Compound I-52
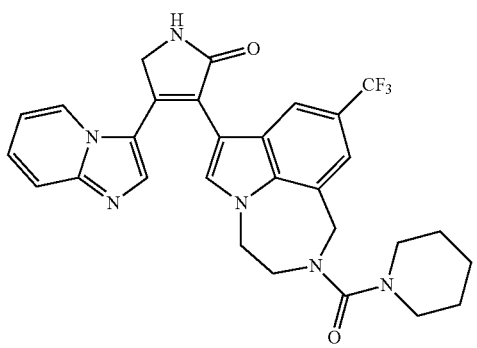
Compound I-49
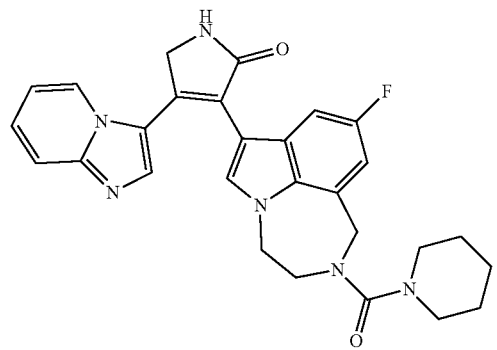
Compound I-53
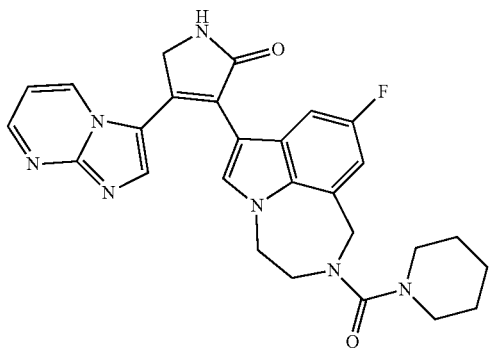

Compound I-54
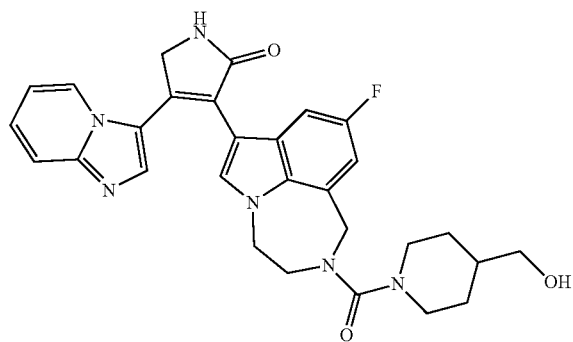
Compound I-58
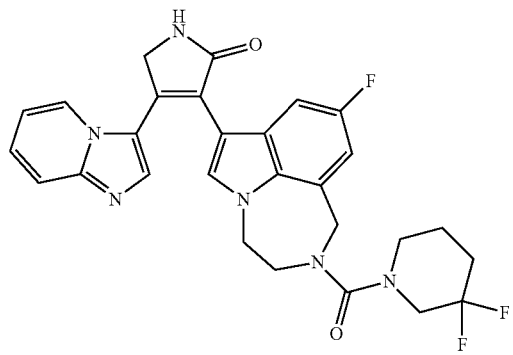
Compound I-55
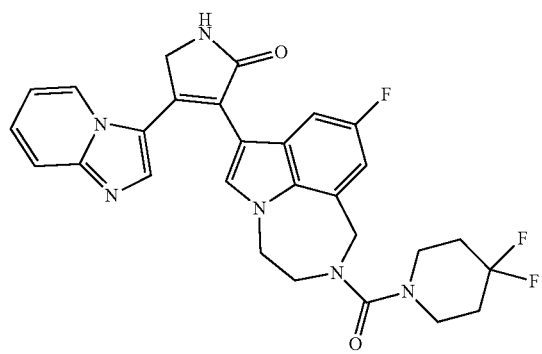
Compound I-59
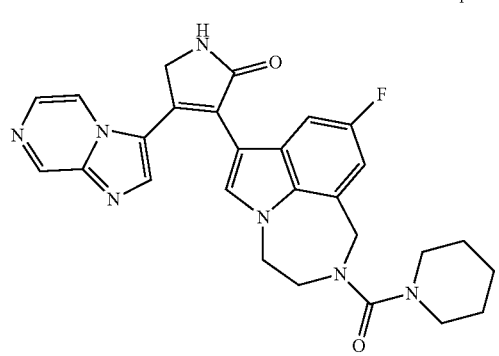
Compound I-56
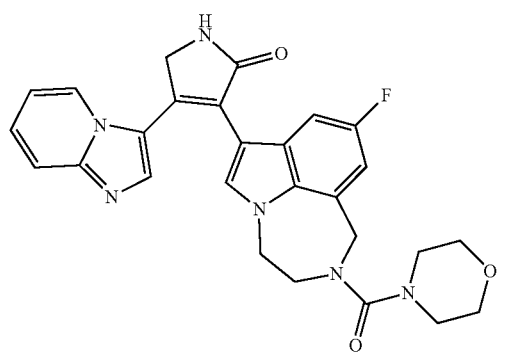
Compound I-60
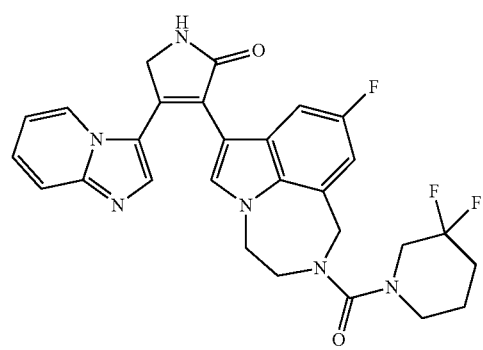
Compound I-57
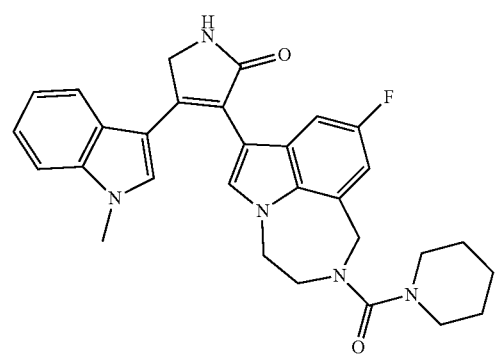
Compound I-61
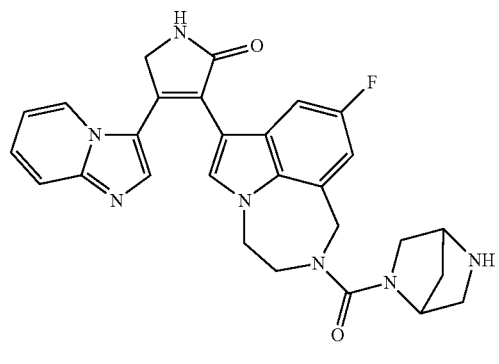

Compound I-62
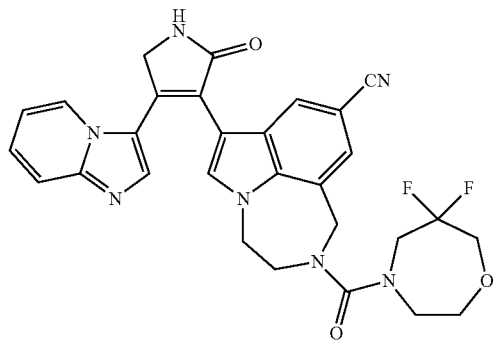
Compound I-66
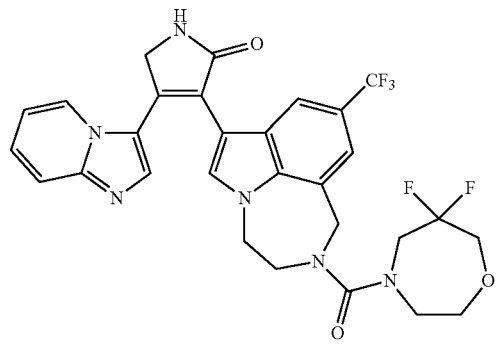
Compound I-63
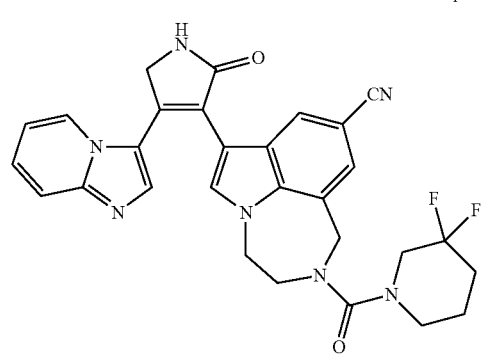
Compound I-67
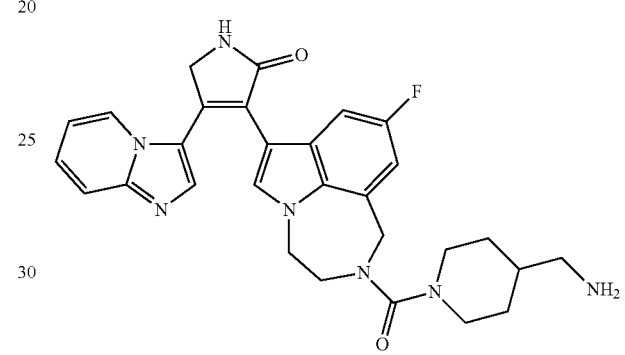
Compound I-64
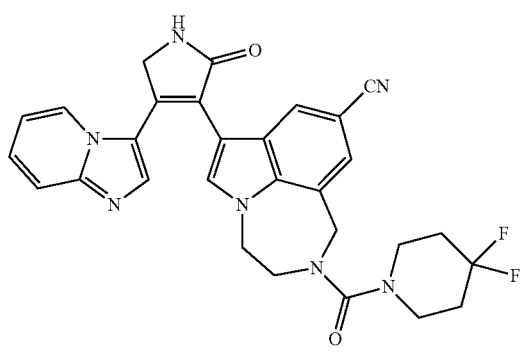
Compound I-68
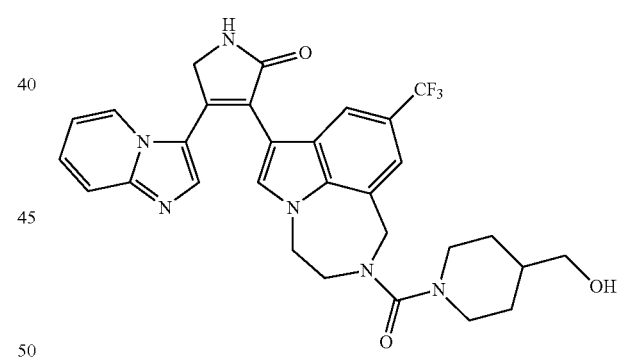
Compound I-65
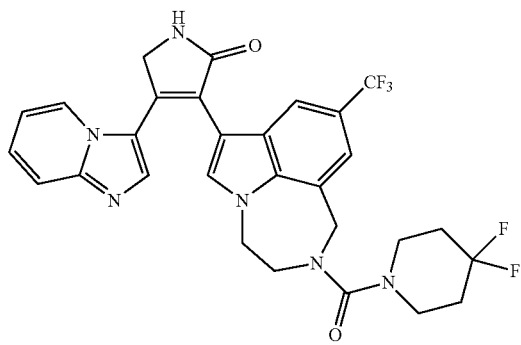
Compound I-69
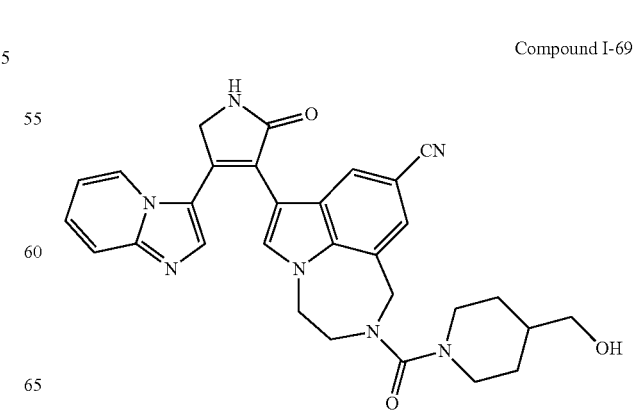

Compound I-70
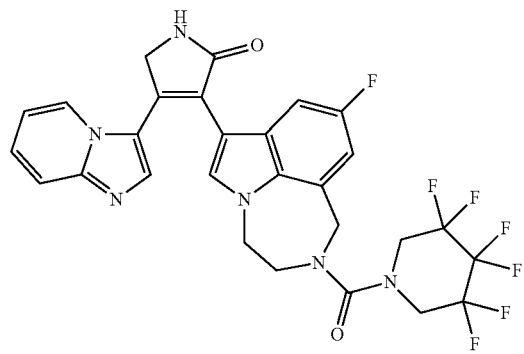
Compound I-74
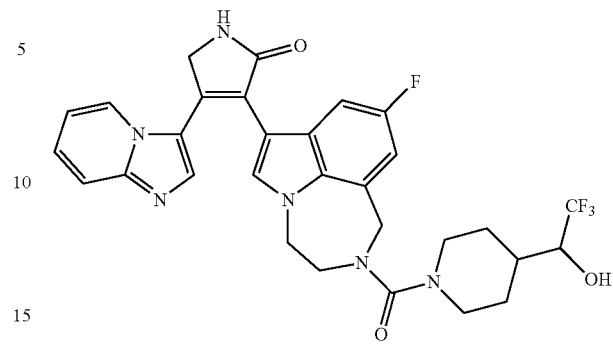
Compound I-71
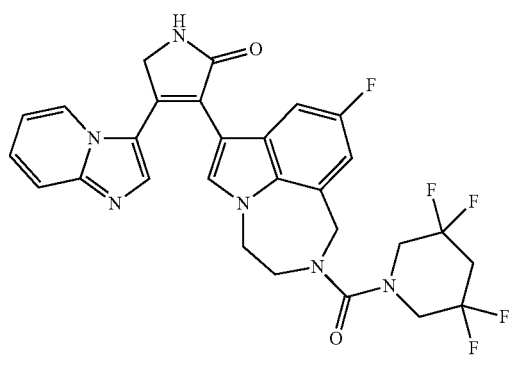
Compound I-75
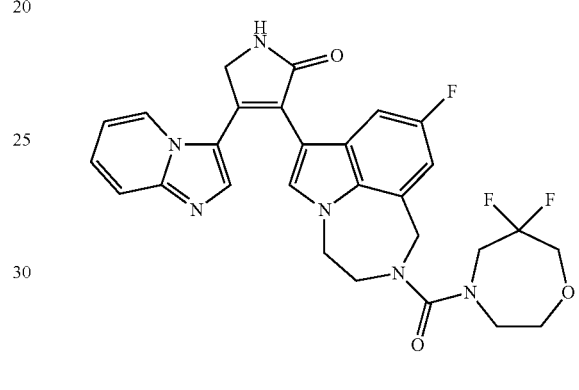
Compound I-72
Compound I-76
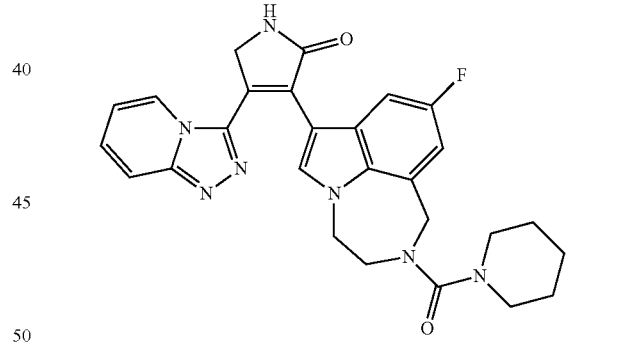
Compound I-73
Compound I-77
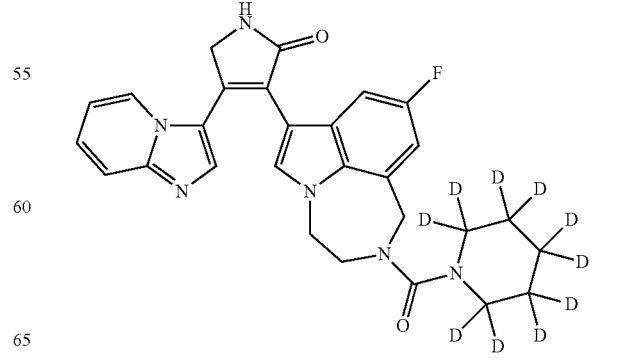

Compound I-78
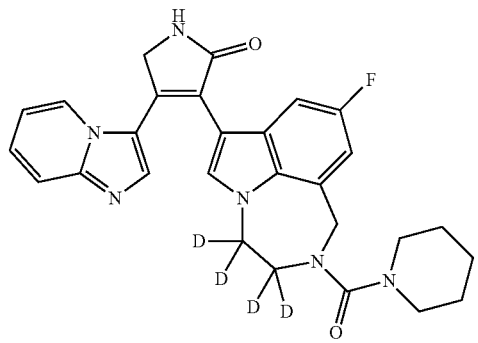
Compound I-82
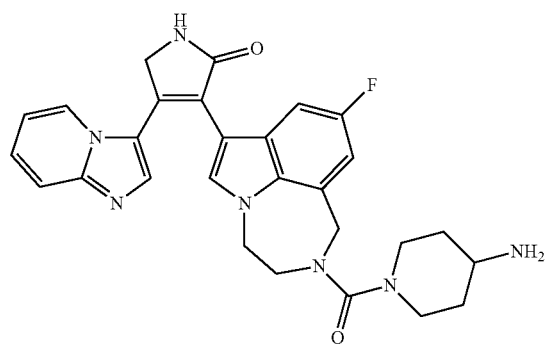
Compound I-79
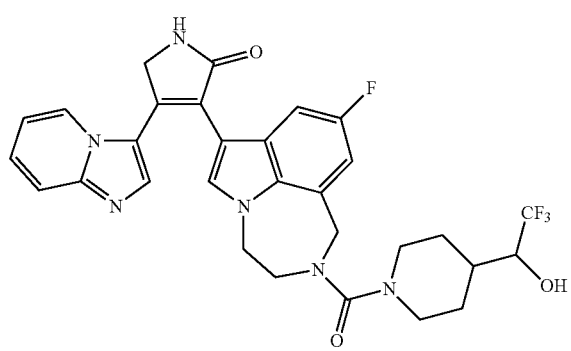
Compound I-83
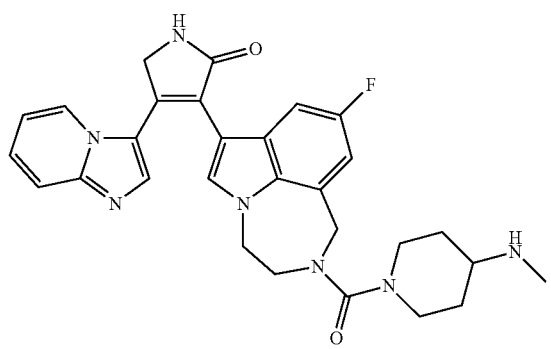
Compound I-80
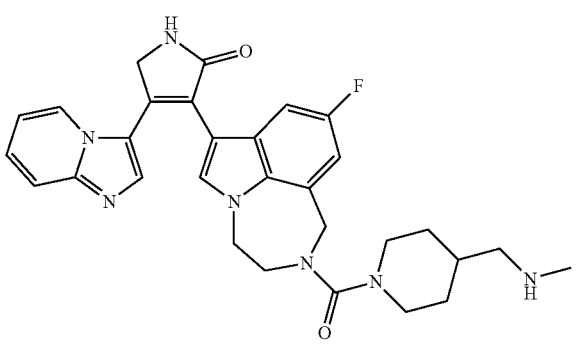
Compound I-84
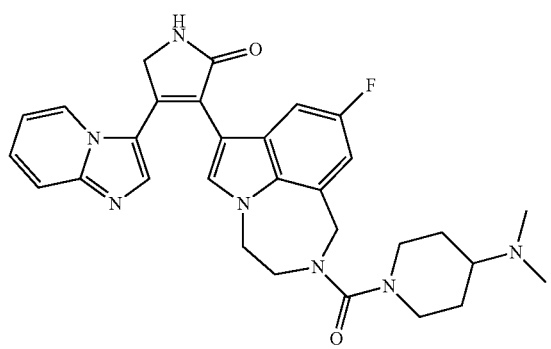
Compound I-81
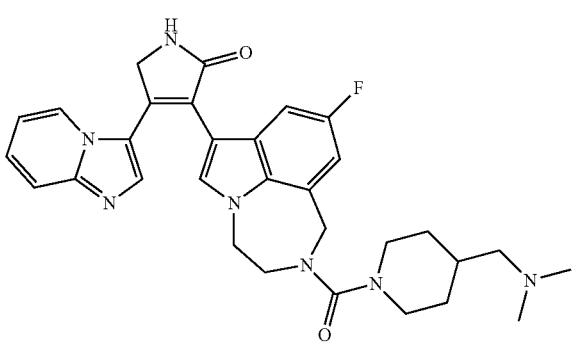
Compound I-85
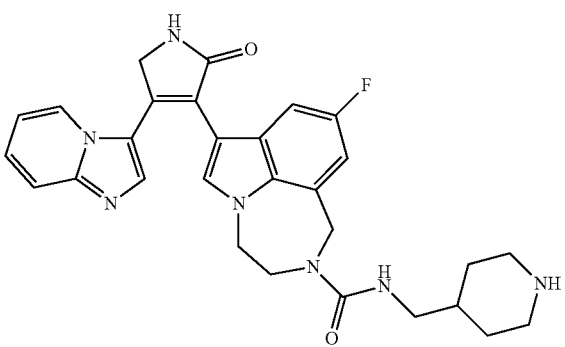

Compound I-86
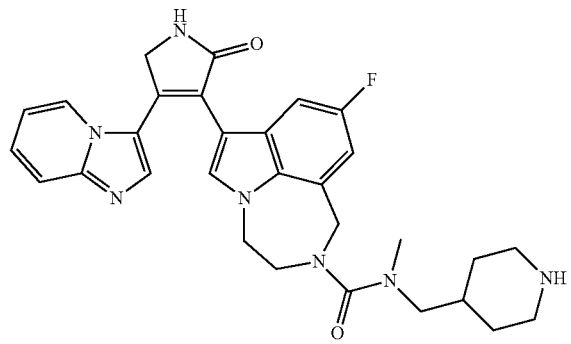
Compound I-90
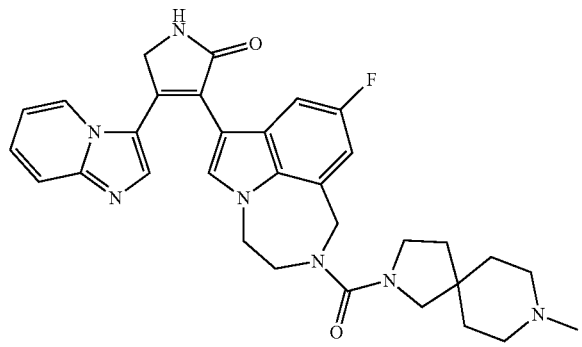
Compound I-87
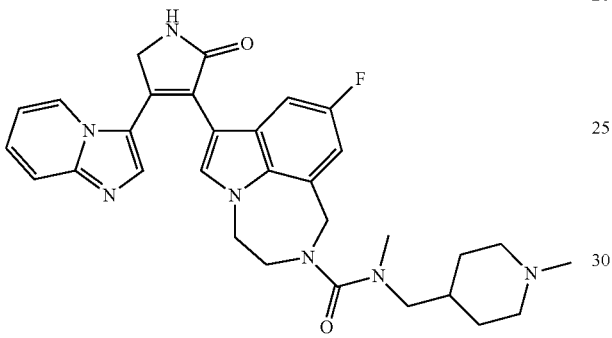
Compound I-91
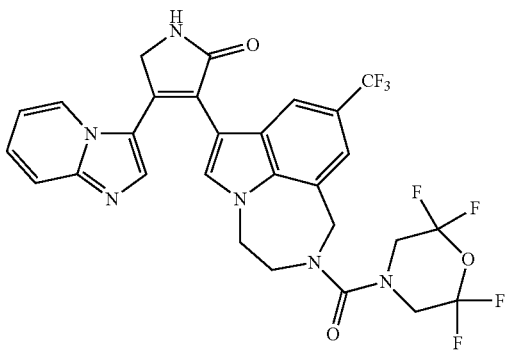
Compound I-88
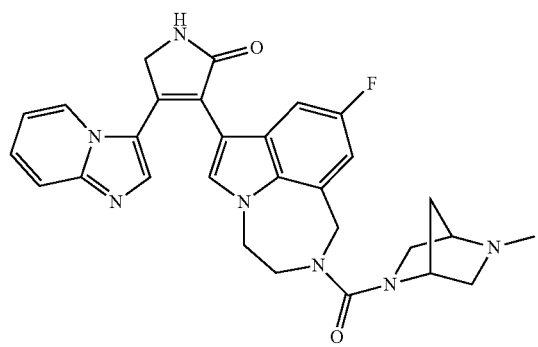
Compound I-92
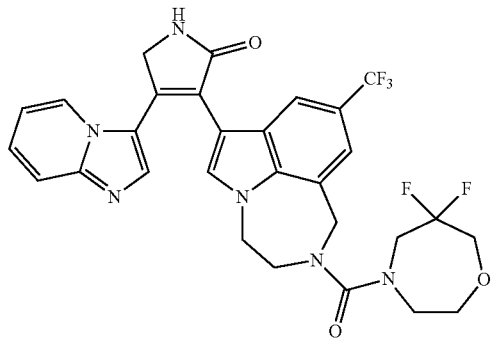
Compound I-89
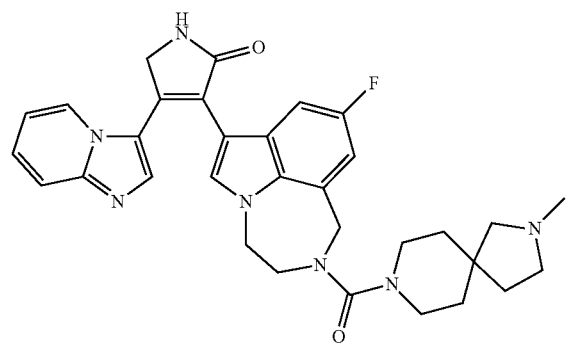
Compound I-93
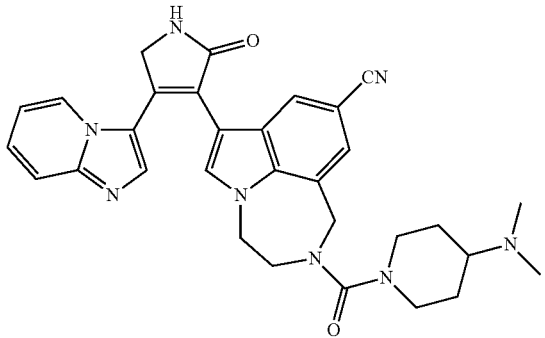

Compound I-94
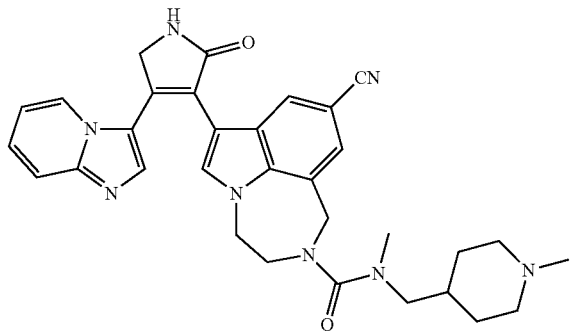
Compound I-95
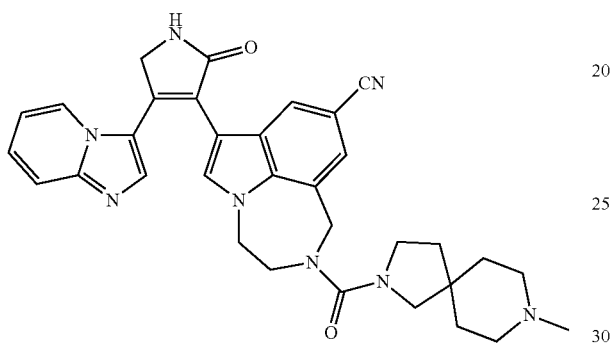
Compound I-96
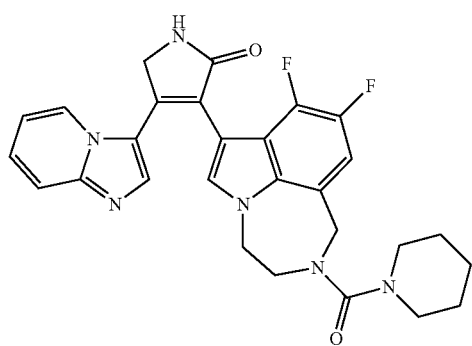
The present disclosure also provides a compound having Formula (IIa) or (IIa'):
(IIa)
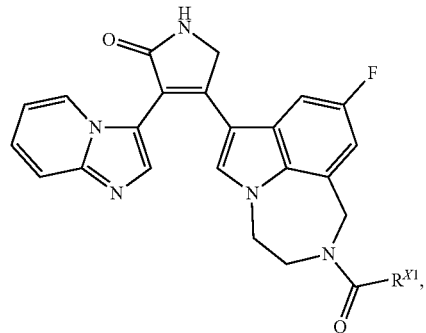
(IIa')
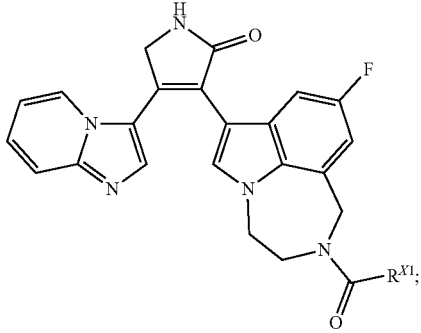
and pharmaceutically acceptable salts and tautomers thereof.
In some embodiments, $R^{X1}$ is selected from the group consisting of:
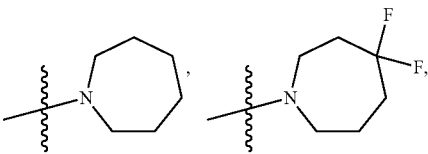
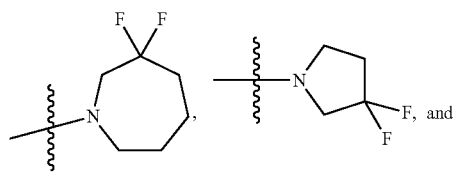
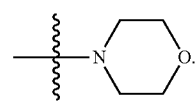
The present disclosure provides a compound having Formula (IIb) or (IIb'):
(IIb)
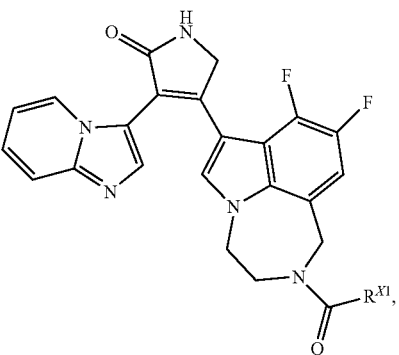

(IIb′)
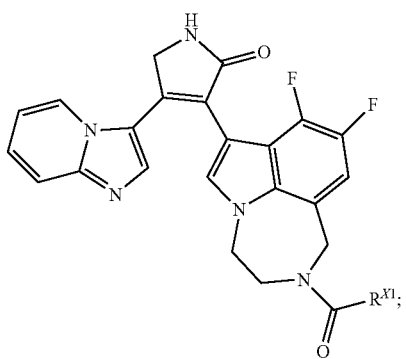
and pharmaceutically acceptable salts and tautomers thereof.
In some embodiments, $R^{X1}$ is selected from the group consisting of:
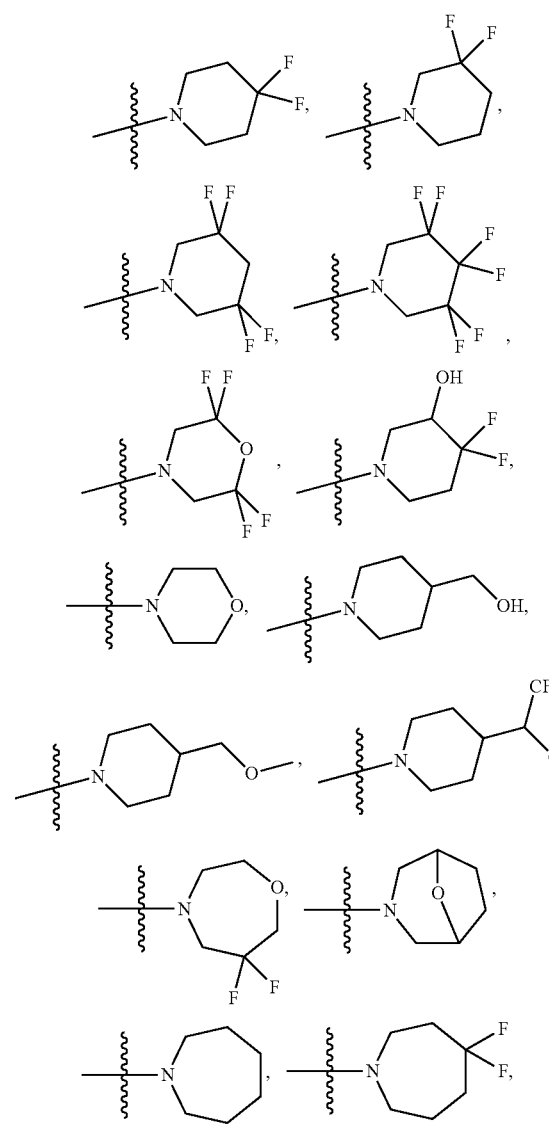
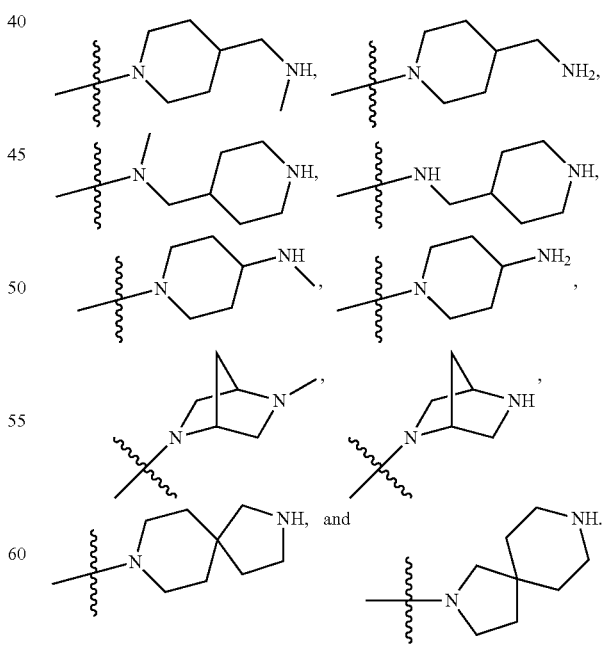
In some embodiments, $R^{X1}$ is selected from the group consisting of:
In some embodiments, $R^{X1}$ is selected from the group consisting of:
The present disclosure provides a compound having Formula (IIc) or (IIc′):

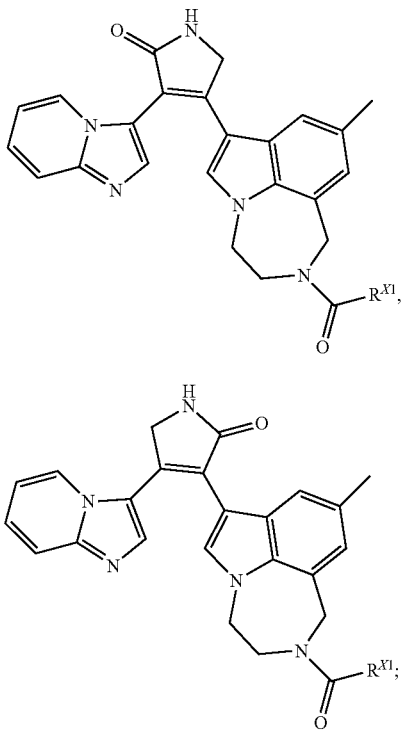
(IIc)
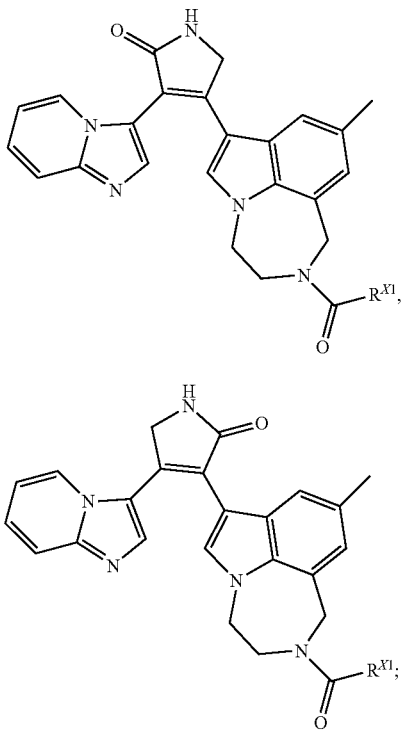
(IIc')
and pharmaceutically acceptable salts and tautomers thereof.
In some embodiments, $R^{X1}$ is selected from the group consisting of:
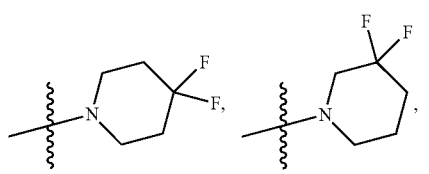
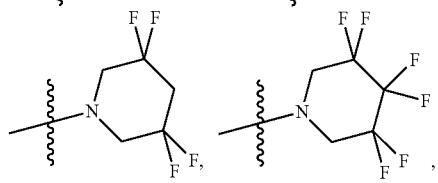
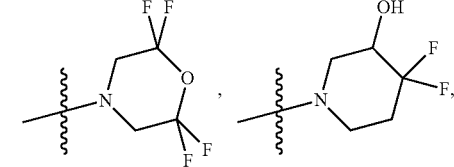
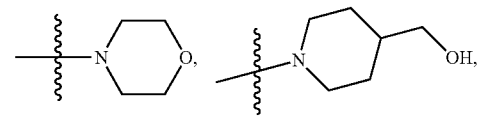
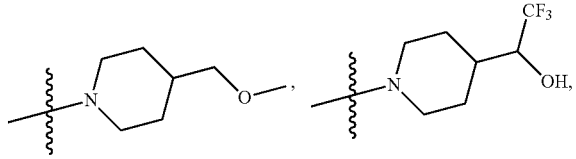
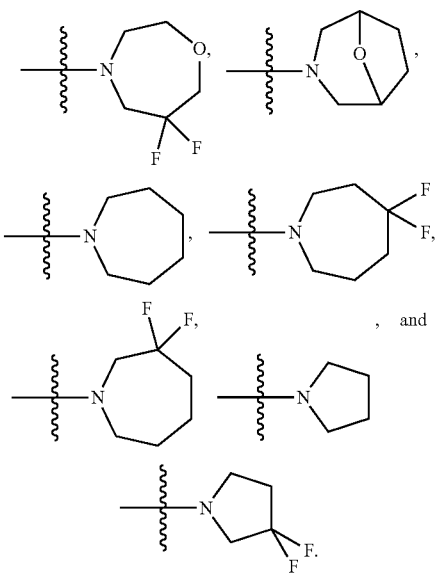
-continued
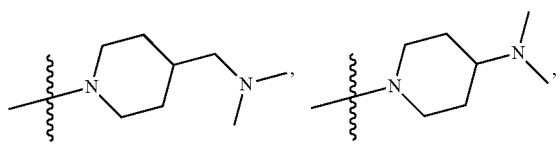
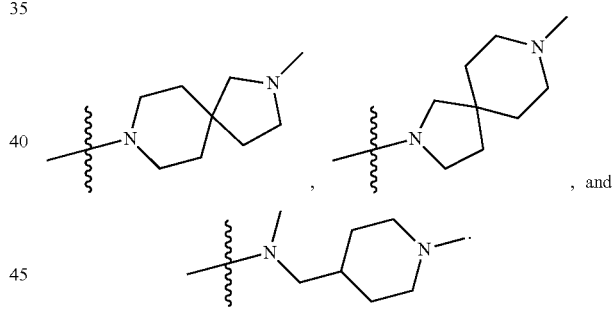
, and
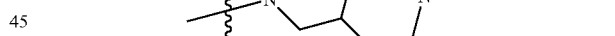
In some embodiments, $R^{X1}$ is selected from the group consisting of:
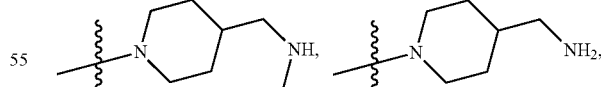
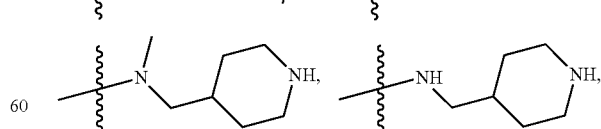
, and
In some embodiments, $R^{X1}$ is selected from the group consisting of:
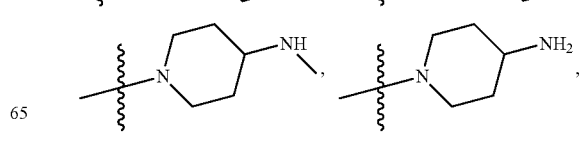

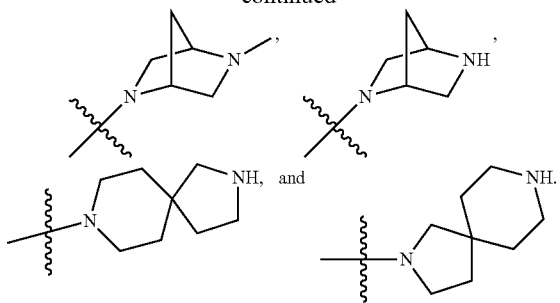
The present disclosure provides a compound having Formula (IId) or (IId'):
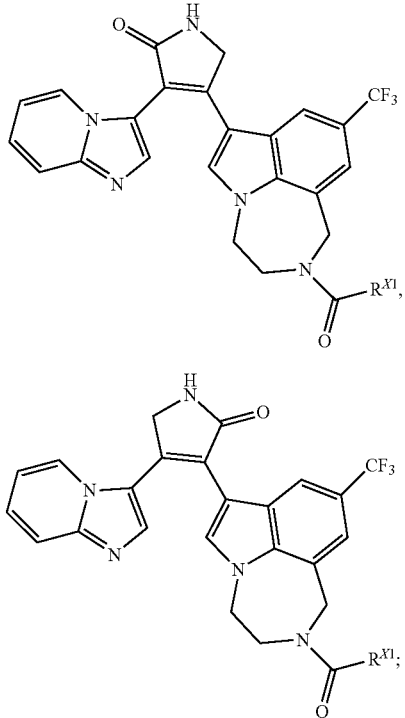
and pharmaceutically acceptable salts and tautomers thereof.
In some embodiments, $R^{X1}$ is selected from the group consisting of:
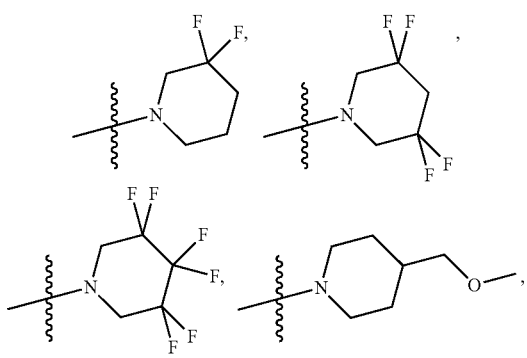
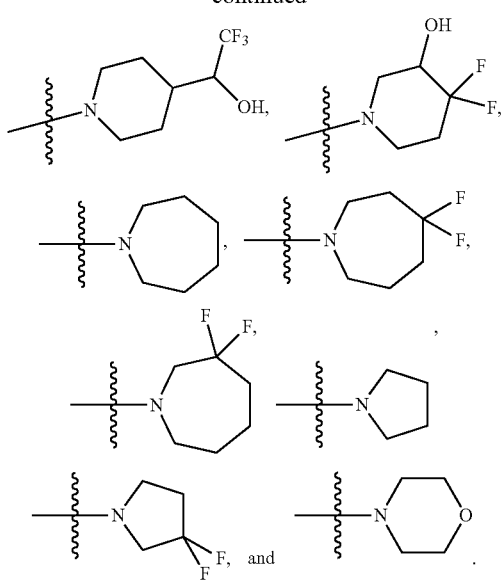
In some embodiments, $R^{X1}$ is selected from the group consisting of:
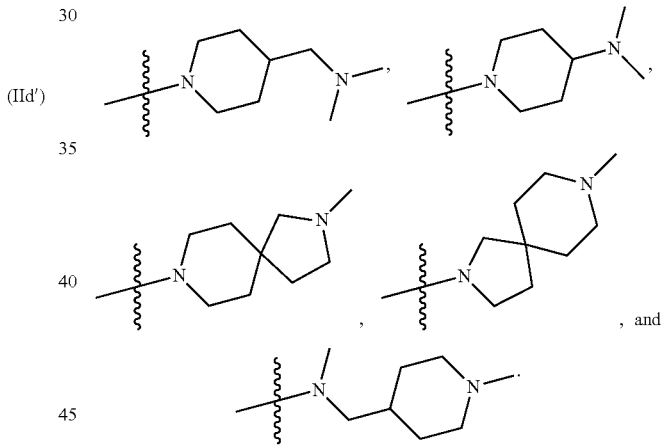
In some embodiments, $R^{X1}$ is selected from the group consisting of:
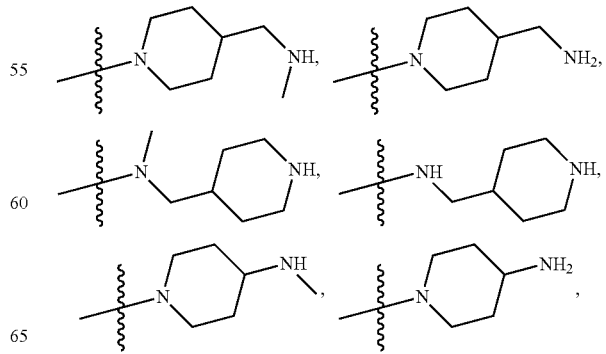

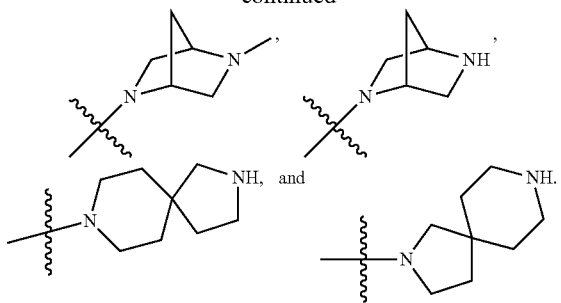
The present disclosure provides a compound having Formula (IIe) or (IIe'):
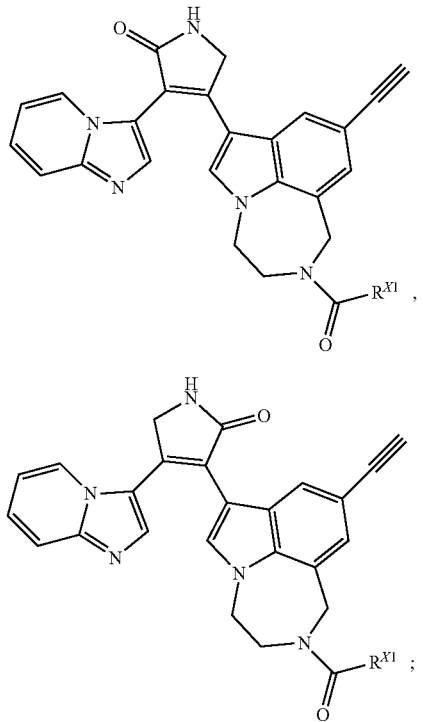
and pharmaceutically acceptable salts and tautomers thereof.
In some embodiments, $R^{X1}$ is selected from the group consisting of:
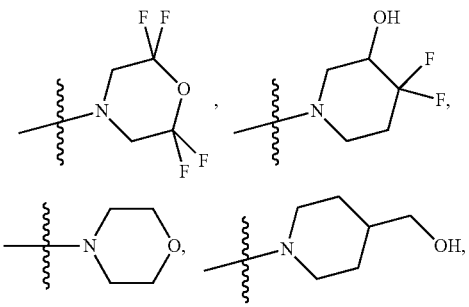
In some embodiments, $R^{X1}$ is selected from the group consisting of:
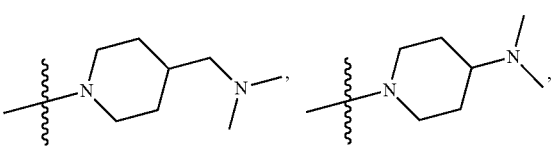
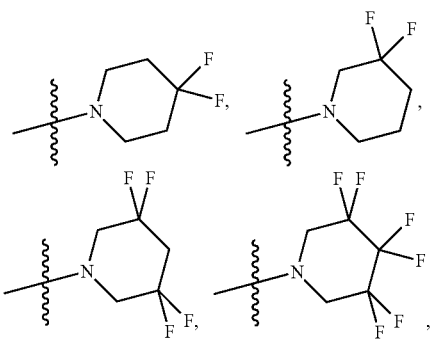
In some embodiments, $R^{X1}$ is selected from the group consisting of:

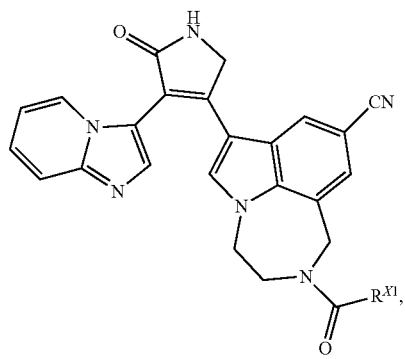
The present disclosure provides a compound having Formula (IIf) or (IIf'):
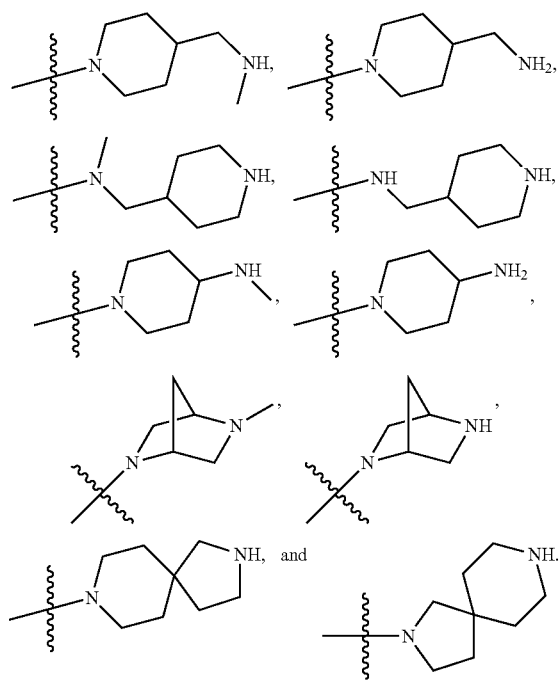
(IIf)
(IIf')
and pharmaceutically acceptable salts and tautomers thereof.
In some embodiments, $R^{X1}$ is selected from the group consisting of:
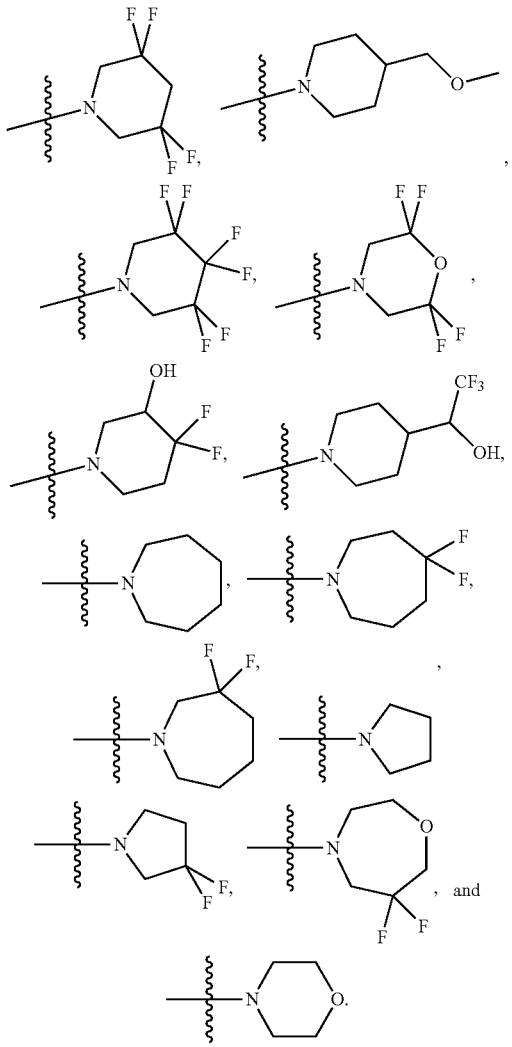
In some embodiments, $R^{X1}$ is selected from the group consisting of:
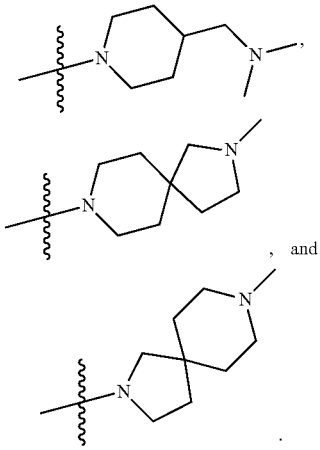
In some embodiments, $R^{X1}$ is selected from the group consisting of:

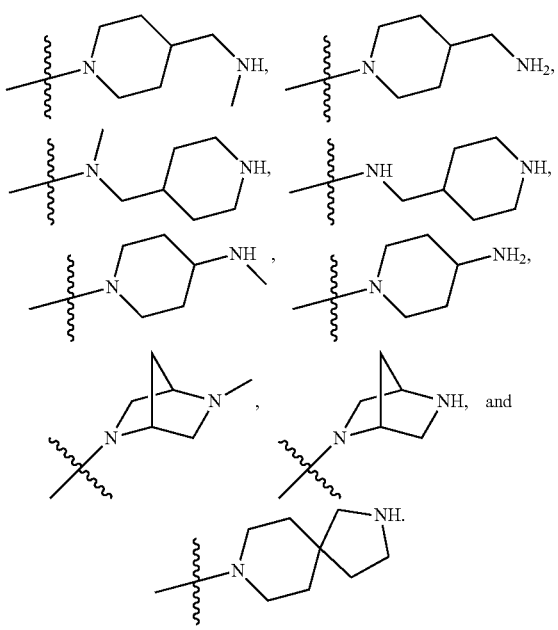

Unless otherwise stated, structures depicted herein are also meant to include compounds which differ only in the presence of one or more isotopically enriched atoms. For example, compounds having the present structure except for the replacement of a hydrogen atom by deuterium or tritium, or the replacement of a carbon atom by $^{13}C$ or $^{14}C$, or the replacement of a nitrogen atom by $^{15}N$, or the replacement of an oxygen atom with $^{17}O$ or $^{18}O$ are within the scope of the present disclosure. Such isotopically labeled compounds are useful as research or diagnostic tools. In certain embodiments, deuteration can be used to slow metabolism and thus potentially improve the compound half-life. Any or all hydrogens in the compound can be replaced with deuterium.

Methods of Synthesizing the Disclosed Compounds

The compounds of the present invention may be made by a variety of methods, including standard chemistry. Suitable synthetic routes are depicted in the schemes given below.

The compounds of any of the formulae described herein may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of the present disclosure.

Those skilled in the art will recognize if a stereocenter exists in any of the compounds of the present disclosure. Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

Methods of Making the Compounds

The compounds described herein may be made from commercially available starting materials or synthesized using known organic, inorganic, and/or enzymatic processes.

The compounds of the present invention can be prepared in a number of ways well known to those skilled in the art of organic synthesis. By way of example, compounds of the disclosure can be synthesized using the methods described below, together with synthetic methods known in the art of synthetic organic chemistry, or variations thereon as appreciated by those skilled in the art. These methods include but are not limited to those methods described below.

The compounds of the present invention can be prepared as described in J. Med. Chem. 2008, 51, 3814-3824, Preparation of pyrrolo[3,2,1-ij]quinoline derivatives, pharmaceutical compositions and methods for treatment of cancer; Wang, Jianqiang et al PCT Int. Appl., 2009002806, 31 Dec. 2008, Preparation of indazolyl-substituted pyrroline compounds as kinase inhibitors for treating or ameliorating kinase-mediated disorders; Zhang, Han-Cheng et al PCT Int. Appl., 2002046183; Synthesis (1999), (2), 275-281, and Synthesis, 1994, 25-7.

A representative synthesis for subject compounds is shown in Schemes 1 to 4.

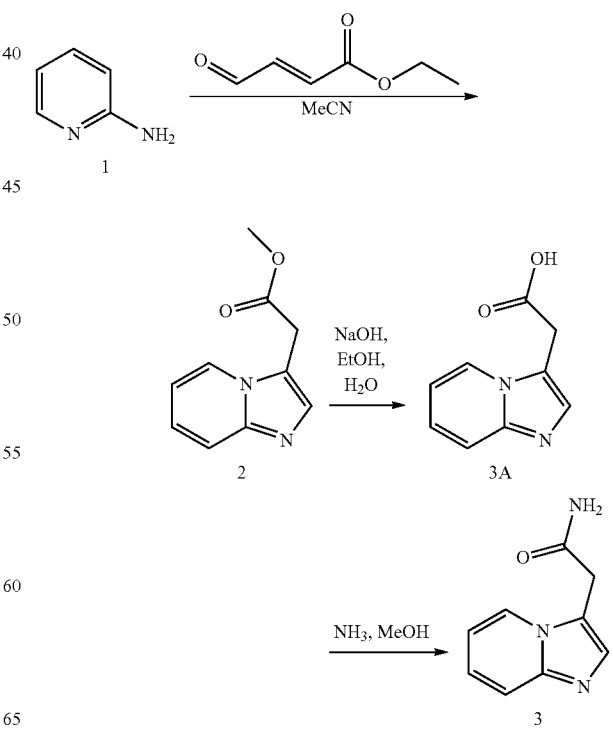

Scheme 1. General synthesis of illustrative intermediate 3

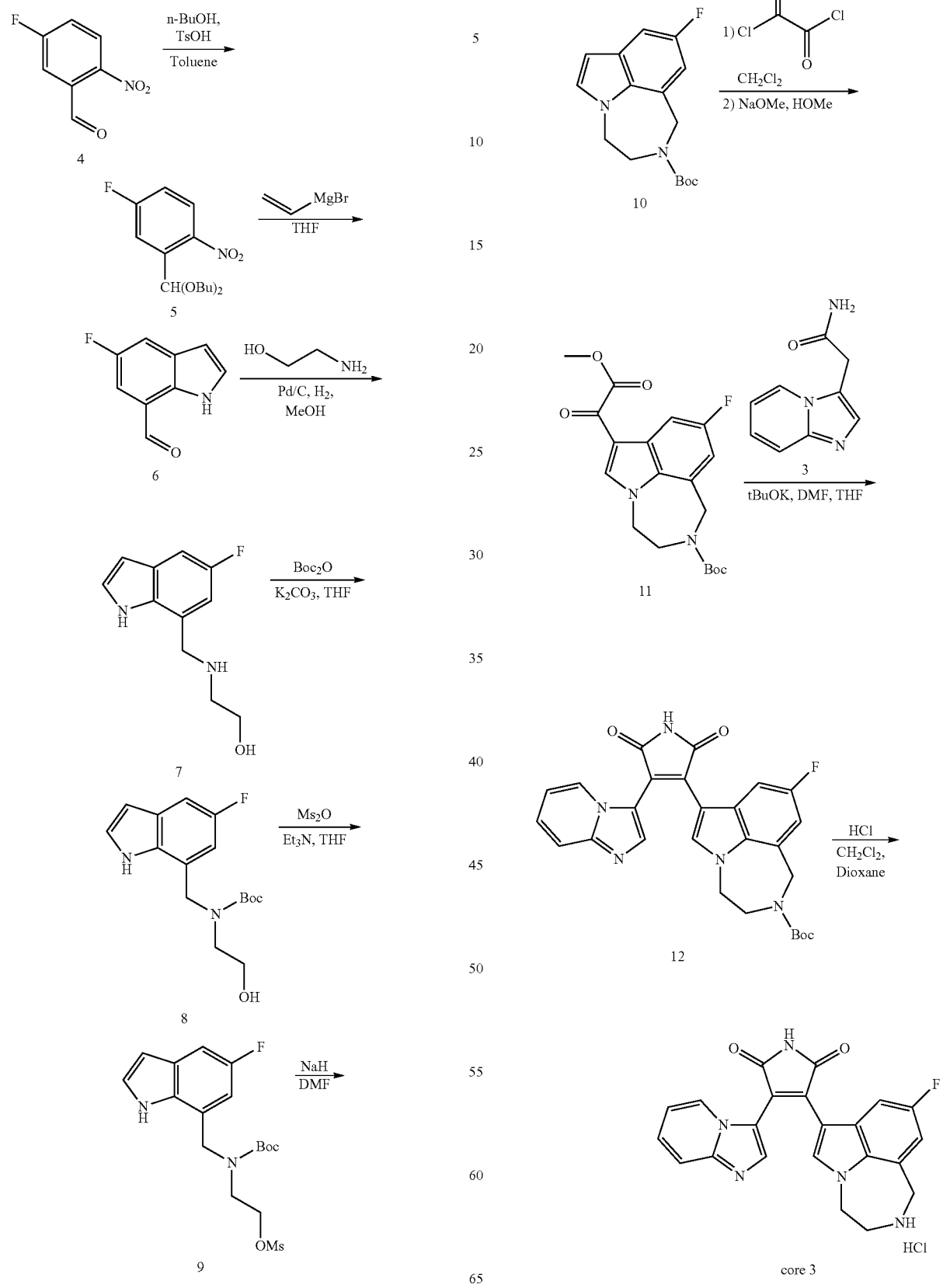

Scheme 3. General synthesis of compounds of Formula (I)
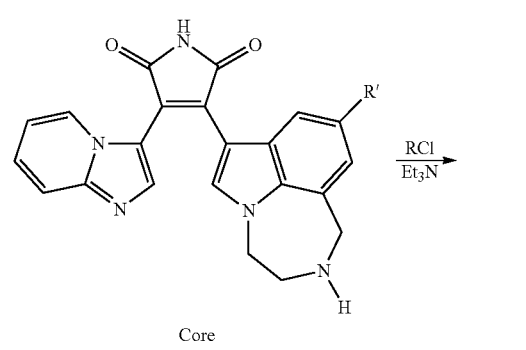
Scheme 4. Specific synthesis of Compound I-4
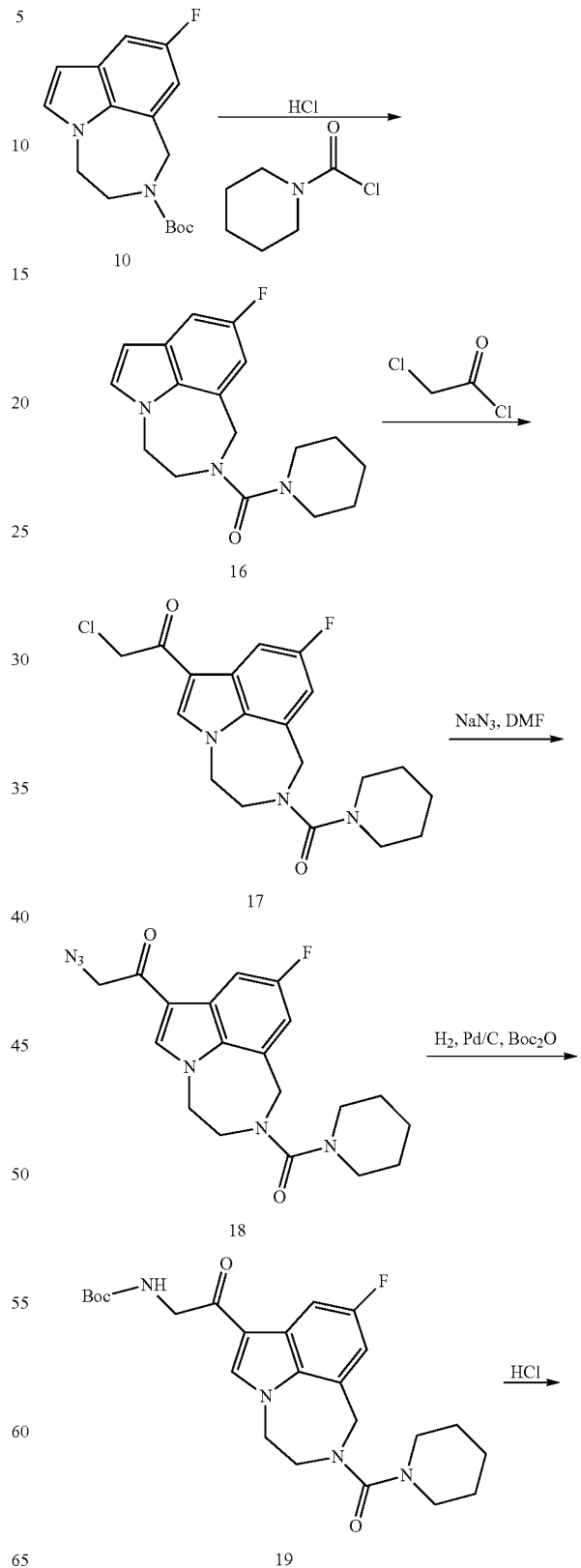
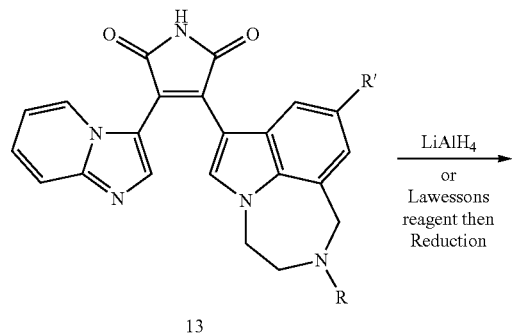
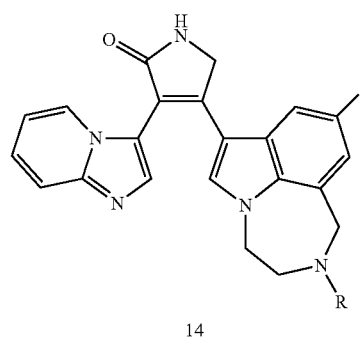

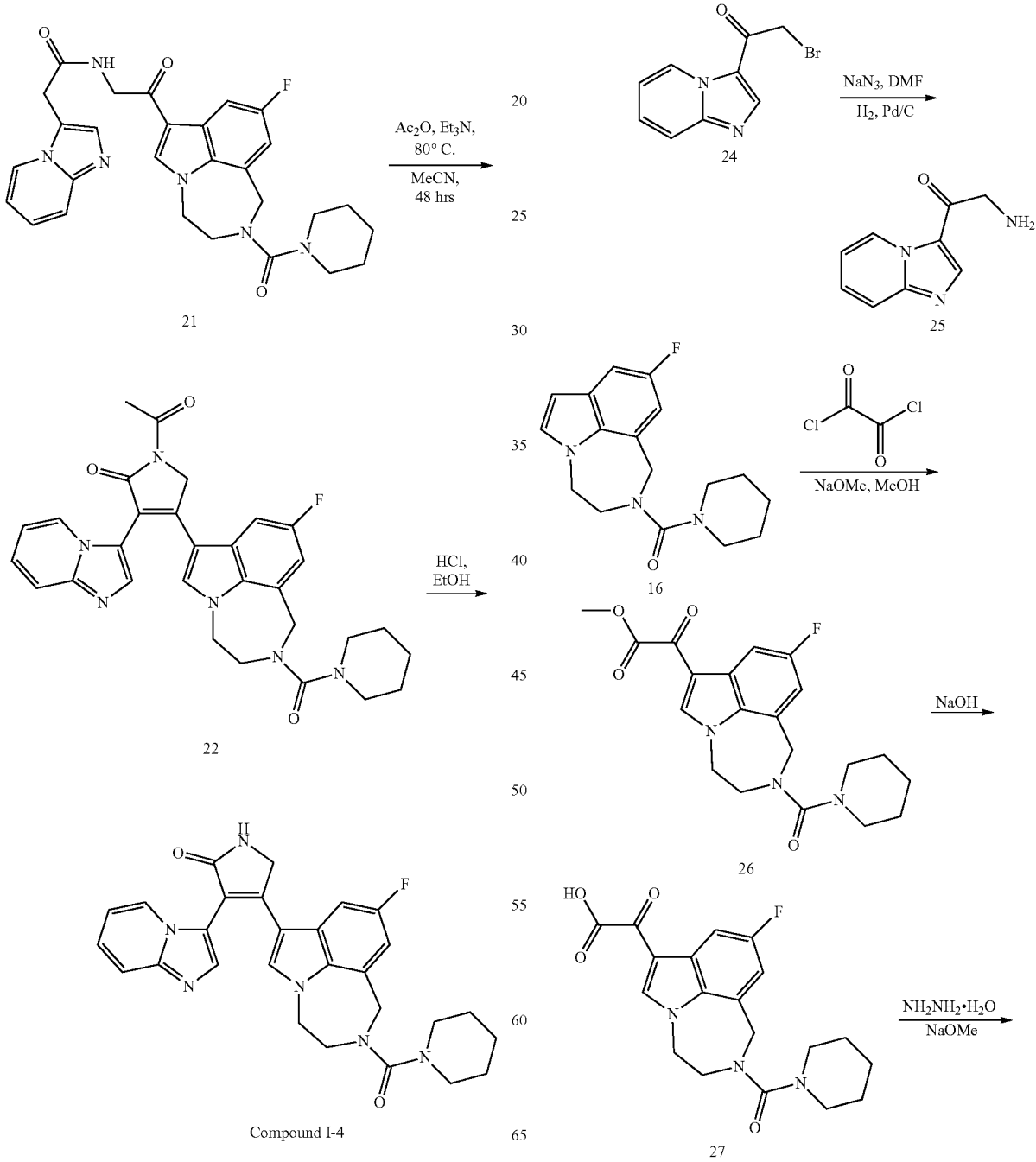

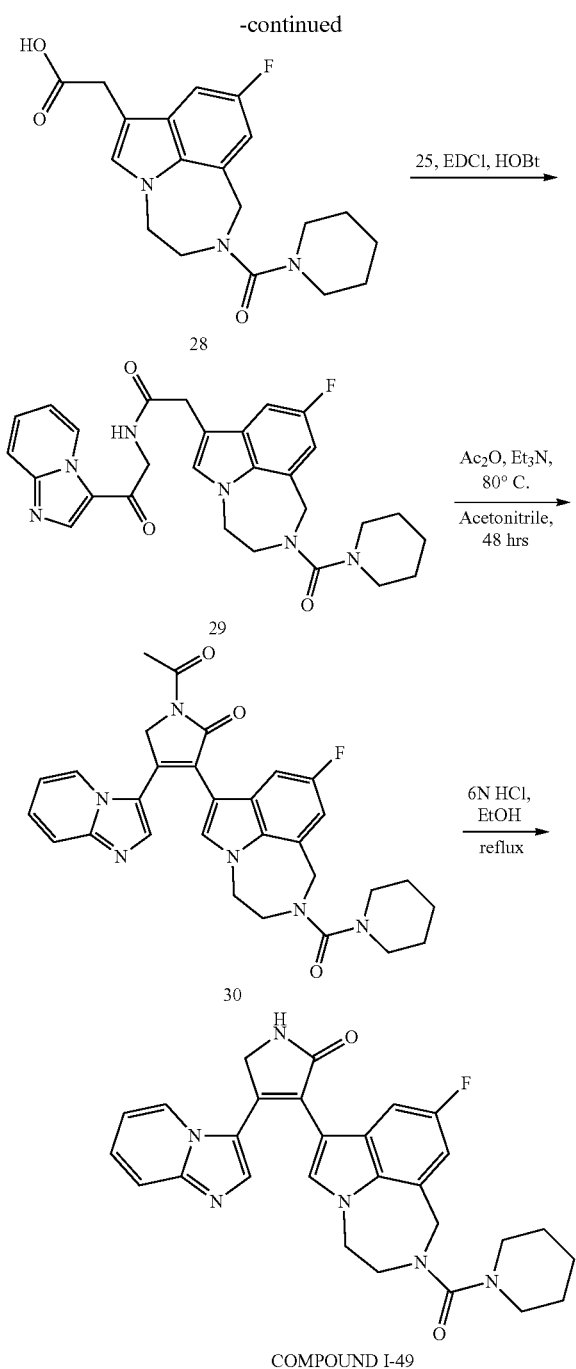

COMPOUND I-49

Methods of Using the Disclosed Compounds

The present disclosure relates to methods to activate the Wnt pathway or inhibiting GSK3 activity. Although there are hundreds of purported GSK3 inhibitors in the patent and non patent literature, not all GSK3 inhibitors when administered in the absence of other therapeutic agents would be sufficient nor potent enough to promote activation of stem cell proliferation.

In another aspect the present disclosure relates to methods to prevent, reduce or treat the incidence and/or severity of disorders or diseases associated with absence or lack of certain tissue cells. In one aspect the present disclosure relates to methods to prevent, reduce or treat the incidence and/or severity of inner ear disorders and hearing impairments involving inner ear tissue, particularly inner ear hair cells, their progenitors, and optionally, the stria vascularis, and associated auditory nerves. Of particular interest are those conditions that lead to permanent hearing loss where reduced number of hair cells may be responsible and/or decreased hair cell function. Also of interest are those arising as an unwanted side-effect of ototoxic therapeutic drugs including cisplatin and its analogs, aminoglycoside antibiotics, salicylate and its analogs, or loop diuretics. In certain embodiments, the present disclosure relates to inducing, promoting, or enhancing the growth, proliferation or regeneration of inner ear tissue, particularly inner ear supporting cells and hair cells.

Among other things, the methods presented here are useful for the preparation of pharmaceutical formulations for the prophylaxis and/or treatment of acute and chronic ear disease and hearing loss, dizziness and balance problems especially of sudden hearing loss, acoustic trauma, hearing loss due to chronic noise exposure, presbycusis, trauma during implantation of the inner ear prosthesis (insertion trauma), dizziness due to diseases of the inner ear area, dizziness related and/or as a symptom of Meniere's disease, vertigo related and/or as a symptom of Meniere's disease, tinnitus, and hearing loss due to antibiotics and cytostatics and other drugs.

When cochlea supporting cell populations are treated with the compound, whether the population is in vivo or in vitro, the treated supporting cells exhibit stem-like behavior in that the treated supporting cells have the capacity to proliferate and differentiate and, more specifically, differentiate into cochlear hair cells. Preferably, the compound induces and maintains the supporting cells to produce daughter stem cells that can divide for many generations and maintain the ability to have a high proportion of the resulting cells differentiate into hair cells. In certain embodiments, the proliferating stem cells express stem cell markers which may include Lgr5, Sox2, Opeml, Phex, lin28, Lgr6, cyclin D1, Msx1, Myb, Kit, Gdnf3, Zic3, Dppa3, Dppa4, Dppa5, Nanog, Esrrb, Rexl, Dnmt3a, Dnmt3b, Dnmt31, Utf1, Tcl1, Oct4, Klf4, Pax6, Six2, Zic1, Zic2, Otx2, Bmi1, CDX2, STATS, Smad1, Smad2, smad2/3, smad4, smad5, and/or smad7.

In some embodiments, the method of the present disclosure may be used to maintain, or even transiently increase stemness (i.e., self-renewal) of a pre-existing supporting cell population prior to significant hair cell formation. In some embodiments, the pre-existing supporting cell population comprises inner pillar cells, outer pillar cells, inner phalangeal cells, Deiter cells, Hensen cells, Boettcher cells, and/or Claudius cells. Morphological analyses with immunostaining (including cell counts) and lineage tracing across a Representative Microscopy Samples may be used to confirm expansion of one or more of these cell-types. In some embodiments, the pre-existing supporting cells comprise Lgr5$^+$ cells. Morphological analyses with immunostaining (including cell counts) and qPCR and RNA hybridization may be used to confirm Lgr5 upregulation amongst the cell population.

Advantageously, the methods of the present disclosure achieve these goals without the use of genetic manipulation. Germ-line manipulation used in many academic studies is not a therapeutically desirable approach to treating hearing loss. In general, the therapy preferably involves the administration of a small molecule, peptide, antibody, or other non-nucleic acid molecule or nucleic acid delivery vector unaccompanied by gene therapy. In certain embodiments, the therapy involves the administration of a small organic molecule. Preferably, hearing protection or restoration is achieved through the use of a (non-genetic) therapeutic that is injected in the middle ear and diffuses into the cochlea.

The cochlea relies heavily on all present cell types, and the organization of these cells is important to their function. As supporting cells play an important role in neurotransmitter cycling and cochlear mechanics. Thus, maintaining a rosette patterning within the organ of Corti may be important for function. Cochlear mechanics of the basilar membrane activate hair cell transduction. Due to the high sensitivity of cochlear mechanics, it is also desirable to avoid masses of cells. In all, maintaining proper distribution and relation of hair cells and supporting cells along the basilar membrane, even after proliferation, is likely a desired feature for hearing as supporting cell function and proper mechanics is necessary for normal hearing.

In one embodiment of the present disclosure, the cell density of hair cells in a cochlear cell population is expanded in a manner that maintains, or even establishes, the rosette pattern characteristic of cochlear epithelia.

In accordance with one aspect of the present disclosure, the cell density of hair cells may be increased in a population of cochlear cells comprising both hair cells and supporting cells. The cochlear cell population may be an in vivo population (i.e., comprised by the cochlear epithelium of a subject) or the cochlear cell population may be an in vitro (ex vivo) population. If the population is an in vitro population, the increase in cell density may be determined by reference to a Representative Microscopy Sample of the population taken prior and subsequent to any treatment. If the population is an in vivo population, the increase in cell density may be determined indirectly by determining an effect upon the hearing of the subject with an increase in hair cell density correlating to an improvement in hearing.

In one embodiment, supporting cells placed in a Stem Cell Proliferation Assay in the absence of neuronal cells form ribbon synapses.

In a native cochlea, patterning of hair cells and supporting cells occurs in a manner parallel to the basilar membrane. In one embodiment of the present disclosure, the proliferation of supporting cells in a cochlear cell population is expanded in a manner that the basilar membrane characteristic of cochlear epithelia.

In one embodiment, the number of supporting cells in an initial cochlear cell population is selectively expanded by treating the initial cochlear cell population with a composition provided herein to form an intermediate cochlear cell population and wherein the ratio of supporting cells to hair cells in the intermediate cochlear cell population exceeds the ratio of supporting cells to hair cells in the initial cochlear cell population. The expanded cochlear cell population may be, for example, an in vivo population, an in vitro population or even an in vitro explant. In one such embodiment, the ratio of supporting cells to hair cells in the intermediate cochlear cell population exceeds the ratio of supporting cells to hair cells in the initial cochlear cell population. For example, in one such embodiment the ratio of supporting cells to hair cells in the intermediate cochlear cell population exceeds the ratio of supporting cells to hair cells in the initial cochlear cell population by a factor of 1.1. By way of further example, in one such embodiment the ratio of supporting cells to hair cells in the intermediate cochlear cell population exceeds the ratio of supporting cells to hair cells in the initial cochlear cell population by a factor of 1.5. By way of further example, in one such embodiment the ratio of supporting cells to hair cells in the intermediate cochlear cell population exceeds the ratio of supporting cells to hair cells in the initial cochlear cell population by a factor of 2. By way of further example, in one such embodiment the ratio of supporting cells to hair cells in the intermediate cochlear cell population exceeds the ratio of supporting cells to hair cells in the initial cochlear cell population by a factor of 3. In each of the foregoing embodiments, the capacity of a composition of the present disclosure to expand a cochlear cell population as described in this paragraph may be determined by means of a Stem Cell Proliferation Assay.

In one embodiment, the number of stem cells in a cochlear cell population is expanded to form an intermediate cochlear cell population by treating a cochlear cell population with a composition provided herein wherein the cell density of stem cells in the intermediate cochlear cell population exceeds the cell density of stem cells in the initial cochlear cell population. The treated cochlear cell population may be, for example, an in vivo population, an in vitro population or even an in vitro explant. In one such embodiment, the cell density of stem cells in the treated cochlear cell population exceeds the cell density of stem cells in the initial cochlear cell population by a factor of at least 1.1. For example, in one such embodiment the cell density of stem cells in the treated cochlear cell population exceeds the cell density of stem cells in the initial cochlear cell population by a factor of at least 1.25. For example, in one such embodiment the cell density of stem cells in the treated cochlear cell population exceeds the cell density of stem cells in the initial cochlear cell population by a factor of at least 1.5. By way of further example, in one such embodiment the cell density of stem cells in the treated cochlear cell population exceeds the cell density of stem cells in the initial cochlear cell population by a factor of at least 2. By way of further example, in one such embodiment the cell density of stem cells in the treated cochlear cell population exceeds the cell density of stem cells in the initial cochlear cell population by a factor of at least 3. In vitro cochlear cell populations may expand significantly more than in vivo populations; for example, in certain embodiments the cell density of stem cells in an expanded in vitro population of stem cells may be at least 4, 5, 6, 7, 8, 9, 10, 15, 20, 25, 30, 35, 40, 45, 50, 75, 100, 200, 300, 400, 500, 600, 700, 800, 900, 1000, 2,000 or even 3,000 times greater than the cell density of the stem cells in the initial cochlear cell population. In each of the foregoing embodiments, the capacity of a composition of the present disclosure to expand a cochlear cell population as described in this paragraph may be determined by means of a Stem Cell Proliferation Assay.

In accordance with one aspect of the present disclosure, a cochlea supporting cell population is treated with a composition provided herein to increase the Lgr5 activity of the population. For example, in one embodiment the composition provided herein has the capacity to increase and maintain the Lgr5 activity of an in vitro population of cochlea supporting cells by factor of at least 1.2. By way of further example, in one such embodiment the compound has the capacity to increase the Lgr5 activity of an in vitro population of cochlea supporting cells by factor of 1.5. By way of further example, in one such embodiment the compound has the capacity to increase the Lgr5 activity of an in vitro population of cochlea supporting cells by factor of 2, 3, 5 10, 100, 500, 1,000, 2,000 or even 3,000. Increases in Lgr5 activity may also be observed for in vivo populations but the observed increase may be somewhat more modest. For example, in one embodiment the compound has the capacity to increase the Lgr5 activity of an in vivo population of cochlea supporting cells by at least 5%. By way of further example, in one such embodiment the compound has the capacity to increase the Lgr5 activity of an in vivo population of cochlea supporting cells by at least 10%. By way of further example, in one such embodiment the compound has the capacity to increase the Lgr5 activity of an in vivo population of cochlea supporting cells by at least 20%. By way of further example, in one such embodiment the compound has the capacity to increase the Lgr5 activity of an in vivo population of cochlea supporting cells by at least 30%. In each of the foregoing embodiments, the capacity of the compound for such an increase in Lgr5 activity may be demonstrated, for example, in an In Vitro Lgr5$^+$ Activity Assay and in an in vivo population may be demonstrated, for example, in an In Vivo Lgr5$^+$ Activity Assay, as measured by isolating the organ and performing morphological analyses using immunostaining, endogenous fluorescent protein expression of Lgr5 (eg. Lgr5, Sox2), and qPCR for Lgr5.

In addition to increasing the Lgr5 activity of the population, the number of Lgr5$^+$ supporting cells in a cochlea cell population may be increased by treating a cochlea cell population containing Lgr5$^+$ supporting cells (whether in vivo or in vitro) with a composition provided herein. In general, the cell density of the stem/progenitor supporting cells may expand relative to the initial cell population via one or more of several mechanisms. For example, in one such embodiment, newly generated Lgr5$^+$ supporting cells may be generated that have increased stem cell propensity (i.e., greater capacity to differentiate into hair cell). By way of further example, in one such embodiment no daughter Lgr5$^+$ cells are generated by cell division, but pre-existing Lgr5$^+$ supporting cells are induced to differentiate into hair cells. By way of further example, in one such embodiment no daughter cells are generated by cell division, but Lgr5$^-$ supporting cells are activated to a greater level of Lgr5 activity and the activated supporting cells are then able to differentiate into hair cells. Regardless of the mechanism, in one embodiment the compound of the present disclosure has the capacity to increase the cell density of Lgr5$^+$ supporting cells in an in vitro isolated cell population of cochlea supporting cells by factor of at least 5. By way of further example, in one such embodiment the compound has the capacity to increase the cell density of Lgr5$^+$ supporting cells in an in vitro population of cochlea supporting cells by factor of at least 10. By way of further example, in one such embodiment the compound has the capacity to increase the cell density of Lgr5$^+$ supporting cells in an in vitro population of cochlea supporting cells by factor of at least 100, at least 500, at least 1,000 or even at least 2,000. Increases in the cell density of Lgr5$^+$ supporting cells may also be observed for in vivo populations but the observed increase may be somewhat more modest. For example, in one embodiment the compound has the capacity to increase the cell density of Lgr5$^+$ supporting cells in an in vivo population of cochlea supporting cells by at least 5%. By way of further example, in one such embodiment the compound has the capacity to increase the cell density of Lgr5$^+$ supporting cells in an in vivo population of cochlea supporting cells by at least 10%. By way of further example, in one such embodiment the compound has the capacity to increase the cell density of Lgr5$^+$ supporting cells in an in vivo population of cochlea supporting cells by at least 20%. By way of further example, in one such embodiment the compound has the capacity to increase the cell density of Lgr5$^+$ supporting cells in an in vivo population of cochlea supporting cells by at least 30%. The capacity of the compound for such an increase in Lgr5$^+$ supporting cells in an in vitro population may be demonstrated, for example, in a Stem Cell Proliferation Assay or in an appropriate in vivo assay. In one embodiment, a compound of the present disclosure has the capacity to increase the number of Lgr5$^+$ cells in the cochlea by inducing expression of Lgr5 in cells with absent or low detection levels of the protein, while maintaining Native Morphology. In one embodiment, a compound of the present disclosure has the capacity to increase the number of Lgr5$^+$ cells in the cochlea by inducing expression of Lgr5 in cells with absent or low detection levels of the protein, while maintaining Native Morphology and without producing Cell Aggregates.

In addition to increasing the cell density of Lgr5$^+$ supporting cells, in one embodiment the method of the present disclosure has the capacity to increase the ratio of Lgr5$^+$ cells to hair cells in a cochlear cell population. In one embodiment, the number of Lgr5$^+$ supporting cells in an initial cochlear cell population is selectively expanded by treating the initial cochlear cell population with a compound of the present disclosure to form an expanded cell population and wherein the number of Lgr5$^+$ supporting cells in the expanded cochlear cell population at least equals the number of hair cells. The expanded cochlear cell population may be, for example, an in vivo population, an in vitro population or even an in vitro explant. In one such embodiment, the ratio of Lgr5$^+$ supporting cells to hair cells in the expanded cochlear cell population is at least 1:1. For example, in one such embodiment the ratio of Lgr5$^+$ supporting cells to hair cells in the expanded cochlear cell population is at least 1.5:1. By way of further example, in one such embodiment the ratio of Lgr5$^+$ supporting cells to hair cells in the expanded cochlear cell population is at least 2:1. By way of further example, in one such embodiment the ratio of Lgr5$^+$ supporting cells to hair cells in the expanded cochlear cell population is at least 3:1. By way of further example, in one such embodiment the ratio of Lgr5$^+$ supporting cells to hair cells in the expanded cochlear cell population is at least 4:1. By way of further example, in one such embodiment the ratio of Lgr5$^+$ supporting cells to hair cells in the expanded cochlear cell population is at least 5:1. In each of the foregoing embodiments, the capacity of the compound of the present disclosure to expand a cochlear cell population as described in this paragraph may be determined by means of a Stem Cell Proliferation Assay.

In certain embodiments, the method increases the fraction of the Lgr5$^+$ cells to total cells on the sensory epithelium by at least 10%, 20%, 50%, 100%, 250% 500%, 1,000% or 5000%.

In certain embodiments, the method increases the Lgr5$^+$ cells until they become at least 10, 20, 30, 50, 70, or 85% of the cells on the sensory epithelium, e.g. the Organ of Corti.

In general, excessive proliferation of supporting cells in the cochlea is preferably avoided. In one embodiment, the method of the present disclosure has the capacity to expand a cochlear cell population without creating a protrusion of new cells beyond the native surface of the cochlea, e.g a Cell Aggregate. In some embodiments, 30 days after placing a composition provided herein on the round or oval membrane, the cochlear tissue has Native Morphology. In some embodiments, 30 days after placing the compound on the round or oval membrane, the cochlear tissue has Native Morphology and lacks Cell Aggregates. In some embodiments, 30 days after placing the compound on the round or oval membrane, the cochlear tissue has Native Morphology and at least 10, 20, 30, 50, 75, 90, 95, 98, or even at least 99% of the Lgr5$^+$ cells in the Organ of Corti are not part of Cell Aggregates.

In addition to expanding supporting cell populations, generally, and Lgr5$^+$ supporting cells, specifically, as described above, the method of the present disclosure has the capacity to maintain, in the daughter cells, the capacity to differentiate into hair cells. In in vivo populations, the maintenance of this capacity may be indirectly observed by an improvement in a subject's hearing. In in vitro populations, the maintenance of this capacity may be directly observed by an increase in the number of hair cells relative to a starting population or indirectly by measuring LGR5 activity, SOX2 activity or one or more of the other stem cell markers identified elsewhere herein.

In one embodiment, the capacity of the method to increase the stemness of a population of cochlear supporting cells, in general, or a population of Lgr5$^+$ supporting cells, in particular, may be correlated with an increase of Lgr5 activity of an in vitro population of isolated Lgr5$^+$ cells as determined by an Lgr5 Activity Assay. As previously noted, in one such embodiment, the compound has the capacity to increase the Lgr5 activity of stem cells in the intermediate cell population by a factor of 5 on average relative to the Lgr5 activity of the cells in the initial cell population. By way of further example, in one such embodiment the method has the capacity to increase the Lgr5 activity of the stem cells genes in the intermediate cell population by a factor of 10 relative to the Lgr5 activity of the cells in the initial cell population. By way of further example, in one such embodiment the method has the capacity to increase the Lgr5 activity of the stem cells in the intermediate cell population by a factor of 100 relative to the Lgr5 activity of the cells in the initial cell population. By way of further example, in one such embodiment the method has the capacity to increase the Lgr5 activity of the stem cells in the intermediate cell population by a factor of 1000 relative to the Lgr5 activity of the cells in the initial cell population. In each of the foregoing embodiments, the increase in the activity of stem cells in the cell population may be determined in vitro by immunostaining or endogenous fluorescent protein expression for target genes and analysis of their relative intensities via imaging analysis or flow cytometry, or using qPCR for target stem cell genes. The identity of the resulting stem cell population may optionally be further determined by stem cell assays including stem cell marker expression assay, colony forming assay, self-renewal assay and differentiation assay as defined in Stem cell assay.

In some embodiments, the method applied to an adult mammal produces a population of adult mammalian Lgr5$^+$ cells that are in S-phase.

In one embodiment, after applying the composition provided herein to the round or oval of a mouse, the in vivo Lgr5$^+$ Activity of a cell population in the Organ of Corti increases 1.3×, 1.5×, up to 20× over baseline for a population that has not been exposed to the compound. In some embodiments, applying the compound to the round or oval of a mouse increases the average In vivo Lgr5$^+$ Activity for cells in the Organ of Corti is increased 1.3×, 1.5×, up to 20× over baseline for a population that has not been exposed to the compound.

In certain embodiments, the method increases the Lgr5$^+$ cells until they become at least 10%, 7.5%, 10%, up to 100% of the supporting cell population by number.

In certain embodiments, the compound has the capacity to increase the percentage of Lgr5$^+$ cell in a cochlea by 5%, 10%, 25%, 50%, or 80%.

In certain embodiments, the stem cell population is of an in vivo subject, and the method is a treatment for hearing loss and/or vestibular dysfunction (e.g., wherein the generation of inner ear hair cells from the expanded population of stem cells results in partial or full recovery of hearing loss and/or improved vestibular function). In certain embodiments, the stem cell population is of an in vivo subject, and the method further comprises delivering a drug to the subject (e.g., for treatment of a disease and/or disorder unrelated to hearing loss and/or vestibular dysfunction) at a higher concentration than a known safe maximum dosage of the drug for the subject (e.g., the known safe maximum dosage if delivered in the absence of the generation of inner ear hair cells resulting from the method) (e.g., due to a reduction or elimination of a dose-limiting ototoxicity of the drug).

In certain embodiments, the method further comprises performing high throughput screening using the generated inner ear hair cells. In certain embodiments, the method comprises using the generated inner ear hair cells to screen molecules for toxicity against inner ear hair cells. In certain embodiments, the method comprises using the generated inner ear hair cells to screen molecules for ability to improve survival of inner ear hair cells (e.g., inner ear hair cells exposed to said molecules).

In another aspect, the disclosure is directed to a method of producing an expanded population of stem cells, the method comprising: administering or causing to be administered to a stem cell population (e.g., of an in vitro, ex vivo, or in vivo sample/subject) a composition provided herein.

In certain embodiments, the administering step is carried out by performing one or more injections into the ear (e.g., transtympanically into the middle ear and/or inner ear).

In certain embodiments, the administering step comprises administering the GSK3 inhibitor and/or Wnt agonist in a sustained manner.

In certain embodiments, the stem cells are inner ear stem cells and/or supporting cells.

In certain embodiments, the method further comprises performing high throughput screening using the generated expanded population of stem cells. In certain embodiments, the method further comprises using the generated stem cells to screen molecules for toxicity against stem cells and/or their progeny. In certain embodiments, the method comprises using the generated stem cells to screen molecules for ability to improve survival of stem cells and/or their progeny.

In another aspect, the disclosure is directed to a method of treating a subject who has, or is at risk of developing, hearing loss and/or vestibular dysfunction, the method comprising: identifying a subject who has experienced, or is at risk for developing, hearing loss and/or vestibular dysfunction, administering or causing to be administered a composition provided herein.

In certain embodiments, the stem cell population comprises Lgr5$^+$ cells. In certain embodiments, the stem cell population comprises post-natal cells. In certain embodiments, the stem cell population comprises epithelial stem cells. In certain embodiments, stem cells include progenitor cells.

In certain embodiments, the step of administering is carried out by performing one or more injections into the ear (e.g., transtympanically into the middle ear and/or inner ear).

In another aspect, the disclosure is directed to a method of generating inner ear hair cells, the method comprising: proliferating stem cells in an initial stem cell population (e.g., of an in vitro, ex vivo, or in vivo sample/subject), resulting in an expanded population of stem cells (e.g., such that the expanded population is a factor of at least 1.25, 1.5, 1.75, 2, 3, 5, 10, or 20 greater than the initial stem cell population); and facilitating generation of inner ear hair cells from the expanded population of stem cells.

In another aspect, the disclosure is directed to a method of generating inner ear hair cells, the method comprising administering a composition provided herein (e.g., in a pharmaceutically acceptable form (e.g., salt)) to a cell population in an inner ear of a subject, thereby facilitating generation of inner ear hair cells.

In another aspect, the disclosure is directed to a method of generating inner ear hair cells, the method comprising: proliferating post-natal LGR5+ cells in an initial population (e.g., of an in vitro, ex vivo, or in vivo sample/subject), resulting in an expanded population of LGR5+ cells (e.g., such that the expanded population is a factor of at least 1.25, 1.5, 1.75, 2, 3, 5, 10, or 20 greater than the initial stem cell population), said expanded population of LGR5+ cells resulting in generation of inner ear hair cells. In certain embodiments, stem cells include progenitor cells.

In another aspect, the disclosure is directed to a method of treating a disease or disorder, the method comprising: proliferating post-natal Lgr5$^+$ epithelial cells in an initial population of a subject (in vivo), resulting in an expanded population of Lgr5+ epithelial cells (e.g., such that the expanded population is a factor of at least 1.25, 1.5, 1.75, 2, 3, 5, 10, or 20 greater than the initial post-natal Lgr5$^+$ epithelial cell population).

In some embodiments, Lgr5$^+$ cells are differentiated into hair cells.

Hair Cell Regrowth

In certain embodiments, the present disclosure is directed to a method of facilitating the generation of inner ear hair cells, the method comprising: administering a compound of present disclosure to expand the stem cell population of cochlear tissue.

In certain embodiments, the present disclosure is directed to a method of facilitating the generation of inner ear hair cells, the method comprising: administering a composition comprising a compound of present disclosure and HDAC inhibitor to expand the stem cell population of cochlear tissue.

In certain embodiments, the present disclosure is directed to a method to regenerate hearing in mammals.

In certain embodiments, the stem cell population is of an in vivo subject, and the method is a treatment for hearing loss and/or vestibular dysfunction.

In certain embodiments, the present disclosure is directed to a method of generating inner ear hair cells using of a compound of the present disclosure to proliferate LGR5+ cells in an initial population in vivo, resulting in an expanded population of LGR5+ cells (e.g., such that the expanded population is at least 2 times, 3 times, 5 times, 10 times, or 20 times greater than the initial stem cell population), resulting in generation of inner ear hair cells.

In certain embodiments, the present disclosure is directed to a method of generating inner ear hair cells using of a composition comprising a compound of present disclosure and HDAC inhibitor to proliferate LGR5+ cells in an initial population in vivo, resulting in an expanded population of LGR5+ cells (e.g., such that the expanded population is at least 2 times, 3 times, 5 times, 10 times, or 20 times greater than the initial stem cell population), resulting in generation of inner ear hair cells.

Intestinal Regeneration

In certain embodiments, the present disclosure is directed to a method of facilitating the generation of intestinal cells, the method comprising: administering a compound of the present disclosure to expand the stem cell population of intestinal epithelia.

In certain embodiments, the present disclosure is directed to a method of facilitating the generation of intestinal cells, the method comprising: administering a composition comprising a compound of present disclosure and HDAC inhibitor to expand the stem cell population of intestinal epithelia.

In certain embodiments, the present disclosure is directed to a method to regenerate intestinal epithelia in mammals.

In certain embodiments, the stem cell population is of an in vivo subject. In certain embodiments, the method is a treatment for promoting the repair of damaged mucosa related to diseases such as chemotherapy-induced gastrointestinal mucositis, Graph Versus Host Disease, gastric ulcer, Crohns, or ulcerative colitis.

Intestinal Lgr5+ Proliferation

In certain embodiments, the present disclosure is directed to a method of facilitating the generation of intestinal cells, the method comprising: administering a compound of the present disclosure to expand the Lgr5+ cell population of intestinal epithelia.

In certain embodiments, the present disclosure is directed to a method of facilitating the generation of intestinal cells, the method comprising: administering a composition comprising a compound of present disclosure and HDAC inhibitor to expand the Lgr5+ cell population of intestinal epithelia.

In certain embodiments, the present disclosure is directed to a method to regenerate Lgr5+ cell population intestinal cells in mammals.

In certain embodiments, the Lgr5+ cell population is in an in vivo subject. In certain embodiments, the method is a treatment for promoting the repair of damaged mucosa related to diseases such as chemotherapy-induced gastrointestinal mucositis, Graph Versus Host Disease, gastric ulcer, Crohns, or ulcerative colitis.

In certain embodiments, the present disclosure is directed to a method of treating a disease or disorder, the method comprising proliferating Lgr5+ epithelial cells in vivo, resulting in an expanded population of Lgr5+ epithelial cells (e.g., such that the expanded population is at least 2 times, 3 times, 5 times, 10 times, or 20 times greater than the initial post-natal Lgr5+ epithelial cell population).

Expansion of a Population of Vestibular Cells

In certain embodiments, the pharmaceutical formulations containing can expand a population of vestibular cells in a vestibular tissue comprising contacting the vestibular tissue. In certain embodiments, the pharmaceutical formulations are capable in a stem cell proliferation assay of increasing the number of supporting cells in a stem cell proliferation assay cell population by a factor of at least 10 or at least 50. In certain embodiments, the pharmaceutical formulations are capable in a stem cell differentiation assay of forming hair cells from a cell population comprising vestibular supporting cells.

In certain embodiments, the vestibular tissue maintains Native Morphology. In certain embodiments, the vestibular tissue is in a subject. In certain embodiments, the contacting the vestibular tissue with the composition is achieved by administering the composition trans-tympanically to the subject. In certain embodiments, the contacting the vestibular tissue with the composition results in improved vestibular functioning of the subject.

In certain embodiments, the present disclosure is directed to a method of treating a subject who has, or is at risk of developing, a disease associated with absence or lack of certain tissue cells, the method comprising administering or causing to be administered to said subject a compound of the present disclosure.

In certain embodiments, the compound is dispersed in a biocompatible matrix. In certain embodiments, the biocompatible matrix is a biocompatible gel or foam. In certain embodiments, the compound is administered trans-tympanically to a vestibular tissue of the subject.

In certain embodiments, the present disclosure provides a method for expanding a population of vestibular cells in a vestibular tissue comprising contacting the vestibular tissue with (i) a compound of the present disclosure, and (ii) a TGF-β Inhibitor to form an expanded population of cells in the vestibular tissue.

Generation of Dermal Papilla Cells

In certain embodiments, the present disclosure is directed to a method of facilitating generation of Dermal Papilla Cells, the method comprising: administering a compound of the present disclosure, alone or in combination with a BMP inhibitor, to expand the population of Dermal Papilla Cells. In certain embodiments, the compounds can regenerate hair in a mammal. In certain embodiments, the Dermal Papilla Cells population is of an in vivo subject. In certain embodiments, the Dermal Papilla Cells population is of an in vivo subject for the treatment for alopecia. In certain embodiments, the present disclosure provides a method of generating Dermal Papilla Cells using of a compound of the present disclosure, alone or in combination with BMP inhibitor to proliferate Dermal Papilla Cells in an initial population in vivo, resulting in an expanded population of Dermal Papilla Cells.

Administration

The membrane of the round or oval is the biological barrier to the inner ear space and represents the major obstacle for the local treatment of hearing impairment. The administered drug must overcome this membrane to reach the inner ear space. The drug can operatively (e.g., injection through the tympanic membrane) be placed locally to the round or oval membrane and can then penetrate through the round or oval membrane. Substances that penetrate the round or oval typically distribute in the perilymph and thus reach the hair cells and supporting cells.

In certain embodiments, pharmaceutical formulations are adapted to administer the drug locally to the round or oval membrane. The pharmaceutical formulations may also contain a membrane penetration enhancer, which supports the passage of the agents mentioned herein through the round or oval membrane. Accordingly, liquid, gel or foam formulations may be used. It is also possible to apply the active ingredient orally or to employ a combination of delivery approaches.

Intratympanic (IT) delivery of drugs to the ear is increasingly used for both clinical and research purposes. Some groups have applied drugs in a sustained manner using microcatheters and microwicks, while the majority have applied them as single or as repeated IT injections (up to 8 injections over periods of up to 2 weeks 8).

Intratympanically applied drugs are thought to enter the fluids of the inner ear primarily by crossing the round or oval (RW) membrane. Calculations show that a major factor controlling both the amount of drug entering the ear and the distribution of drug along the length of the ear is the duration the drug remains in the middle ear space. Single, 'one-shot' applications or applications of aqueous solutions for few hours' duration result in steep drug gradients for the applied substance along the length of the cochlea and rapidly declining concentration in the basal turn of the cochlea as the drug subsequently becomes distributed throughout the ear.

Other injection approaches include by osmotic pump, or, by combination with implanted biomaterial, and more preferably, by injection or infusion. Biomaterials that can aid in controlling release kinetics and distribution of drug include hydrogel materials, degradable materials. One class of materials that is most preferably used includes in situ gelling materials. Other materials include collagen or other natural materials including fibrin, gelatin, and decellularized tissues. Gelfoam may also be suitable.

Delivery may also be enhanced via alternate means including but not limited to agents added to the delivered composition such as penetration enhancers, or could be through devices via ultrasound, electroporation, or high speed jet.

Methods described herein can also be used for inner ear cell types that may be produced using a variety of methods know to those skilled in the art including those cell types described in PCT Application No. WO2012103012 A1.

With regard to human and veterinary treatment, the amount of a particular agent(s) that is administered may be dependent on a variety of factors, including the disorder being treated and the severity of the disorder; activity of the specific agent(s) employed; the age, body weight, general health, sex and diet of the patient; the time of administration, route of administration, and rate of excretion of the specific agent(s) employed; the duration of the treatment; drugs used in combination or coincidental with the specific agent(s) employed; the judgment of the prescribing physician or veterinarian; and like factors known in the medical and veterinary arts.

The agents described herein may be administered in a therapeutically effective amount to a subject in need of treatment. Administration of compounds described herein can be via any of suitable route of administration, particularly by intratympanically. Other routes include ingestion, or alternatively parenterally, for example intravenously, intra-arterially, intraperitoneally, intrathecally, intraventricularly, intraurethrally, intrasternally, intracranially, intramuscularly, intranasally, subcutaneously, sublingually, transdermally, or by inhalation or insufflations, or topical by ear instillation for absorption through the skin of the ear canal and membranes of the eardrum. Such administration may be as a single or multiple oral dose, defined number of ear drops, or a bolus injection, multiple injections, or as a short- or long-duration infusion. Implantable devices (e.g., implantable infusion pumps) may also be employed for the periodic parenteral delivery over time of equivalent or varying dosages of the particular formulation. For such parenteral administration, the compounds are preferably formulated as a sterile solution in water or another suitable solvent or mixture of solvents. The solution may contain other substances such as salts, sugars (particularly glucose or mannitol), to make the solution isotonic with blood, buffering agents such as acetic, citric, and/or phosphoric acids and their sodium salts, and preservatives.

Compounds described herein can be administered by a number of methods sufficient to deliver the compound to the inner ear. Delivering a compound to the inner ear includes administering the compound to the middle ear, such that the compound may diffuse across the round or oval to the inner ear and administering a compound to the inner ear by direct injection through the round or oval membrane. Such methods include, but are not limited to auricular administration, by transtympanic wicks or catheters, or parenteral administration, for example, by intraauricular, transtympanic, or intracochlear injection.

In particular embodiments, the compounds, compositions and formulations of the disclosure are locally administered, meaning that they are not administered systemically.

In one embodiment, a syringe and needle apparatus is used to administer compounds or compositions to a subject using auricular administration. A suitably sized needle is used to pierce the tympanic membrane and a wick or catheter comprising the composition is inserted through the pierced tympanic membrane and into the middle ear of the subject. The device may be inserted such that it is in contact with the round or oval or immediately adjacent to the round or oval. Exemplary devices used for auricular administration include, but are not limited to, transtympanic wicks, transtympanic catheters, round or oval microcatheters (small catheters that deliver medicine to the round or oval), and Silverstein Microwicks™ (small tube with a "wick" through the tube to the round or oval, allowing regulation by subject or medical professional).

In another embodiment, a syringe and needle apparatus is used to administer compounds or compositions to a subject using transtympanic injection, injection behind the tympanic membrane into the middle and/or inner ear. The formulation may be administered directly onto the round or oval membrane via transtympanic injection or may be administered directly to the cochlea via intracochlear injection or directly to the vestibular organs via intravestibular injection.

In some embodiments, the delivery device is an apparatus designed for administration of compounds or compositions to the middle and/or inner ear. By way of example only: GYRUS Medical GmbH offers micro-otoscopes for visualization of and drug delivery to the round or oval niche; Arenberg has described a medical treatment device to deliver fluids to inner ear structures in U.S. Pat. Nos. 5,421,818; 5,474,529; and 5,476,446, each of which is incorporated by reference herein for such disclosure. U.S. patent application Ser. No. 08/874,208, which is incorporated herein by reference for such disclosure, describes a surgical method for implanting a fluid transfer conduit to deliver compositions to the inner ear. U.S. Patent Application Publication 2007/0167918, which is incorporated herein by reference for such disclosure, further describes a combined otic aspirator and medication dispenser for transtympanic fluid sampling and medicament application.

In some embodiments, composition provided herein is administered to a subject in need thereof once. In some embodiments, composition provided herein is administered to a subject in need thereof more than once. In some embodiments, a first administration of composition provided herein is followed by a second, third, fourth, or fifth administration of composition provided herein.

The number of times a compound is administered to a subject in need thereof depends on the discretion of a medical professional, the disorder, the severity of the disorder, and the subject's response to the formulation. In some embodiments, the compound disclosed herein is administered once to a subject in need thereof with a mild acute condition. In some embodiments, the compound disclosed herein is administered more than once to a subject in need thereof with a moderate or severe acute condition. In the case wherein the subject's condition does not improve, upon the doctor's discretion the compound may be administered chronically, that is, for an extended period of time, including throughout the duration of the subject's life in order to ameliorate or otherwise control or limit the symptoms of the subject's disease or condition.

In the case wherein the subject's status does improve, upon the doctor's discretion the compound may administered continuously; alternatively, the dose of drug being administered may be temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once the subject's hearing and/or balance has improved, a maintenance dose can be administered, if necessary. Subsequently, the dosage or the frequency of administration, or both, is optionally reduced, as a function of the symptoms, to a level at which the improved disease, disorder or condition is retained. In certain embodiments, subjects require intermittent treatment on a long-term basis upon any recurrence of symptoms.

In certain embodiments, the pharmaceutical formulations may also contain an additional agent selected from a Notch activator, HDAC inhibitor, a BMP4 antagonist, Noggin (Inhibits BMP4), Sox2, Vitamin D (calcitriol), Vitamin B (nicotinomide), Vitamin A, Vitamin C (pVc). Lgr4, p38/MAPK inhibition, ROCK inhibition, and/or Alk4/7 inhibition. In certain embodiments, the pharmaceutical formulations may also contain an epidermal growth factor (EGF), fibroblast growth factor (FGF), insulin-like growth factor (IGF), or a combination thereof.

Compositions with HDAC

In certain embodiments, the pharmaceutical formulations may also contain HDAC.

In certain embodiments, the pharmaceutical formulations containing HDAC can enhance the formation of Lgr5+ cells, control differentiation, control stemness, and replication or restore hearing and intestinal regeneration.

In certain embodiments, the HDAC inhibitor is Valproic acid or a prodrug, ester, salt form, or amide thereof.

In certain embodiments, the HDAC inhibitor is a carboxylic acid containing compound. In certain embodiments, the carboxylic acid containing compound is $C_6$-$C_{20}$ carboxylic acid, wherein the carboxylic acid comprises alkyl, alkenyl, or alkynyl.

In certain embodiments, the carboxylic acid containing compound is a substituted or unsubstituted $C_5$-$C_{20}$ straight, branched, or cyclic chain alkyl-$CO_2H$, substituted or unsubstituted $C_5$-$C_{20}$ straight, branched, or cyclic chain alkenyl-$CO_2H$ and substituted or unsubstituted $C_5$-$C_{20}$ straight, branched, or cyclic chain alkynyl-$CO_2H$. In certain embodiments, the carboxylic acid containing compound is a substituted $C_5$-$C_{20}$ straight or branched chain alkyl-$CO_2H$.

In certain embodiments, the carboxylic acid containing compound is a substituted $C_5$-$C_{20}$ straight or branched chain alkyl-$CO_2H$, wherein the substituent is —$NH_2$. In certain embodiments, the carboxylic acid containing compound is an amino substituted 2-propylpentanoic acid. In certain embodiments, the amino substituted 2-propylpentanoic acid is selected from the group consisting of 5-amino-2-propylpentanoic acid, 4-amino-2-propylpentanoic acid, 3-amino-2-propylpentanoic acid, and 2-amino-2-propylpentanoic acid.

In certain embodiments, the carboxylic acid containing compound is an unsubstituted $C_5$-$C_{20}$ straight or branched chain alkyl-$CO_2H$. In certain embodiments, the carboxylic acid containing compound is an unsubstituted $C_6$-$C_9$ branched straight chain alkyl-$CO_2H$. In certain embodiments, the carboxylic acid containing compound is an unsubstituted $C_8$-$C_9$ branched straight chain alkyl-$CO_2H$. In certain embodiments, the carboxylic acid containing compound is an unsubstituted $C_8$ branched straight chain alkyl-$CO_2H$.

In certain embodiments, the carboxylic acid containing compound is Valproic acid.

In certain embodiments, the carboxylic acid containing compound is in the form of a prodrug of an unsubstituted $C_8$ branched straight chain alkyl-$CO_2H$ wherein the prodrug is in the form of an amide or ester. In certain embodiments, the amide of unsubstituted $C_8$ branched straight chain alkyl-$CO_2H$ is the condensation product with an amino acid. In certain embodiments, the amide of Valproic acid is selected from the group consisting of

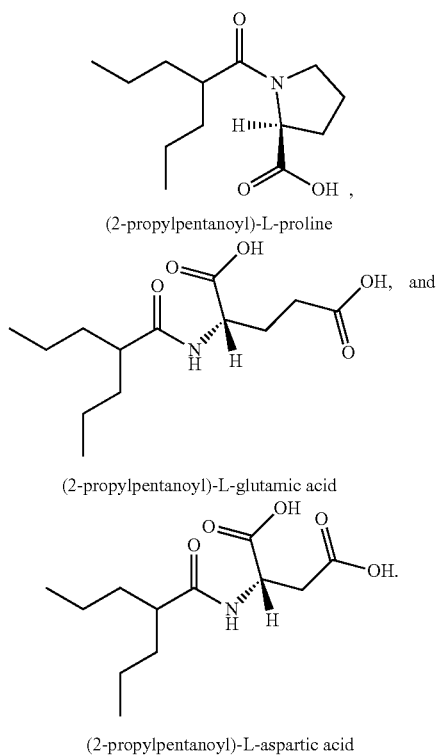

(2-propylpentanoyl)-L-proline, (2-propylpentanoyl)-L-glutamic acid, and (2-propylpentanoyl)-L-aspartic acid.

In some embodiments, the HDAC inhibitor is any one of the inhibitors listed in Table

TABLE 1

| Column A Class | Column B Agent | CAS Number |
|---|---|---|
| Aliphatic Acid | Valproic Acid | 99-66-1 |
| Aliphatic Acid | Phenyl butyrate | 1821-12-1 |
| Aliphatic Acid | Butyrate | 107-92-6 |
| Aliphatic Acid | 2-(prop-2-yn-1-yl)octanoic acid | 96017-59-3 |
| Aliphatic Acid | (S)-2-(prop-2-yn-1-yl)octanoic acid | 185463-37-0 |
| Aliphatic Acid | (R)-2-(prop-2-yn-1-yl)octanoic acid | 185463-38-1 |
| Aliphatic Acid | 2-(prop-2-yn-1-yl)heptanoic acid | 176638-49-6 |
| Aliphatic Acid | (S)-2-(prop-2-yn-1-yl) heptanoic acid | 185463-37-0 |
| Aliphatic Acid | (R)-2-(prop-2-yn-1-yl) heptanoic acid | 185463-38-1 |
| Aliphatic Acid | 2-fluoro-2-propyl Pentanoic acid | 197779-85-4 |
| Aliphatic Acid Ester | AN-9 | 122110-53-6 |
| Amine | 932718-22-4 | 932718-22-4 |
| Benzamide | Entinostat (MS-275) | 209783-80-2 |
| Benzamide | Mocetinostat (MGCD0103) | 726169-73-9 |

TABLE 1-continued

| Column A Class | Column B Agent | CAS Number |
|---|---|---|
| Benzamide | Tacedinaline | 112522-64-2 |
| Benzamide | BML-210 | 537034-17-6 |
| Benzamide | NKL 22 | 537034-15-4 |
| Benzamide | RGFP109 | 1215493-56-3 |
| Benzamide | RGFP136 | 1215493-97-2 |
| Benzamide | RGFP966 | 1357389-11-7 |
| Benzamide | 4SC-202 | 1186222-89-8 |
| Benzamide | HDAC Inhibitor IV | 537034-15-4 |
| Benzamide | Chidamide | 743438-44-0 |
| Benzamide | TC-H 106, HDAC Inhibitor VII | 937039-45-7 |
| Cyclic peptide | Romidepsin | 128517-07-7 |
| Cyclic peptide | Trapoxin A | 133155-89-2 |
| Cyclic peptide | HC Toxin | 83209-65-8 |
| Cyclic peptide | Apicidin | 183506-66-3 |
| Cyclic Peptide | Thailandepsin A | 1269219-30-8 |
| Cyclic peptide | Dihydrochlamydocin | 52574-64-8 |
| Epoxide | (−)-Depudecin | 139508-73-9 |
| Epoxide | Parthenolide | 20554-84-1 |
| Hydroxamate | Trichostatin A (TSA) | |
| Hydroxamate | Trichostatin A (TSA) | 58880-19-6 |
| Hydroxamate | SAHA (Zolinza, vorinostat) | 149647-78-9 |
| Hydroxamate | 4-iodo-SAHA | 1219807-87-0 |
| Hydroxamate | SBHA | 38937-66-5 |
| Hydroxamate | CBHA | 174664-65-4 |
| Hydroxamate | LAQ-824 | 591207-53-3 |
| Hydroxamate | PDX-101 (belinostat) | 866323-14-0 |
| Hydroxamate | LBH-589 (panobinostat) | 404950-80-7 |
| Hydroxamate | ITF2357 (Givinostat) | 497833-27-9 |
| Hydroxamate | PCI-34051 | 950762-95-5 |
| Hydroxamate | PCI-24781 (Abexinostat) | 783355-60-2 |
| Hydroxamate | Tubastatin A | 1252003-15-8 |
| Hydroxamate | CUDC-101 | 1012054-59-9 |
| Hydroxamate | Oxamflatin | 151720-43-3 |
| Hydroxamate | ITF2357 | 497833-27-9 |
| Hydroxamate | Bufexamac | 2438-72-4 |
| Hydroxamate | APHA Compound 8 | 676599-90-9 |
| Hydroxamate | HDAC Inhibitor XXIV | 854779-95-6 |
| Hydroxamate | Tubacin | 537049-40-4 |
| Hydroxamate | Butyrylhydroxamic acid | 4312-91-8 |
| Hydroxamate | MC 1568 | 852475-26-4 |
| Hydroxamate | SB939 (Pracinostat) | 929016-96-6 |
| Hydroxamate | 4SC-201 (Resminostat) | 864814-88-0 |
| Hydroxamate | Tefinostat (CHR-2845) | 914382-60-8 |
| Hydroxamate | CHR-3996 | 1256448-47-1 |
| Hydroxamate | NSC 57457 | 6953-61-3 |
| Hydroxamate | CG200745 | 936221-33-9 |
| Hydroxamate | ACY1215 | 1316214-52-4 |
| Hydroxamate | Nexturastat A | 1403783-31-2 |
| Hydroxamate | Droxinostat | 99873-43-5 |
| Hydroxamate | Scriptaid | 287383-59-9 |
| Hydroxamate | BRD9757 | 1423058-85-8 |
| Hydroxamate | HPOB | 1429651-50-2 |
| Hydroxamate | CAY10603 | 1045792-66-2 |
| Hydroxamate | HDAC6 Inhibitor III | 1450618-49-1 |
| Hydroxamate | M 344 | 251456-60-7 |
| Hydroxamate | 4-(dimethylamino)-N-[6-(hydroxyamino)-6-oxohexyl]-benzamide | 193551-00-7 |
| Hydroxamate | (S)-HDAC-42 | 935881-37-1 |
| Hydroxamate | HNHA | 926908-04-5 |
| Hydroxamate | Pyroxamide | 382180-17-8 |
| Hydroxamate | HDAC Inhibitor VI | 926908-04-5 |
| Hydroxamate | HDAC Inhibitor II | 174664-65-4 |
| Hydroxamate | LMK235 | 1418033-25-6 |
| Hydroxamate | HDAC-IN-1 | 1239610-44-6 |
| Hydroxamate | VAHA | 106132-78-9 |
| Ketone - CF3 | Compound 6e | 946500-31-8 |
| Ketone - CF3 | Compound 6H | 946500-39-6 |
| Ketone - CF3 | Compound 27 | 946499-86-1 |
| Ketone | Compound 43 | 891259-76-0 |
| Ketone - a-ketoamides | 436150-82-2 | 436150-82-2 |
| Polyketide | Ratjadone A | 163564-92-9 |
| Silylalcohol | 1587636-32-5 | 1587636-32-5 |
| Sulphonyl Urea | 960130-17-0 | 960130-17-0 |

TABLE 1-continued

HDAC Inhibitors

| Column A Class | Column B Agent | CAS Number |
|---|---|---|
| Sulphonamide | 1587636-33-6 | 1587636-33-6 |
| Sulphonamide | 329967-25-1 | 329967-25-1 |
| Thiol | 1428536-05-3 | 1428536-05-3 |
| Thiol | 908860-21-9 | 908860-21-9 |
| Thiol | 828920-13-4 | 828920-13-4 |
| Thiol | 1368806-68-1 | 1368806-68-1 |
| Thiol | 827036-76-0 | 827036-76-0 |
| Thioester | TCS HDAC6 20b | 956154-63-5 |
| Thioester | PTACH | 848354-66-5 |
| Thioester | KD 5170 | 940943-37-3 |
| Thioester | HDAC Inhibitor XXII | 848354-66-5 |
| Thioketone | SIRT1/2 Inhibitor VII | 143034-06-4 |
| Tropones | 46189-88-2 | 46189-88-2 |
| Tropones | 1411673-95-4 | 1411673-95-4 |
| Non classical | TMP269 | 1314890-29-3 |
| Non classical | Tasquinimod | 254964-60-8 |

Classes of HDAC inhibitors for use in various embodiments of the compositions and methods disclosed herein include but are not limited to those listed in Column A of Table 1. Specific HDAC inhibitors for use in various embodiments of the compositions and methods disclosed herein include but are not limited to those listed in Column B of Table 1. All agents listed in Table 1 column B are understood to include derivatives or pharmaceutically acceptable salts thereof. All classes listed in Table 1 column A are understood to include both agents comprising that class and derivatives or pharmaceutically acceptable salts thereof.

In certain embodiments, the amount of the carboxylic acid containing compound is between least 2 wt % (weight carboxylic acid containing compound/weight pharmaceutical composition) and 20 wt %. In certain embodiments, the composition comprises at least 4 wt % carboxylic acid. In certain embodiments, the composition comprises at least 8 wt % carboxylic acid. In certain embodiments, the composition comprises at least 12 wt % carboxylic acid. In certain embodiments, the composition comprises at least 16 wt % carboxylic acid. In certain embodiments, the composition comprises at least 20 wt % carboxylic acid.

Compositions with BMP Inhibitor

In certain embodiments, the pharmaceutical formulations may also contain BMP inhibitor. Examples of BMP inhibitors are shown herein. Other examples are described in WO2014138088A1 and WO2016054406A1, which are incorporated herein by reference in their entireties.

| BMP Inhibitor II | 1206711-16-1 |
|---|---|
| dorsomorphin | 866405-64-3 |
| ML347 | 1062368-49-3 |
| LDN-193189 | 1062368-24-4 |

Compositions with TGF-Beta Inhibitor

In certain embodiments, the pharmaceutical formulations may also contain TGF-beta inhibitor. In certain embodiments, the pharmaceutical formulations containing TGF-beta inhibitor can expand a population of vestibular cells in a vestibular tissue comprising contacting the vestibular tissue. In certain embodiments, the pharmaceutical formulations containing TGF-beta inhibitor are capable in a stem cell proliferation assay of increasing the number of supporting cells in a stem cell proliferation assay cell population by a factor of at least 10 or at least 50. In certain embodiments, the pharmaceutical formulations containing TGF-beta inhibitor are capable in a stem cell differentiation assay of forming hair cells from a cell population comprising vestibular supporting cells.

In one embodiment, the TGF-beta inhibitor is selected from 616452 (Repsox), Galunisertib (LY2157299), EW-719, IN-1130, EW-7203, EW-7195, SM16, R 268712, GW788388, and PF-03671148.

Exemplary TGF-β Inhibitors appear in Table 2. TGF-beta type I receptor inhibitors include but are not limited to 2-(3-(6-Methylpyridin-2-yl)-1H-pyrazol-4-yl)-1,5 napththyridine, [3-(Pyridin-2-yl)-4-(4-quinoyl)]-1H-pyrazole, and 3-(6-Methylpyridin-2-yl)-4-(4-quinolyl)-1-phenylthiocarbamoyl-1H-pyrazole, which can be purchased from Calbiochem (San Diego, Calif.). Other small molecule inhibitors include, but are not limited to, SB-431542 (see e.g., Halder et al., 2005; Neoplasia 7(5):509-521), SM16 (see e.g., Fu, K et al., 2008; Arteriosclerosis, Thrombosis and Vascular Biology 28(4):665), and SB-505124 (see e.g., Dacosta Byfield, S., et al., 2004; Molecular Pharmacology 65:744-52), among others.

TABLE 2

TGF-β Inhibitors

| Class | Agent | CAS Number | Alternative Name |
|---|---|---|---|
| Tgf-beta-R1 inhibitor | LY-364947 | 396129-53-6 | 616451, TGF-β RI Kinase Inhibitor I, [3-(Pyridin-2-yl)-4-(4-quinonyl)]-1H-pyrazole, ALK5 Inhibitor I, LY-364947, HTS-466284 |
| Tgf-beta-R1 inhibitor | Repsox | 446859-33-2 | 616452, TGF-β RI Kinase Inhibitor II, 2-(3-(6-Methylpyridin-2-yl)-1H-pyrazol-4-yl)-1,5-naphthyridine |
| Tgf-beta-R1 inhibitor | SB-505124 | 356559-13-2 | 616453, TGF-β RI Kinase Inhibitor III, CAS 356559-13-2 2-(5-Benzo[1,3]dioxol-4-yl-2-tert-butyl-1H-imidazol-4-yl)-6-methylpyridine, HCl, ALK5 Inhibitor III, |
| Tgf-beta-R1 inhibitor | A-83-01 | 909910-43-6 | 616454, TGF-β RI Kinase Inhibitor IV - 3-(6-Methylpyridin-2-yl)-4-(4-quinolyl)-1-phenylthiocarbamoyl-1H-pyrazole, A-83-01, ALK5 Inhibitor IV |
| Tgf-beta-R1 inhibitor | SD-208 | 627536-09-8 | 616456, TGF-β RI Kinase Inhibitor V, 2-(5-Chloro-2-fluorophenyl)pteridin-4-yl)pyridin-4-yl amine, SD-208, ALK5 Inhibitor V |

TABLE 2-continued

TGF-β Inhibitors

| Class | Agent | CAS Number | Alternative Name |
|---|---|---|---|
| Tgf-beta-R1 inhibitor | SB-431542 | 301836-41-9 | 616461, TGF-β RI Kinase Inhibitor VI, 4-[4-(3,4-Methylenedioxyphenyl)-5-(2-pyridyl)-1H-imidazol-2-yl]benzamide, Dihydrate, 4-[4-(1,3-Benzodioxol-5-yl)-5-(2-pyridyl)-1H-imidazol-2-yl]benzamide, Dihydrate |
| Tgf-beta-R1 inhibitor | TGF-β RI Kinase Inhibitor VII | 666729-57-3 | 616458, TGF-β RI Kinase Inhibitor VII, 1-(2-((6,7-Dimethoxy-4-quinolyl)oxy)-(4,5-dimethylphenyl)-1-ethanone, ALK5 Inhibitor VII |
| Tgf-beta-R1 inhibitor | SB-525334 | 356559-20-1 | 616459, TGF-β RI Kinase Inhibitor VIII - SB-525334, 6-(2-tert-Butyl-5-(6-methyl-pyridin-2-yl)-1H-imidazol-4-yl)-quinoxaline, ALK5 Inhibitor VIII |
| Tgf-beta-R1 inhibitor | TGF-β RI Kinase Inhibitor IX | 1117684-36-2 | 616463, TGF-β RI Kinase Inhibitor IX, 4-((4-((2,6-Dimethylpyridin-3-yl)oxy)pyridin-2-yl)amino)benzenesulfonamide, ALK5 Inhibitor IX |
| Tgf-beta-R1 inhibitor | GW788388 | 452342-67-5 | 4-(4-(3-(pyridin-2-yl)-1H-pyrazol-4-yl)pyridin-2-yl)-N-(tetrahydro-2H-pyran-4-yl)benzamide |
| Tgf-beta-R1 inhibitor | LY2109761 | 700874-71-1 | 7-(2-morpholinoethoxy)-4-(2-(pyridin-2-yl)-5,6-dihydro-4H-pyrrolo[1,2-b]pyrazol-3-yl)quinoline |
| Tgf-beta-R1 inhibitor | Galunisertib (LY2157299) | 700874-72-2 | 4-(2-(6-methylpyridin-2-yl)-5,6-dihydro-4H-pyrrolo[1,2-b]pyrazol-3-yl)quinoline-6-carboxamide |
| Tgf-beta-R1 inhibitor | EW-7197 | 1352608-82-2 | N-(2-fluorophenyl)-5-(6-methyl-2-pyridinyl)-4-[1,2,4]triazolo[1,5-a]pyridin-6-yl-1H-imidazole-2-methanamine |
| Tgfb production inhibitor | Pirfenidone | 53179-13-8 | 5-methyl-1-phenyl-2(1H)-Pyridinone, |
| Tgf-beta-R1 inhibitor | K02288 | 1431985-92-0 | 3-[(6-Amino-5-(3,4,5-trimethoxyphenyl)-3-pyridinyl]phenol |
| Tgf-beta-R1 inhibitor | D 4476 | 301836-43-1 | 4-[4-(2,3-Dihydro-1,4-benzodioxin-6-yl)-5-(2-pyridinyl)-1H-imidazol-2-yl]benzamide |
| Tgf-beta-R1 inhibitor | R 268712 | 879487-87-3 | 4-[2-Fluoro-5-[3-(6-methyl-2-pyridinyl)-1H-pyrazol-4-yl]phenyl]-1H-pyrazole-1-ethanol |
| Other | ITD 1 | 1099644-42-4 | 4-[1,1'-Biphenyl]-4-yl-1,4,5,6,7,8-hexahydro-2,7,7-trimethyl-5-oxo-3-quinolinecarboxylic acid ethyl ester |
| Smad3 inhibitor | SIS3 | 1009104-85-1 | 1,2,3,4-Tetrahydro-6,7-dimethoxy-2-[(2E)-3-(1-phenyl-1H-pyrrolo [2,3-b]pyridin-3-yl)-1-oxo-2-propenyl]-isoquinoline hydrochloride |
| Tgf-beta-R1 inhibitor | A77-01 | 909910-42-5 | 4-[5-(6-methylpyridin-2-yl)-1H-pyrazol-4-yl]quinoline |
| Tgf-beta-R1 inhibitor | SM16 | 614749-78-9 | 4-(5-(benzo[d][1,3]dioxol-5-yl)-4-(6-methylpyridin-2-yl)-1H-imidazol-2-yl)bicyclo[2.2.2]octane-1-carboxamide |
| Tgf-beta-R1 inhibitor | LY-550410 | 737791-20-7 | 5,6-dihydro-2-(2-pyridinyl)-4H-pyrrolo[1,2-b]pyrazol-3-yl]-Quinoline |
| Tgf-beta-R1 inhibitor | LY-580276 | 476475-07-7 | 3-(4-fluorophenyl)-5,6-dihydro-2-(6-methyl-2-pyridinyl)-4H-Pyrrolo[1,2-b] pyrazole |
| Tgf-beta-R1 inhibitor | EW-7203 | 1383123-98-5 | 3-[[[4-(6-methyl-2-pyridinyl)-5-[1,2,4]triazolo[1,5-a]pyridin-6-yl-2-thiazolyl]aminolmethyl]-Benzonitrile |
| Tgf-beta-R1 inhibitor | EW-7195 | 1352609-28-9 | 3-[[[5-(6-methyl-2-pyridinyl)-4-[1,2,4]triazolo[1,5-a]pyridin-6-yl-1H-imidazol-2-yl]methyl]amino]-Benzonitrile |
| Tgf-beta-R1 inhibitor | GW6604 | 452342-37-9 | Pyridine, 2-phenyl-4-[3-(2-pyridinyl)-1H-pyrazol-4-yl]- |
| Tgf-beta-R1 inhibitor | Cmpd 3d | 733806-89-8 | 4-Quinazolinamine, 2-(6-methyl-2-pyridinyl)-N-4-pyridinyl- |
| Tgf-beta-R1 inhibitor | LY-566578 | 607738-00-1 | Pyridine, 2-[4-(4-fluorophenyl)-1H-pyrazol-3-yl]-6-methyl- |
| Tgf-beta-R1 inhibitor | Cmpd 5 | 607738-02-3 | Phenol, 4-[3-(6-methyl-2-pyridinyl)-1H-pyrazol-4-yl] |
| Tgf-beta-R1 inhibitor | Cmpd 3 | 676331-30-9 | Quinoline, 7-ethoxy-4-[3-(2-pyridinyl)-1H-pyrazol-4-yl]- |

TABLE 2-continued

TGF-β Inhibitors

| Class | Agent | CAS Number | Alternative Name |
|---|---|---|---|
| Tgf-beta-R1 inhibitor | Cmpd 8b | 705263-50-9 | 1H-Benzimidazole, 6-[5,6-dihydro-2-(2-pyridinyl)-4H-pyrrolo[1,2-b]pyrazol-3-yl]- |
| Tgf-beta-R1 inhibitor | Cmpd 4b | 1308760-90-8 | N-(3-cyanophenyl)-3-(6-methyl-2-pyridinyl)-4-(6-quinolinyl)-1H-Pyrazole-1-acetamide |
| Tgf-beta-R1 inhibitor | Cmpd 21b | 1607465-38-2? | 1H-Pyrazole-1-acetamide, N-(3-cyanophenyl)-3-(6-methyl-2-pyridinyl)-4-[1,2,4]triazolo[1,5-a]pyridin-6-yl |
| Tgf-beta-R1 inhibitor | PF-03671148 | 1378524-25-4 | 3-methyl-6-[1-(6-methyl-2-pyridinyl)-1H-pyrazol-5-yl]-4(3H)-Quinazolinone, |
| Tgf-beta-R1 inhibitor | SB-203580 | 152121-47-6 | Pyridine, 4-[4-(4-fluorophenyl)-2-[4-(methylsulfinyl)phenyl]-1H-imidazol-5-yl]- |
| Tgf-beta-R1 inhibitor | SB-202190 | 152121-30-7 | 4-[4-(4-Fluorophenyl)-5-(4-pyridinyl)-1H-imidazol-2-yl]phenol |
| Tgf-beta-R1 inhibitor | IN-1130 | 868612-83-3 | 3-[[5-(6-methyl-2-pyridinyl)-4-(6-quinoxalinyl)-1H-imidazol-2-yl]methyl]-Benzamide, |
| Tgf-beta-R1 inhibitor | IN-1233 | 1093952-95-4 | 3-[[5-(6-methyl-2-pyridinyl)-4-(6-quinolinyl)-1H-imidazol-2-yl]methyl]-Benzamide, |
| Tgf-beta-R1 inhibitor | Cmpd 16i | 864375-44-0 | [[4-(6-benzothiazolyl)-5-(4-methyl-2-thiazolyl)-1H-imidazol-2-yl]methyl]-2-methylpropyl ester Carbamic acid |
| Tgf-beta-R1 inhibitor | LDN-214117 | 1627503-67-6 | 1-[4-[6-methyl-5-(3,4,5-trimethoxyphenyl)-3-pyridinyl]phenyl]-Piperazine |
| Tgf-beta-R1 inhibitor | LDN-193189 | 1627503-67-6 | CAS 1062368-24-4,4-[6-[4-(1-piperazinyl)phenyl]pyrazolo[1,5-a]pyrimidin-3-yl]-Quinoline |
| Tgf-beta-R1 inhibitor | Cmpd 12b | 1415663-82-9 | 2-N-[(3-fluorophenyl)methyl]-4-(6-methyl-2-pyridinyl)-5-[1,2,4]triazolo[1,5-a]pyridin-6-yl Thiazolamine |
| Tgf-beta-R1 inhibitor | Cmpd 6d | 1630024-29-1 | 5-[[2-cyclopropyl-6-(4-fluorophenyl)imidazo[2,1-b]-1,3,4-thiadiazol-5-yl]methylene]-4-oxo-2-thioxo-3-Thiazolidineacetic acid |
| Tgf-beta-R1 inhibitor | SD-093 | | Structure unknown |
| Tgf-beta-R1 inhibitor | Ki-26894 | | Structure unknown |
| Tgf-beta-R1 inhibitor | NPC-30345 | | Structure unknown |
| Tgf-beta-R1 inhibitor | SX-007 | | Structure unknown |
| Tgf-beta-R1 inhibitor | SKI-2162 | | Structure unknown |
| Other | Asiaticoside | 16830-15-2 | |
| Tgf-beta antibody | ID11 | | |
| Tgf-beta antibody | 2G7 | | |
| Tgf-beta antibody | GC-1008 | | Fresolimumab |
| Tgf-beta antibody | CAT-152 | | Lerdelimimab |
| Tgf-beta antibody | CAT-192 | | Metelimumab |
| TGf-beta Receptor antibody | PF-03446962 | | |
| Tgf-beta antibody | SR-2F | | |
| Tgf-beta antibody | 2G7 | | |
| Tgf-beta antibody | LY2382770 | | |
| Tgf-beta antibody | IMC-TR1 | | |
| Tgf-beta antibody | STX-100 | | |
| TGF-beta antagonist Recombinant protein | TGF-PRII: Fc betaglycan/TGF-PRIII | | |
| Oligonucleotide inhibitor | AP12009 | | Trabedersen, antisense molecule |
| Oligonucleotide inhibitor | AP11014 | | |
| Oligonucleotide inhibitor | AP15012 | | |

TABLE 2-continued

TGF-β Inhibitors

| Class | Agent | CAS Number | Alternative Name |
|---|---|---|---|
| Is this TGF b inhibitor/YES | LY-573636 | 519055-62-0 | N-[(5-bromo-2-thienyl)sulfonyl]-2,4-dichloro-Benzamide |
| | pyrrole-imidazole polyamide | | Gene silencing |
| | U.S. Pat. No. 7,087,626 | | Pyrrole derivatives as pharmaceutical agents |
| | U.S. Pat. No. 6,476,031 | | Quinazoline derivatives as medicaments |
| | U.S. Pat. No. 7,723,486, and EP 0945464 | | Antibodies to TGF-β |
| Peptide | Tryptopeptin A | 1644153-72-9 | |
| Peptide | Trx-xFoxHlb | | Smad-interacting peptide aptamers |
| Peptide | Trx-Lefl | | |
| Peptide | Distertide (pl44) | | |
| Peptide | pl7 | | |
| Peptide | LSKL | | |
| dihydropyrrlipyrazole-based scaffold | See US Patent U.S. Pat. No. 8,298,825 B1 | | |
| imidazole-based scaffold | See US Patent U.S. Pat. No. 8,298,825 B1 | | |
| pyrazolopyridine-based scaffold | See US Patent U.S. Pat. No. 8,298,825 B1 | | |
| pyrazole-based scaffold | | | See US Patent U.S. Pat. No. 8,298,825 B1 |
| imidazopyridine-based scaffold | See US Patent U.S. Pat. No. 8,298,825 B1 | | |
| triazole-based scaffold | | | See US Patent U.S. Pat. No. 8,298,825 B1 |
| pyridopyrimidine-based scaffold | See US Patent U.S. Pat. No. 8,298,825 B1 | | |
| pyrrolopyrazole-based scaffold | See US Patent U.S. Pat. No. 8,298,825 B1 | | |
| isothiazole-based scaffold | See US Patent U.S. Pat. No. 8,298,825 B1 | | |
| oxazole-based scaffold | See US Patent U.S. Pat. No. 8,298,825 B1 | | |

Compositions with Poloxamers

In certain embodiments, the present disclosure provides a pharmaceutical composition comprising: a) a compound of the present disclosure and b) a poloxamer.

In certain embodiments, the pH of the pharmaceutical composition is between about 5 and about 9. In certain embodiments, the pH of the pharmaceutical composition is about 5, 6, 7, 8, or 9.

In certain embodiments, the solubility of the compound in the presence of the poloxamer is about 3-fold higher than the solubility of the compound at the same pH in the absence of poloxamer. In certain embodiments, the solubility of the compound in the presence of the poloxamer is about 2-, 3-, 4- or 5-fold higher than the solubility of the compound at the same pH in the absence of poloxamer.

In certain embodiments, the pharmaceutical formulations may also contain a poloxamer. Poloxamers are nonionic triblock copolymers composed of a central hydrophobic chain of polyoxypropylene (poly(propylene oxide)) flanked by two hydrophilic chains of polyoxyethylene (poly(ethylene oxide)). Poloxamers are often considered "functional excipients" because they are essential components and play an important role in a formulation.

In some embodiments, the poloxamer comprises at least one of Poloxamer 124, Poloxamer 188, Poloxamer 237, Poloxamer 338 or Poloxamer 407. In some embodiments, the poloxamer comprises mixtures of two or more of Poloxamer 124, Poloxamer 188, Poloxamer 237, Poloxamer 338 or Poloxamer 407. In some embodiments, the mixture of two or more poloxamers comprise Poloxamer 407 and Poloxamer 124. In another embodiment the Poloxamer comprises at least one of Poloxamer 188 and Poloxamer 407 or mixtures thereof. In some embodiments, the poloxamer is Poloxamer 407.

In some embodiments, the poloxamer is in a concentration between about 5 wt % and about 25 wt % relative to the composition. In some embodiments, the poloxamer is in a concentration between about 10 wt % and about 23 wt % relative to the composition. In some embodiments, the poloxamer is in a concentration between about 15 wt % and about 20 wt % relative to the composition. In some embodiments, the poloxamer is in a concentration is approximately 17 wt % relative to the composition. In some embodiments, the poloxamer is in a concentration is approximately 21 wt % relative to the composition.

In some embodiments, the poloxamer can be in a concentration between 21 wt % and 40 wt % relative to the composition. In another embodiment the poloxamer is in a concentration between 21 wt % and 30 wt % relative to the composition. In another embodiment the poloxamer is in a concentration between 23 wt % and 29 wt % relative to the composition. In another embodiment the poloxamer is in a concentration between 23 wt % and 27 wt % relative to the composition. In another embodiment the poloxamer is in a concentration of 25 wt % relative to the composition.

In some embodiments, the gelation temperature of the pharmaceutical composition is greater than about 10° C. In some embodiments, the gelation temperature of the pharmaceutical composition is between about 11° C. and about 32° C. In some embodiments, the gelation temperature of the pharmaceutical composition is between about 15° C. and about 30° C. In some embodiments, the gelation temperature of the pharmaceutical composition is between about 20° C. and about 28° C. In some embodiments, the gelation temperature of the pharmaceutical composition is between about 24° C. and about 26° C.

In some embodiments, the gelation temperature of the pharmaceutical composition is about 15° C. In some embodiments, the gelation temperature of the pharmaceutical composition is about 20° C. In some embodiments, the gelation temperature of the pharmaceutical composition is about 24° C. In some embodiments, the gelation temperature of the pharmaceutical composition is about 26° C. In some embodiments, the gelation temperature of the pharmaceutical composition is about 28° C. In some embodiments, the gelation temperature of the pharmaceutical composition is about 30° C. In some embodiments, the gelation temperature of the pharmaceutical composition is about 32° C.

In certain embodiments, the present disclosure provides a pharmaceutical composition having a gelation temperature greater than 10° C., the composition comprising: a) a pharmaceutically active compound of the present disclosure; b) a poloxamer at greater than or equal to 21 wt % of the pharmaceutical composition; and c) a HDAC inhibitor; wherein the pharmaceutical composition has a gelation temperature of greater than 10° C.

In certain embodiments, the present disclosure provides a pharmaceutical composition having a gelation temperature greater than 10° C., the composition comprising: a) a pharmaceutically active compound of the present disclosure; b) a poloxamer at greater than or equal to 21 wt % of the pharmaceutical composition; and c) a carboxylic acid containing compound; wherein the pharmaceutical composition has a gelation temperature of greater than 10° C.

EXAMPLES

Experimental Procedures

Synthesis of Intermediate 2.

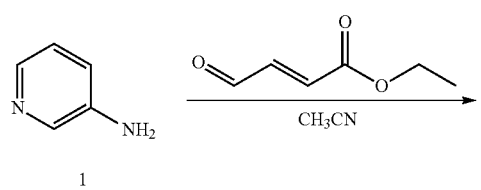

To a solution of intermediate 1 (20 g, 213 mmol) in MeCN (540 ml) was ethyl (E)-4-oxo-butenoate (28.6 g, 223 mmol). The reaction mixture was heated to 80° C. and stirred for 6 hrs. The reaction mixture was concentrated under reduced pressure, the residue was purified by flash column chromatography (eluted with Dichloromethane/MeOH from 1:0 to 200:1) to give the crude intermediate 2 (25 g) as brown solid.

Synthesis of Intermediate 3A.

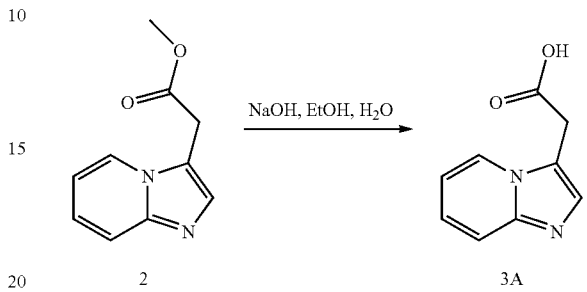

To a solution of intermediate 2 (1 g, 4.9 mmol) in EtOH (6 ml) was added NaOH (0.6 g, 14.7 mmol) in H$_2$O (6 ml). The mixture was stirred at room temperature for overnight. The solvent was concentrated in vacuum, the residue was dissolved in EtOH, filtered. The solvent was concentrated in vacuum again to give intermediate 3A as a brown solid (1 g, crude).

Synthesis of Intermediate 3.

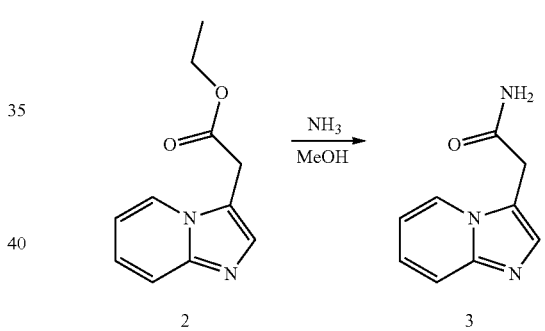

To a solution of crude intermediate 2 (25 g) in MeOH (100 ml) was added NH$_3$/MeOH (6 M, 100 ml). The reaction mixture was stirred at room temperature overnight. The mixture was poured into EtOAc (500 ml), and then filtered. The filter cake was dried in vacuo to give intermediate 3 (13 g, 35% for two steps) as a brown solid.

$^1$H NMR (DMSO-d$_6$, 400 MHz): δ (ppm) 8.30 (d, J=6.8 Hz, 1H), 7.60 (s br, 1H), 7.54 (d, J=5.2 Hz, 1H), 7.41 (s, 1H), 7.19-7.23 (m, 1H), 7.06 (s br, 1H), 6.89-6.93 (m, 1H), 3.80 (s, 2H).

Synthesis of Intermediate 5.

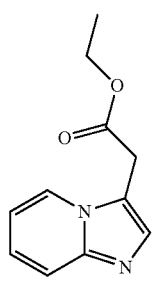

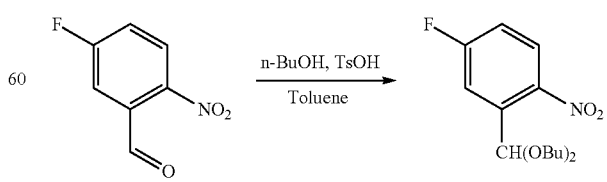

To a solution of intermediate 4 (100 g, 0.59 mol) in dry toluene (890 ml) was added n-BuOH (131.6 g, 1.78 mol) and TsOH (10 g) at room temperature. The mixture was stirred at 120° C. for overnight, and removed the water using a Dean-stark apparatus. TLC (petroleum ether/EtOAc=5/1) showed the reaction was completed. The mixture was concentrated in vacuum to give crude intermediate 5. The crude intermediate 5 was purified by flash column chromatography (eluted with petroleum ether/EtOAc from 100:1 to 20:1) to give intermediate 5 (120 g, 67.8%) as a yellow oil.

$^1$H NMR (CDCl$_3$, 400 MHz): δ (ppm) 7.89-7.92 (dd, 1H, J=4.8 Hz, 8.8 Hz), 7.51-7.54 (dd, 1H, J=2.8 Hz, 9.6 Hz), 7.09-7.14 (m, 1H), 6.04 (s, 1H), 3.50-3.56 (m, 4H), 1.55-1.62 (m, 4H), 1.33-1.42 (m, 4H), 0.83-0.93 (m, 6H).

Synthesis of Intermediate 6.

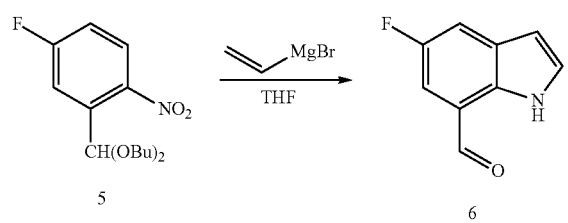

To a solution of intermediate 5 (50 g, 0.17 mol) in dry THF (1500 ml) was added vinylmagnesium bromide solution (1 M, 668.8 ml, 668.8 mmol) dropwise at −40° C. The mixture was stirred at −40° C. for 1 hr. TLC (petroleum ether/EtOAc=5/1) showed the reaction was completed Then the mixture was poured into aq. NH$_4$Cl, extracted with EtOAc (300 ml×3), the organic phases were concentrated to give crude compound. The crude compound was purified by flash column chromatography (eluted with petroleum ether/EtOAc from 100:1 to 20:1) to give the compound (24 g) as yellow oil. To a solution of the compound (24 g) in THF (100 ml) was added HCl (0.5 N, 80 ml) dropwise at room temperature. The mixture was stirred at room temperature for 1 hr. TLC (petroleum ether/EtOAc=5/1) showed the reaction was completed. The mixture was adjusted PH=10 with aq. NaOH, extracted with EtOAc (300 ml×3), concentrated in vacuum to give intermediate 6 (16 g, 58.8%) as yellow solid.

$^1$H NMR (CDCl$_3$, 400 MHz): δ (ppm) 10.06 (s, 1H), 7.62 (dd, 1H, J=2 Hz, 9.2 Hz), 7.38-7.41 (m, 2H), 6.60 (t, 1H, J=2.4 Hz).

Synthesis of Intermediate 7.

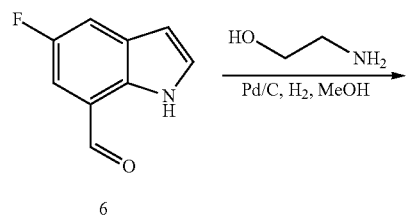

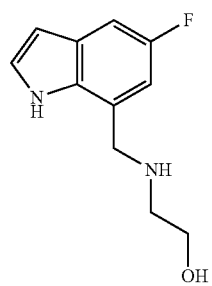

To a solution of intermediate 6 (140 g, 0.86 mol) in MeOH (2100 ml) was added 2-aminoethanol (78 g, 1.3 mol) and Pd/C (14 g) at room temperature under N$_2$. The mixture was stirred at room temperature for 2 hours under N$_2$. Then the mixture was stirred at room temperature for overnight under H$_2$. The mixture was filtered, concentrated to give intermediate 7 (200 g, crude) as a yellow oil, which was used directly for the next step without purification.

Synthesis of Intermediate 8.

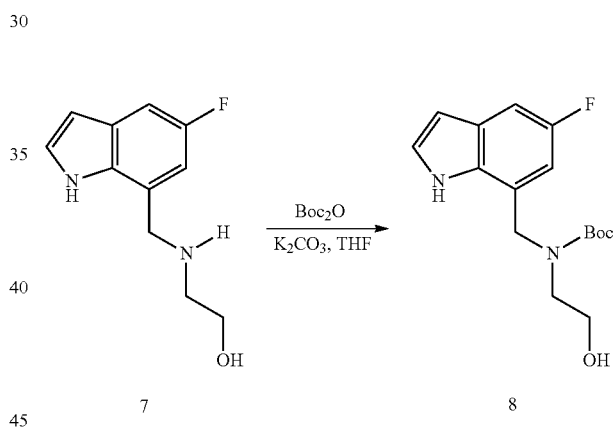

A mixture of intermediate 7 (90 g, crude) and K$_2$CO$_3$ (467 ml, 1 M) in THF (1300 ml) was added Boc$_2$O (141 g) at room temperature. The mixture was stirred at room temperature for overnight. TLC (dichloromethane/MeOH=10/1) showed the reaction was completed Then H$_2$O was added, extracted with EtOAc (500 ml×3). The combined organic phases were washed with brine, dried over Na$_2$SO$_4$ and concentrated in vacuum. The residue was purified by flash column chromatography (eluted with petroleum ether/EtOAc from 10:1 to 1:1) to give intermediate 8 (66.6 g, 56% for two steps) as yellow oil.

$^1$H NMR (CDCl$_3$, 400 MHz): δ (ppm) 10.17 (s, 1H), 7.23-7.26 (m, 2H), 6.78-6.82 (dd, 1H, J=9.2 Hz, J=2 Hz), 6.48-6.50 (t, 1H, J=2.4 Hz), 4.67 (s, 2H), 3.66-3.71 (m, 2H), 3.25-35 (m, 2H), 1.40 (s, 9H).

Synthesis of Intermediate 9.

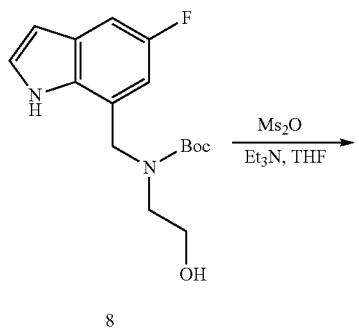

8

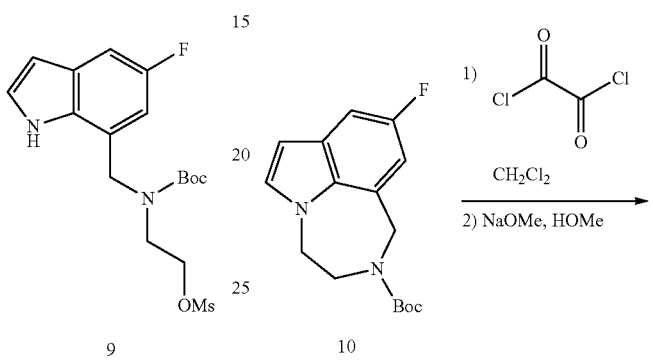

9 → 10

To a solution of intermediate 8 (50 g, 0.26 mol) in THF (1000 ml) was added Et₃N (79 g, 0.79 mol) and Ms₂O (55 g, 0.32 mol) at 0° C. under N₂. The mixture was stirred at 0° C. for 2 hrs. TLC (petroleum ether/EtOAc=3/1) showed the reaction was completed. Then it was poured into ice-water and extracted with EtOAc (400 ml×2). The combined organic phases were washed with brine, dried over Na₂SO₄ and concentrated in vacuum to give intermediate 9 (50 g, 79%) as yellow oil.

¹H NMR (CDCl₃, 400 MHz): δ (ppm) 10.08 (bs, 1H), 7.24-7.29 (m, 2H), 6.81-6.84 (m, 1H), 6.49-6.50 (d, 1H, J=2.4 Hz), 4.67 (s, 2H), 4.28-4.31 (m, 2H), 3.48-3.52 (m, 2H), 2.79 (s, 3H), 1.51 (s, 9H).

Synthesis of Intermediate 10.

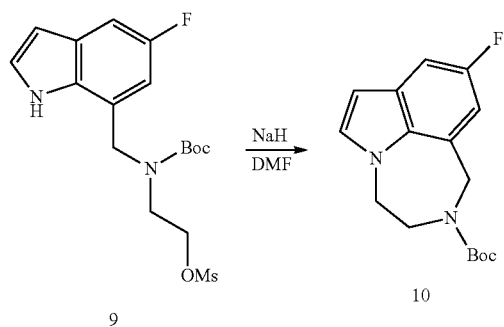

9 → 10

A solution of intermediate 9 (65 g, 0.19 mol) in DMF (722 ml) was added NaH (60%, 11.5 g, 0.29 mol) at 0° C. The mixture was stirred at 0° C. for 1 hour under N₂. TLC (petroleum ether/EtOAc=3/1) showed the reaction was completed. Then the mixture was poured into ice-water and extracted with EtOAc (500 ml×4). The combined organic phases were washed with water, brine, dried over Na₂SO₄ and concentrated in vacuum. The residue was purified by flash column chromatography (eluted with petroleum ether/EtOAc from 50:1 to 10:1) to give intermediate 10 (26 g, 53.2%) as yellow solid.

¹H NMR (CDCl₃, 400 MHz): δ (ppm) 7.14-7.16 (d, 1H, J=8 Hz), 7.07 (s, 1H), 6.72-6.83 (m, 1H), 6.48-6.49 (d, 1H, J=2.8 Hz), 4.84-4.76 (s, 2H), 4.24-4.25 (m, 2H), 3.94 (m, 2H), 1.45-1.48 (m, 9H).

Synthesis of Intermediate 11.

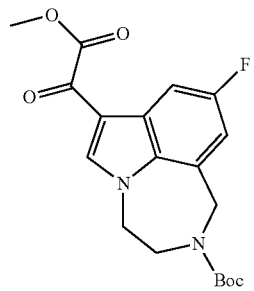

11

A solution of intermediate 10 (27.5 g, 95.0 mmol) in dichloromethane (900 ml) was added (COCl)₂ (18 g, 142 mmol) at 0° C. under N₂. The mixture was stirred at 0° C. for 2 hrs. TLC (petroleum ether/EtOAc=1/1) showed the reaction was completed. Then a solution of NaOMe (13.4 g, 247 mmol) in MeOH (40.8 ml) was added at −60° C. under N₂. The mixture was stirred at room temperature for 1 hr. Water was added, extracted with dichloromethane (200 ml×3). The combined organic phases were washed with water, brine, dried over Na₂SO₄ and concentrated in vacuum. The residue was purified by flash column chromatography (eluted with petroleum ether/EtOAc from 20:1 to 1:1) to give intermediate 11 (20 g, 56%) as white solid.

¹H NMR (CDCl₃, 400 MHz): δ (ppm) 8.37 (s, 1H), 8.02-8.04 (d, 1H, J=8.4 Hz), 6.84-6.91 (m, 1H), 4.80-4.90 (m, 2H), 4.44 (bs, 2H), 3.91-3.98 (m, 5H), 1.41-1.46 (m, 9H).

Synthesis of Intermediate 12.

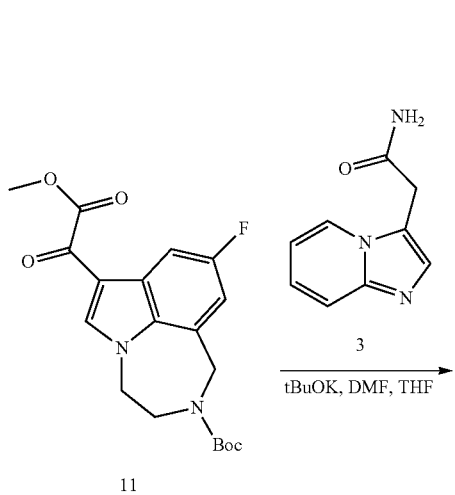

A solution of intermediate 11 (10 g, 26.5 mmol) and intermediate 3 (4.6 g, 26.5 mmol) in DMF (120 ml) was added a solution of tBuOK (7.4 g, 66.2 mmol) in THF (100 ml) at 0-10° C. The mixture was stirred at 0-10° C. for 15 min. TLC (petroleum ether/EtOAc=1/1) showed the reaction was completed. Then the mixture was poured into ice-water and extracted with EtOAc (100 ml×4). The combined organic phases were washed with water, brine, dried over $Na_2SO_4$ and concentrated in vacuum. The residue was purified by flash column chromatography (eluted with petroleum ether/EtOAc from 20:1 to 1:1) to give intermediate 12 (7 g, 52.5%) as red solid.

$^1$H NMR (DMSO-$d_6$, 400 MHz): δ (ppm) 11.07 (s, 1H), 8.02-8.01 (d, 1H, J=4 Hz), 8.96 (s, 1H), 7.61-7.63 (t, 1H, J=8.8 Hz), 7.45 (s, 1H), 7.17 (s, 1H), 6.57-6.64 (m, 1H), 6.47-6.49 (d, 1H, J=8 Hz), 5.77-5.80 (d, 1H J=8.4 Hz), 4.73 4.78 (2H), 4.52 (bs, 2H), 3.96 (bs, 2H), 1.25-1.44 (m, 9H).

Synthesis of Core 3.

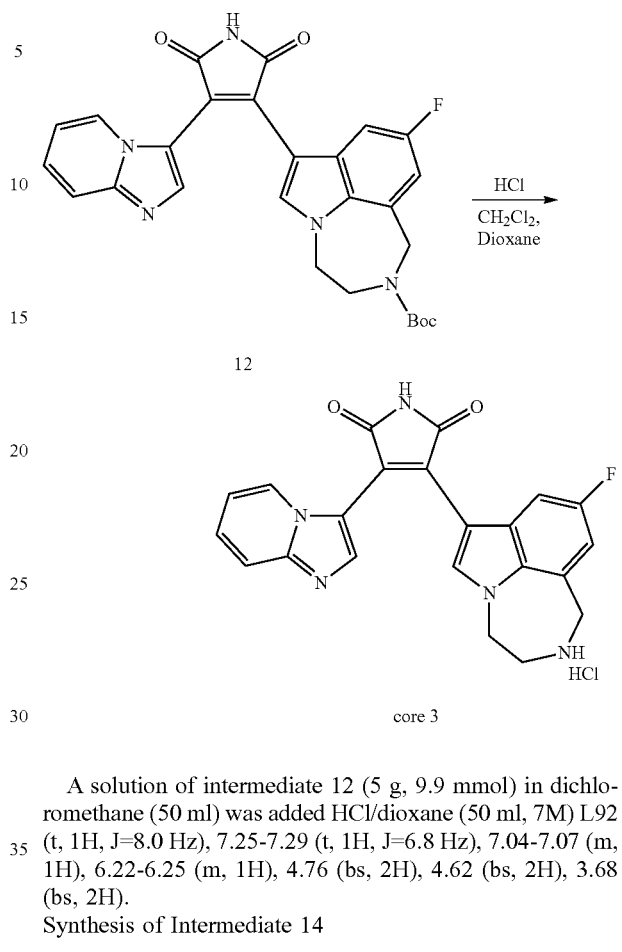

A solution of intermediate 12 (5 g, 9.9 mmol) in dichloromethane (50 ml) was added HCl/dioxane (50 ml, 7M) L92 (t, 1H, J=8.0 Hz), 7.25-7.29 (t, 1H, J=6.8 Hz), 7.04-7.07 (m, 1H), 6.22-6.25 (m, 1H), 4.76 (bs, 2H), 4.62 (bs, 2H), 3.68 (bs, 2H).

Synthesis of Intermediate 14

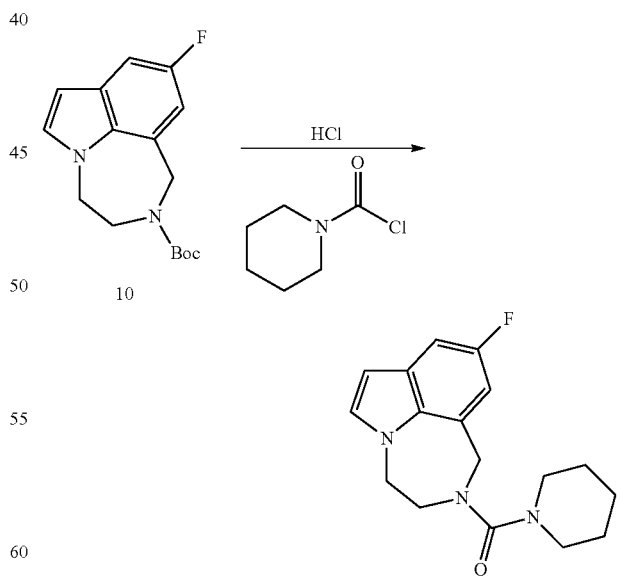

To a solution of intermediate 10 (15 g, 51.7 mmol) in DCM (450 ml) was added HCl/dioxane (7 M, 150 ml) at room temperature. The mixture was stirred at room temperature for 2 hrs. TLC (PE/EtOAc=1/1) showed the reaction was complete. The solvent was concentrated in vacuum to give white solid.

To a solution of the white solid in DMF (120 ml) was added Et$_3$N (15.7 g, 155.1 mmol), then 1-Piperidinecarbonyl chloride (9.2 g, 62 mmol) was added below 5° C. The mixture was stirred at room temperature for 2 hrs. TLC (DCM/MeOH=10/1) showed the reaction was complete. Then the mixture was poured into ice-water and extracted with EtOAc (200 ml×4). The combined organic phases were washed with water, brine, dried over Na$_2$SO$_4$ and concentrated in vacuum. The residue was purified by flash column chromatography to give intermediate 16 (8.0 g, 51.3%) as white solid.

$^1$H NMR (CDCl$_3$, 400 MHz): δ (ppm) 7.16 (dd, 1H, J=2.4 Hz, 9.2 Hz), 7.09 (d, 1H, J=3.2 Hz), 6.75 (dd, 1H, J=2.0 Hz, 9.6 Hz), 6.49 (d, 1H, J=3.2 Hz), 4.64 (s, 2H), 4.18~4.21 (m, 2H), 3.99~4.02 (m, 2H), 3.17~3.19 (m, 4H), 1.58-1.60 (m, 6H).

Synthesis of Intermediate 17

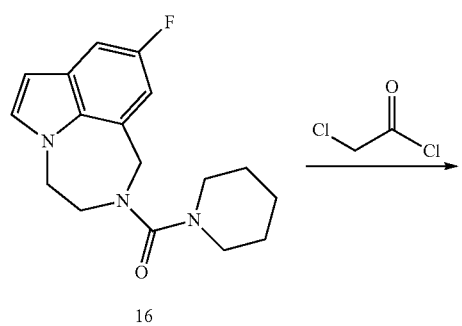

To a mixture of AlCl$_3$ (12.6 g, 94.2 mmol) in DCM (160 ml) was added a solution of intermediate 16 (4.0 g, 13.3 mmol) in DCM (30 ml) at 0° C. under N$_2$. Then a solution of 2-chloroacetyl chloride (4.5 g, 39.8 mmol) in DCM (30 ml) was added dropwise, the mixture was stirred at room temperature for 2 hrs. TLC (PE/EtOAc=1/1) showed the reaction was complete. Poured into ice water, extracted with DCM (100 ml×3). The combined organic phases were washed with brine, dried over Na$_2$SO$_4$ and concentrated in vacuum. The residue was purified by flash column chromatography (eluted with PE/EtOAc from 5:1 to 1:2) to give intermediate 17 (2.5 g, 50%) as yellow solid.

$^1$H NMR (CDCl$_3$, 400 MHz): δ (ppm) 7.98~8.00 (m, 1H), 7.85 (s, 1H), 6.86 (dd, 1H, J=2.0 Hz, 9.2 Hz), 4.68 (s, 2H), 4.45 (s, 2H), 4.37~4.38 (m, 2H), 4.01~4.04 (m, 2H) 3.17~3.22 (m, 4H), 1.57~1.63 (m, 6H).

Synthesis of Intermediate 16.

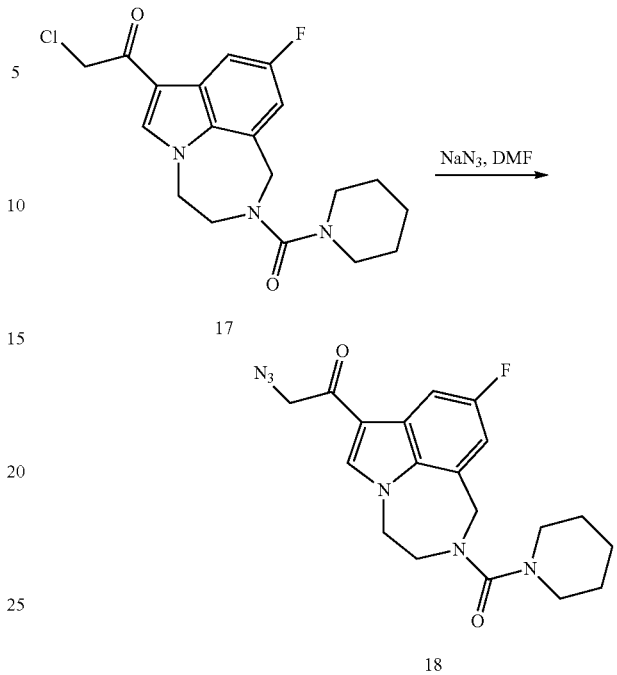

To a solution of intermediate 17 (1.3 g, 3.3 mmol) in DMF (13 ml) was added NaN$_3$ (0.2 g, 3.5 mmol). The mixture was stirred at room temperature for 2 hrs. TLC (PE/EtOAc=1/1) showed the reaction was complete. Then the mixture was poured into ice-water and extracted with EtOAc, the combined organic phases were washed with water, brine, dried over Na$_2$SO$_4$ and concentrated in vacuum. The residue was dissolved in MeOH, concentrated in vacuum to give a solution of intermediate 18 (2.3 g, crude) as brown oil.

Synthesis of Intermediate 19.

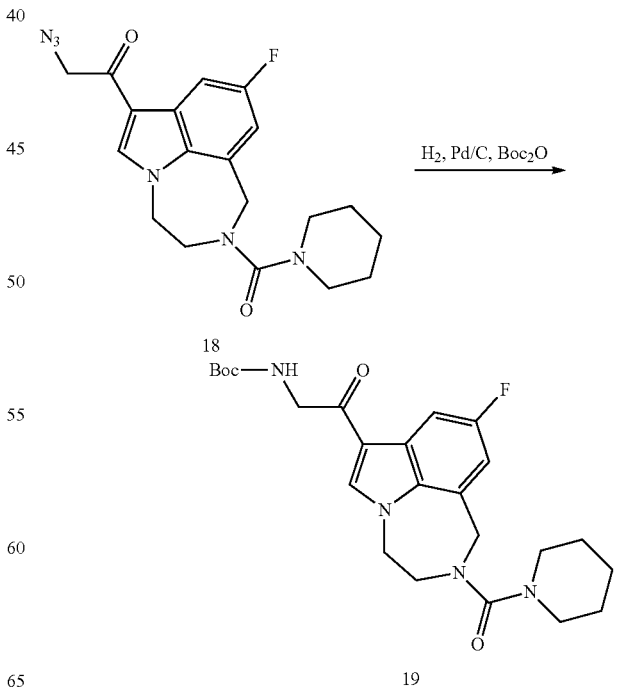

To a solution of intermediate 18 (4.5 g, 6.0 mmol) in MeOH/THF=(90 ml/90 ml) was added Boc₂O (1.9 g, 9.0 mmol) and Pd/C (0.4 g). The mixture was degassed and flushed with H₂ for three times, and then bubbled H₂ to keep the pressure is 50 psi, stirred at room temperature for 2 hrs. TLC (PE/EtOAc=2/1) showed the reaction was complete. Then the mixture filtered and concentrated in vacuum to give of intermediate 19 (2 g, 71.4% for two steps) as a white solid.

$^1$H NMR (DMSO-d$_6$, 400 MHz): δ (ppm) 8.45 (s, 1H), 7.71 (dd, 1H, J=2.4 Hz, 9.2 Hz), 7.07~7.07 (m, 2H), 4.70 (s, 2H), 4.47~4.49 (m, 2H), 4.24 (d, 2H, J=5.6 Hz), 3.88~3.90 (m, 2H), 3.03 (s, 4H), 1.47-1.56 (m, 6H), 1.41 (s, 9H).

Synthesis of Intermediate 20

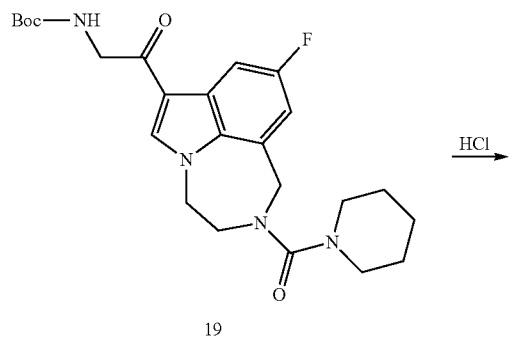

19

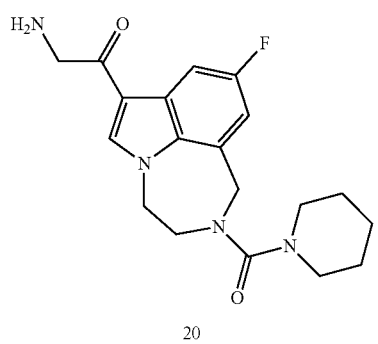

20

To a solution of intermediate 19 (2.0 g, 4.4 mmol) in DCM (60 ml) was added HCl/dioxane (7 M, 20 ml) at room temperature. The mixture was stirred at room temperature for 2 hrs. TLC (PE/EtOAc=1/1) showed the reaction was complete. The mixture solution was filtered, the filtered cake was dried in vacuum to give intermediate 20 (1.3 g, 72.6%) as white solid.

$^1$H NMR (DMSO-d$_6$, 400 MHz): δ (ppm) 8.57 (s, 1H), 8.36 (s, 3H), 7.71 (dd, 1H, J=2.4 Hz, 9.2 Hz), 7.10 (dd, 1H, J=2.0 Hz, 9.6 Hz), 4.72 (s, 2H), 4.53 (s, 2H), 4.31-4.32 (m, 2H), 3.90 (s, 2H), 3.03 (s, 4H), 1.49 (s, 6H).

Synthesis of Intermediate 21.

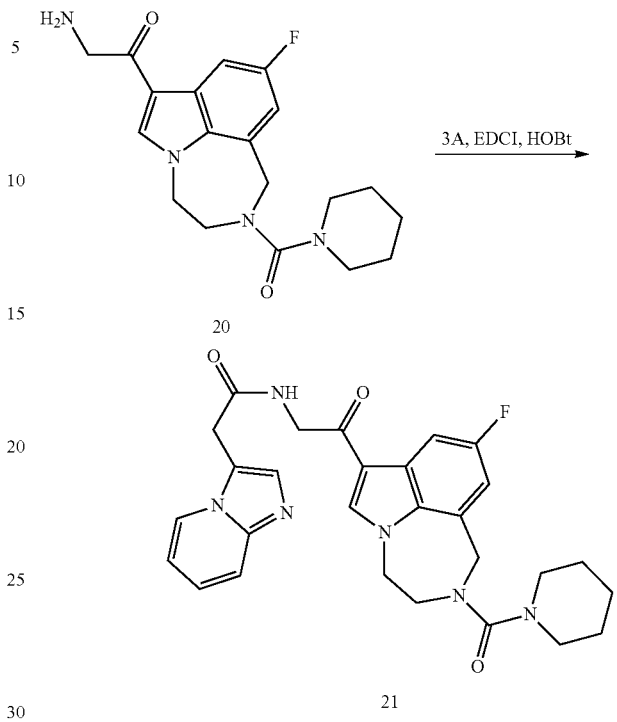

To a solution of intermediate 20 (1.3 g, 3.2 mmol) in DMF (15 ml) was added intermediate 3 (0.7 g, 4.2 mmol), EDCI (2.45 g, 12.8 mmol), DIPEA (1.2 g, 9.6 mmol), and HOBt (0.4 g, 3.2 mmol). The mixture was stirred at room temperature for 6 hrs. TLC (DCM/MeOH=10/1) showed the reaction was complete. Then the mixture was poured into ice-water and extracted with EtOAc, the combined organic phases were washed with water, brine, dried over Na₂SO₄ and concentrated in vacuum. The residue was purified by flash column chromatography to give intermediate 21 (0.8 g, 49.1%) as brown solid.

$^1$H NMR (CDCl$_3$, 400 MHz): δ (ppm) 8.17 (d, 1H, J=6.4 Hz), 7.78~7.82 (m, 2H), 7.57 (s, 2H), 7.29~7.31 (m, 1H), 7.14~7.17 (m, 1H), 6.80~6.82 (m, 2H), 4.62 (s, 2H), 4.48 (s, 2H), 4.28 (s, 2H), 3.96 (s, 4H), 3.14 (s, 4H), 1.42~1.44 (m, 6H).

Synthesis of Intermediate 22.

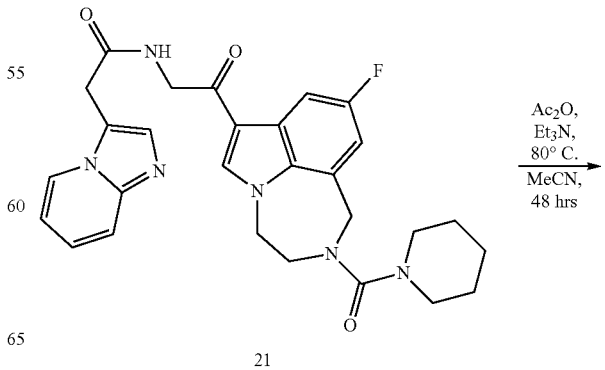

21

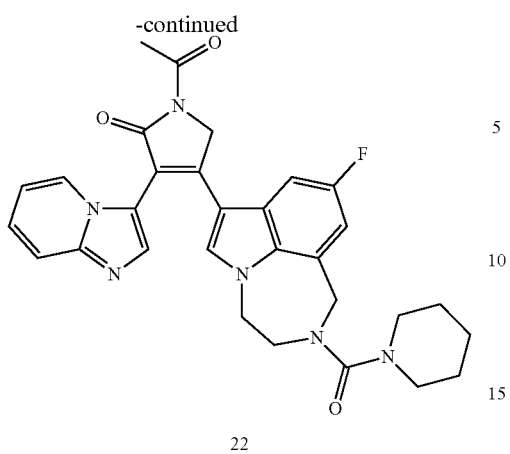

22

To a solution of intermediate 20 (0.2 g, 0.4 mmol), in MeCN (6 ml) was added Ac₂O (0.5 g, 4.9 mmol) and Et₃N (0.3 g, 3.3 mmol) under N₂ at 0° C., then the mixture was stirred at 80° C. for 48 hrs. Then the mixture concentrated in vacuum to remove the solvent, the residue was dissolved into DCM, washed with water, brine, dried over Na₂SO₄ and concentrated in vacuum. The residue was purified by prep-HPLC to give intermediate 21 (40 mg, purity ~88%, 17.6%) as yellow solid.

Synthesis of Compound I-4.

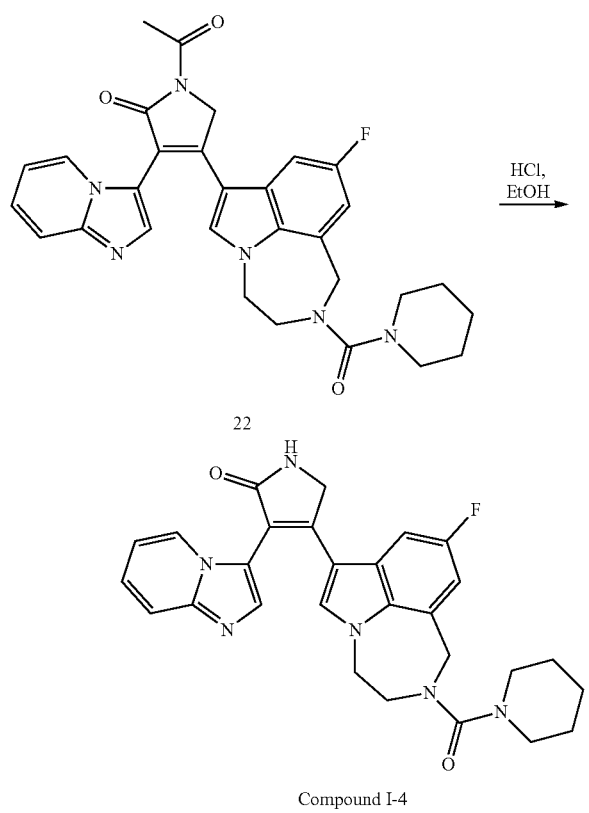

To a solution of intermediate 22 (40 mg, 0.06 mmol) in EtOH (2 ml) was added HCl (6 N, 2 ml) at room temperature under N₂. The mixture was heated to reflux for 1 hr, cooled to 0° C., ice-water was added to the solution, then adjusted pH=7~8 with Na₂CO₃ (aq), extracted with DCM, the combined organic phase was washed with brine, dried with Na₂SO₄, filtered and concentrated in vacuum to give a crude, which was purified by prep-HPLC to give Compound I-4 (11 mg, 36.6%) as yellow solid.

¹H NMR (CD₃OD, 400 MHz): δ (ppm) 8.10 (s, 2H), 7.91 (d, 1H, J=8.8 Hz), 7.8-17.85 (m, 1H), 7.47 (s, 1H), 7.15 (t, 1H, J=6.4 Hz), 6.73 (d, 1H J=8.4 Hz), 6.43 (dd, 1H, J=1.6 Hz, 9.6 Hz), 4.73 (s, 2H), 4.58 (s, 2H), 4.27~4.29 (m, 2H), 3.77~3.80 (m, 2H), 3.00 (s, 4H), 1.4~41.49 (m, 6H).

MS Calcd: 498.22; MS Found: 499.3 [M+1]⁺.

Synthetic of Intermediate 23

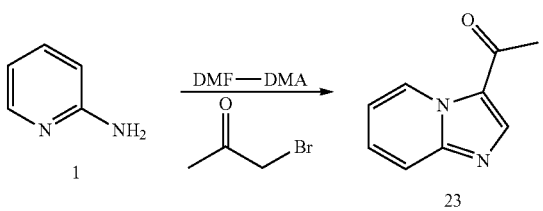

A solution of intermediate 1 (20 g, 0.21 mol) and DMF-DMA (38 g, 0.32 mol) was stirred at 90° C. for 3 hrs. The mixture was concentrated in vacuum, the residue was dissolved in EtOH (200 ml), 1-bromopropan-2-one (32 g, 0.23 mol) was added dropwise, and the mixture was stirred at room temperature for 4 hrs. The solvent was concentrated in vacuum and purified by flash column chromatography to give intermediate 23 (4.1 g, 12%) as a yellow solid.

¹H NMR (CDCl₃, 400 MHz): δ (ppm) 9.6~49.66 (m, 1H), 8.35 (s, 1H), 7.76 (d, 1H, J=8.8 Hz), 7.48~7.52 (m, 1H), 7.07~7.11 (m, 1H), 2.62 (s, 3H)

Synthetic of intermediate 24.

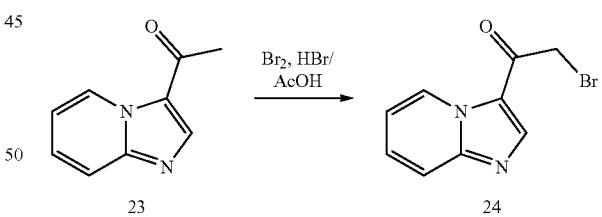

To a solution of intermediate 23 (4.1 g, 25.6 mmol) in HBr/AcOH (40 ml) was added Br₂ (5.3 g, 33.3 mmol) at 0° C. under N₂. The mixture was stirred at 0° C. for 2 hrs. Then the mixture was stirred at room temperature for another 2 hrs. MTBE was added, filtered the filtered cake was dissolved in EtOAc, washed with water, brine, dried over Na₂SO₄ and concentrated in vacuum to give intermediate 24 (2.1 g, 34.4%) as white solid.

¹H NMR (DMSO-d₆, 400 MHz): δ (ppm) 9.50 (d, 1H, J=6.8 Hz), 8.79 (s, 1H), 7.89 (d, 1H, J=8.8 Hz), 7.69~7.73 (m, 1H), 7.35 (t, 1H, J=6.8 Hz,), 4.78 (s, 2H).

Synthetic of Intermediate 25

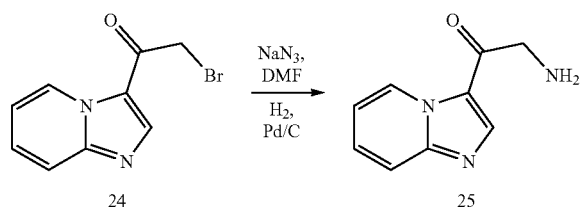 [SMILES: O=C(CBr)c1cnc2ccccn12 ; NCC(=O)c1cnc2ccccn12]

To a solution of intermediate 24 (2.1 g, 8.8 mmol) in DMF (20 ml) was added NaN₃ (0.6 g, 9.7 mmol). The mixture was stirred at room temperature for 1 hrs. Then the mixture was poured into ice-water and extracted with EtOAc, the combined organic phases were washed with water, brine, dried over $Na_2SO_4$ and concentrated in vacuum. The residue was dissolved in MeOH (40 ml), and Pd/C (0.4 g) was added, the mixture was degassed and flushed with $H_2$ for three times, and then bubbled 1-12 to keep the pressure is 50 psi, stirred at room temperature for 1 hrs. TLC (PE/EtOAc=2/1) showed the reaction was complete. Then the mixture filtered and concentrated in vacuum to give of intermediate 25 (1.2 g, 77.9%) as a red solid.

¹H NMR (DMSO-d₆, 400 MHz): δ (ppm) 9.55 (d, 1H, J=6.8 Hz), 8.64 (s, 1H), 7.84 (d, 1H, J=9.2 Hz), 7.6-17.65 (m, 1H), 7.29 (t, 1H, J=6.8 Hz,), 3.97 (s, 2H), 1.75-1.84 (br, 2H).

Synthetic of Intermediate 26

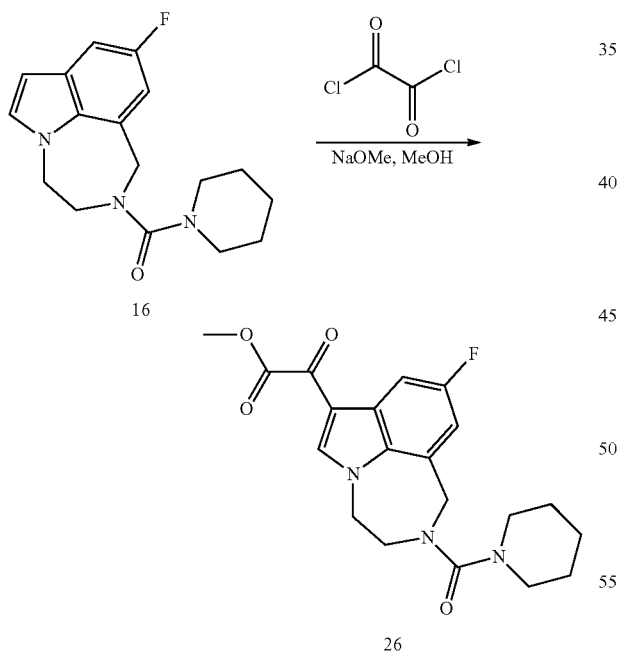

To a solution of intermediate 16 (3.0 g, 10.0 mmol) in DCM (90 ml) was added oxalyl dichloride (1.5 g, 12.0 mmol) at 0° C. under $N_2$. The mixture was stirred at 0° C. for 2 hrs. The mixture was cooled to −78° C. and NaOMe (1.2 g, 22.0 mmol) in MeOH (15 ml) was added dropwise, the mixture was stirred at room temperature for 1 hrs. TLC (PE/EtOAc=1/1) showed the reaction was complete. Then the mixture was poured into ice-water and extracted with DCM (50 ml×2). The combined organic phases were washed with water, brine, dried over $Na_2SO_4$ and concentrated in vacuum. The residue was purified by flash column chromatography to give intermediate 26 (3.0 g, 76.9%) as white solid.

¹H NMR (CDCl₃, 400 MHz): δ (ppm) 8.39 (d, 1H, J=1.2 Hz), 8.06 (d, 1H, J=8.8 Hz), 6.89 (d, 1H, J=8.8 Hz), 4.69 (s, 2H), 4.39~4.41 (m, 2H), 4.01~4.03 (m, 2H), 3.95 (s, 3H), 3.16~3.18 (m, 4H), 1.59~1.63 (m, 6H).

Synthetic of Intermediate 27

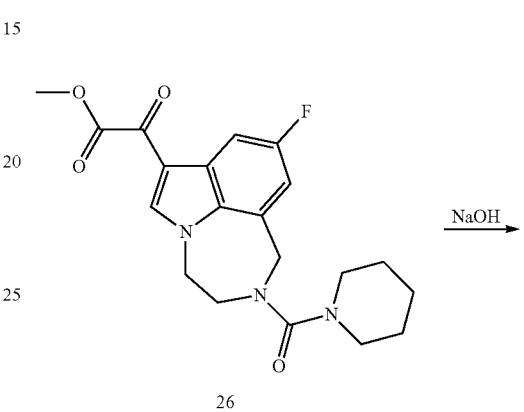

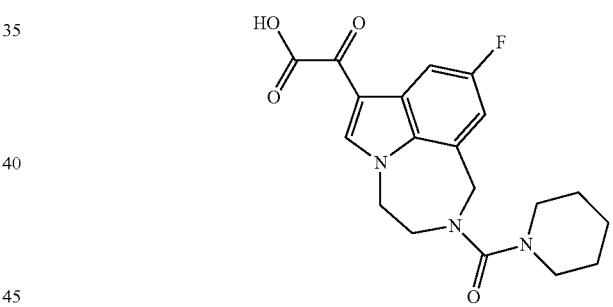

To a mixture of intermediate 26 (3.0 g, 7.7 mmol) in MeOH/THF (15 ml/15 ml) was added a solution of NaOH (0.9 g, 23.1 mmol) in $H_2O$ (10 ml). The mixture was stirred at 30° C. for 2 hrs. TLC (PetroleumEther/EtOAc=1/1) showed the reaction was complete. The mixture was concentrated in vacuum. The residue was dissolved in water (30 ml) and adjusted pH=3~4 with 2 N HCl, filtered. The filter cake was dried in vacuum to give intermediate 27 (2.7 g, 93%) as white solid.

¹H NMR (DMSO-d₆, 400 MHz): δ (ppm) 8.48 (s, 1H), 7.74 (dd, 1H, J=2.0 Hz, 9.6 Hz), 7.11~7.13 (m, 1H), 4.72 (s, 2H), 4.57~4.60 (m, 2H), 3.88 (t, 2H, J=5.2 Hz,), 3.00~3.10 (m, 4H), 1.42~1.58 (m, 6H).

Synthetic of Intermediate 28

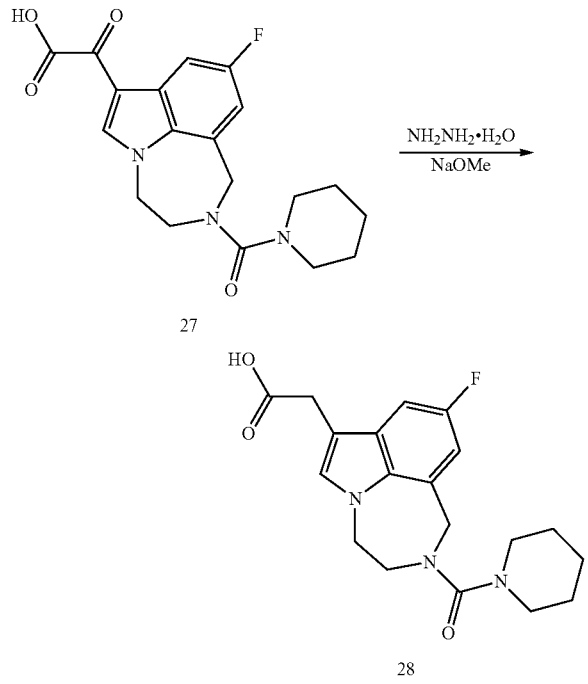

To a solution of intermediate 27 (0.9 g, 2.4 mmol) in 2-ispropoxyethanol (9 ml) was added hydrazine hydrate (0.6 g, 12.0 mmol). The mixture was stirred at 63° C. for 45 min. NaOMe (1.4 g, 25.7 mmol) was added slowly, then the mixture was heated to 153° C. for 2 hrs. TLC (DCM/MeOH=5/1) showed the reaction was complete. Then the mixture was cooled, poured into ice-water and adjusted pH=3~4 with conc. HCl, extracted with DCM, the combined organic phases were washed with brine, dried over $Na_2SO_4$ and concentrated in vacuum. The residue was dissolved in MTBE/PE=1/1 (20 ml), filtered, the filtered cake was dried in vacuum to give intermediate 28 (0.3 g, 34.5%) as white solid.

$^1$H NMR (DMSO-$d_6$, 400 MHz): δ (ppm) 12.26 (br, 1H), 7.28 (s, 1H), 7.14 (dd, 1H, J=2.4 Hz, 9.6 Hz), 6.90 (dd, 1H, J=2.0 Hz, 10.0 Hz), 4.64 (s, 2H), 4.21~4.23 (m, 2H), 3.83~3.86 (m, 2H), 3.61 (s, 2H), 3.01~3.12 (m, 4H), 1.40~1.58 (m, 6H).

Synthetic of intermediate 29.

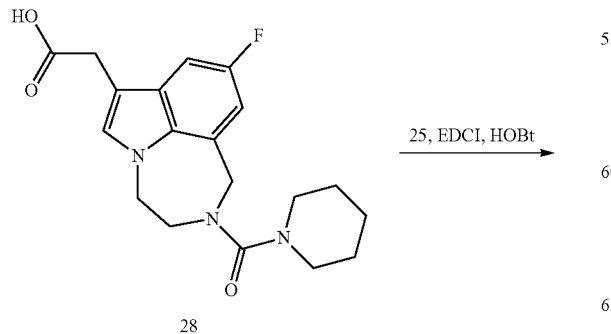

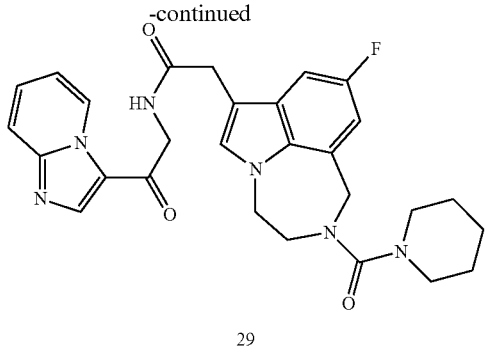

To a solution of intermediate 28 (1.0 g, 2.8 mmol) in DMF (50 ml) was added intermediate 25 (0.6 g, 3.6 mmol), EDCI (2.1 g, 11.2 mmol), DIPEA (1.1 g, 8.4 mmol), and HOBt (0.4 g, 2.9 mmol). The mixture was stirred at room temperature for 4 hrs. TLC (DCM/MeOH=10/1) showed the reaction was complete. Then the mixture was poured into ice-water and extracted with EtOAc, the combined organic phases were washed with water, brine, dried over $Na_2SO_4$ and concentrated in vacuum. The residue was purified by flash column chromatography to give intermediate 29 (0.7 g, 48.6%) as yellow solid.

$^1$H NMR (CDCl$_3$, 400 MHz): δ (ppm) 9.49 (d, 1H, J=6.8 Hz), 8.42 (s, 1H), 7.76 (d, 1H, J=8.8 Hz), 7.5~07.54 (m, 1H), 7.19~7.20 (m, 1H), 7.15~7.17 (m, 1H), 7.08~7.11 (m, 1H), 6.7~56.80 (m, 2H), 4.66 (d, 2H, J=4.8 Hz), 4.64 (s, 2H), 4.16~4.22 (m, 2H), 3.98~4.01 (m, 2H), 3.76 (s, 2H), 3.15~3.20 (m, 4H), 1.51~1.62 (m, 6H).

Synthetic of Intermediate 30

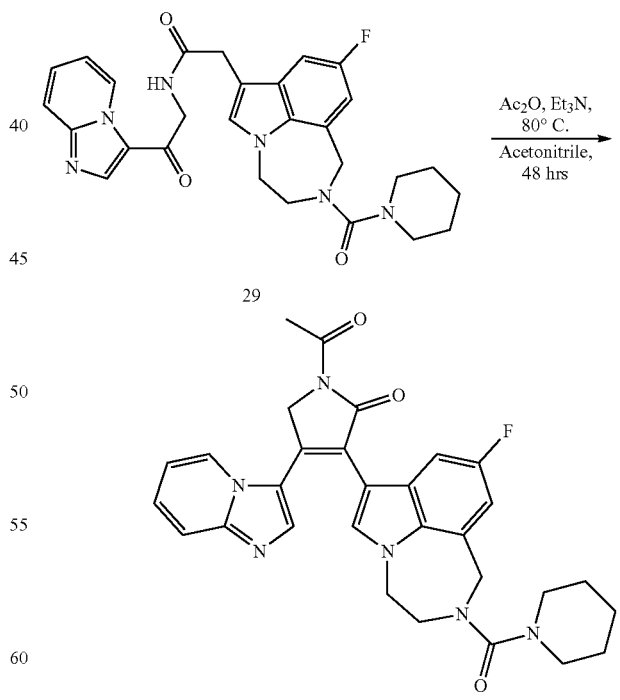

To a solution of intermediate 29 (0.2 g, 0.4 mmol) in MeCN (6 ml) was added Ac$_2$O (0.5 g, 4.9 mmol) and Et$_3$N (0.3 g, 3.3 mmol) under N$_2$ at 0° C., then the mixture was stirred at 80° C. for 48 hrs. Then the mixture concentrated in vacuum to remove the solvent, the residue was dissolved into DCM, washed with water, brine, dried over $Na_2SO_4$ and concentrated in vacuum to give intermediate 30 (250 mg, crude) as brown solid.

Synthetic of Compound I-49

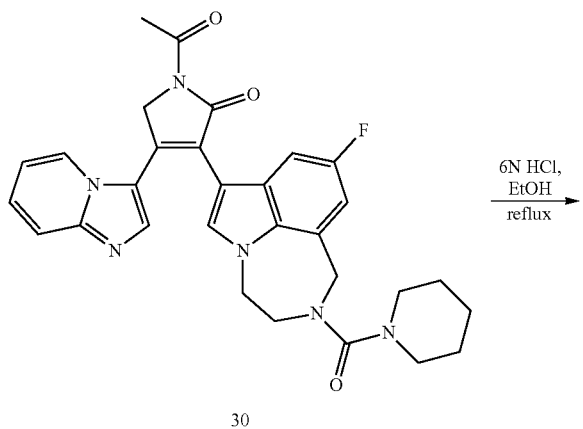

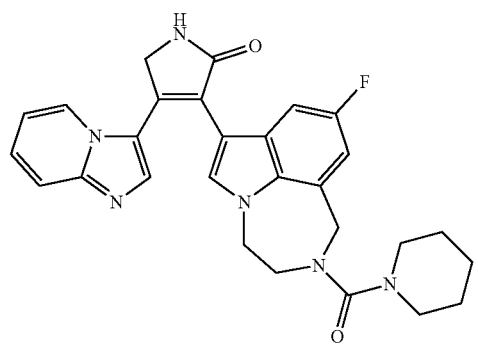

Compound I-49

To a solution of intermediate 30 (500 mg, crude) in EtOH (5 ml) was added HCl (6 N, 5 ml) at room temperature under $N_2$. The mixture was heated to reflux for 1 hr, cooled to 0° C., ice-water was added to the solution, then adjusted pH=78 with $Na_2CO_3$ (aq), extracted with DCM, the combined organic phase was washed with brine, dried with $Na_2SO_4$, filtered and concentrated in vacuum to give a crude, which was purified by prep-HPLC to give Compound I-49 (46 mg, 12.2% for two steps) as yellow solid.

$^1$H NMR (CD$_3$OD, 400 MHz): δ (ppm) 8.53 (s, 1H), 7.92 (d, 1H, J=9.2 Hz), 7.6~27.81 (m, 3H), 6.95 (t, 1H, J=6.4 Hz), 6.66 (dd, 1H, J=2 Hz, 9.2 Hz), 6.10 (dd, 1H, J=2.4 Hz, 9.6 Hz), 4.67 (s, 2H), 4.64 (s, 2H), 4.41~4.44 (m, 2H), 3.93~3.95 (m, 2H), 3.12-3.14 (m, 4H), 1.4~51.68 (m, 6H).

MS Calcd: 498.22; MS Found: 499.3 [M+1]$^+$.

Biological Examples

Assay:

Enzymatic activities using recombinant human GSK3 using an in vitro enzymatic assay for inhibition GSK3α and GSK3β.

Enzymes and Substrates:

| Assay | Enzyme Used (ng)/Reaction | Substrate/ATP |
|---|---|---|
| GSK3α | 13 | 0.1 mg/ml GSKtide/10 uM ATP |
| GSK3β | 13 | 0.1 mg/ml GSKtide/10 uM ATP |

Assay Conditions:

The assay was performed using Kinase-Glo Max luminescence kinase assay kit (Promega). It measures kinase activity by quantitating the amount of ATP remaining in solution following a kinase reaction. The luminescent signal from the assay is correlated with the amount of ATP present and is inversely correlated with the amount of kinase activity. The compounds were diluted in 10% DMSO and 5 µl of the dilution was added to a 50 µl reaction so that the final concentration of DMSO is 1% in all of reactions. The enzymatic reactions were conducted at 30° C. for 40 minutes. The 50 µl reaction mixture contains 40 mM Tris, pH 7.4, 10 mM MgCl$_2$, 0.1 mg/ml BSA, 2 mM DTT, 0.1 mg/ml GSKtide substrate, 10 uM ATP and GSK3. After the enzymatic reaction, 50 µl of Kinase-Glo Max Luminescence kinase assay solution (Promega) was added to each reaction and incubate the plate for 15 minutes at room temperature. Luminescence signal was measured using a BioTek Synergy 2 microplate reader.

Data Analysis:

Kinase activity assays were performed in duplicate at each concentration. The luminescence data were analyzed using the computer software, Graphpad Prism. The difference between luminescence intensities in the absence of Kinase (Lut) and in the presence of Kinase (Luc) was defined as 100% activity (Lut−Luc). Using luminescence signal (Lu) in the presence of the compound, % activity was calculated as: % activity={(Lut−Lu)/(Lut−Luc)}×100%, where Lu=the luminescence intensity in the presence of the compound (all percent activities below zero were shown zero in the table).

The values of % activity versus a series of compound concentrations were then plotted using non-linear regression analysis of Sigmoidal dose-response curve generated with the equation Y=B+(T−B)/1+10((Log EC50−X)×Hill Slope), where Y=percent activity, B=minimum percent activity, T=maximum percent activity, X=logarithm of compound and Hill Slope=slope factor or Hill coefficient. The IC50 value was determined by the concentration causing a half-maximal percent activity.

Certain compounds were synthesized and tested. Activity of certain compounds is shown in the table below Activity for certain compounds vs GSK-alpha and GSK-beta

| Compound | Potency GSK-3alpha | Potency GSK-3beta |
|---|---|---|
| Compound I-4 | 15.6 nM | 22 nM |
| Compound I-49 | 8.2 nM | 8.3 nM |

Assay: Wnt Signaling Pathway Activation in HEK293 Cells.

Materials:

TCF/LEF reporter-HEK293 Recombinant cell lines

One-Step Luciferase Assay System

Assay Conditions:

The assay was performed using TCF/LEF reporter-HEK293 Recombinant cell lines

Plate 32,000 TCF/LEF reporter-HEK293 Recombinant cells/well in a 96-well plate (volume=90 µL). The compounds were diluted in the thawing medium 1 containing 1% DMSO, and add 10 µL to each well (0.1% DMSO at final). The cells were incubated for overnight at 37° C. in 5% $CO_2$ followed by adding 100 µL of One-Step Luciferase Assay System to each well. Plate was incubated for 30 min at room temperature in a darkroom.

Luminescence signal was measured using a BioTek Synergy 2 microplate reader.

Data Analysis

Wnt signaling pathway activation assays were performed in triplicates at each concentration. The luminescence data were analyzed using the computer software, Graphpad Prism. The luminescence intensity in the absence of Compounds (Luc) was defined the minimum activity and the signal in the presence of the highest concentration of the Compound was defined as the maximum activity. Signal from the wells containing medium only was defined as background.

The values of the luminescence signal versus a series of compound concentrations were then plotted using non-linear regression analysis of Sigmoidal dose-response curve generated with the equation $Y=B+(T-B)/1+10^{((Log\ EC50-X)\times Hill\ Slope)}$, where Y=percent activity, B=minimum activity, T=maximum activity, X=logarithm of compound and Hill Slope=slope factor or Hill coefficient. The EC50 value was determined by the concentration causing a half-maximal activity.

Figure 2:
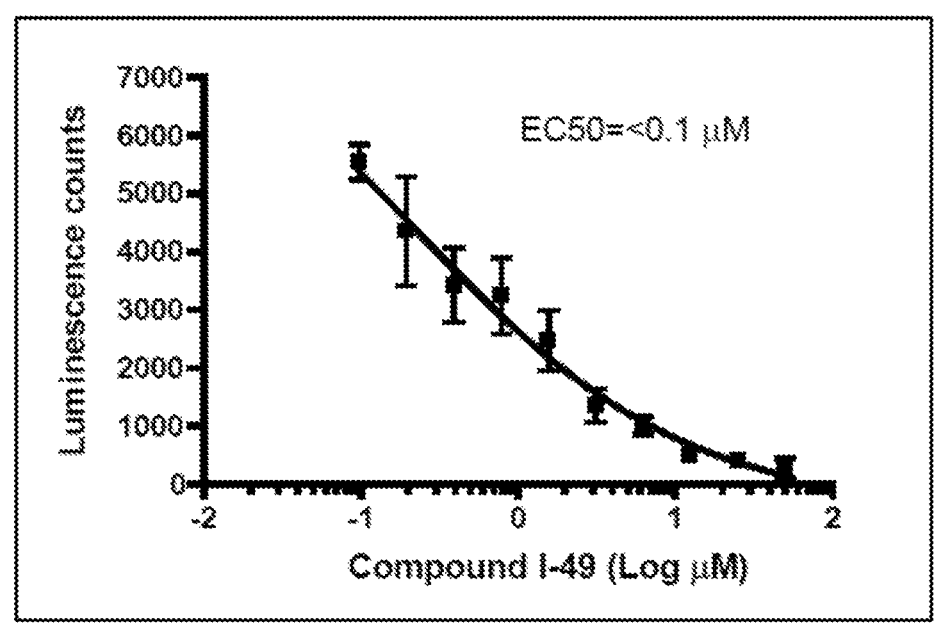
FIG. 2 is a diagram showing the activity of Compound I-49 in the assay performed using TCF/LEF reporter-HEK293 Recombinant cell lines.

Certain compounds were synthesized and tested. Activity of certain compounds is shown in the table below and in FIGS. 1 and 2.

| Compound | Potency |
|---|---|
| Compound I-4 | 60 nM |
| Compound I-49 | <10 nM |

Assay: Mouse Strains

Lgr5-EGFP-IRES-Cre-ER mice (Barker et al., 2007) (http://jaxmice.jax.org/strain/008875.html) are used to analyze the effects of small molecules on cochlear stem cell expansion.

Isolation of stem cells from the inner ear: All animal studies are conducted under an approved institutional protocol according to National Institutes of Health guidelines. For experiments with neonatal mice (postnatal days 1-3), the cochleae are dissected in HBSS and the organ of Corti are separated from the stria vascularis and the modiolus. The organs of Corti are then treated with Cell Recovery Solution (Corning) for 1 h to separate cochlear epithelium from the underlying mesenchyme. Epithelia are then collected and treated with TrypLE (Life Technologies) for 15-20 minutes at 37° C. Single cells obtained by mechanical trituration are filtered (40 µm) and suspended in Matrigel (Corning) for 3D culture.

Expansion of Lgr5-Positive Cells

Cells are cultured in a 1:1 mixture of DMEM and F12, supplemented with Glutamax (GIBCO), N2, B27 (Invitrogen), EGF (50 ng/ml; Chemicon), bFGF (50 ng/ml; Chemicon), IGF1 (50 ng/ml; Chemicon) and the composition provided herein. Media are changed every other day.

Differentiation of Lgr5-Positive Progenitor Cells Stem cell colonies are differentiated in a 1:1 mixture of DMEM and F12, supplemented with Glutamax (GIBCO), N2, B27 (Invitrogen), with addition of specific drugs or after removal of growth factors without drug addition. Small molecules are added to the culture to test their effect on differentiation.

Analysis

Lgr5-positive cells are quantified after 10 days (D10) in culture in multiple conditions. Cell colonies are dissociated into single cells using TrypLE (Gibco). The cells are then stained with propidium iodide (PI) and are analyzed using a flow cytometer for Lgr5-GFP expression. The number of GFP-positive cells and the percentage of GFP-positive cells are quantified.

Atoh1-nGFP-positive cells are quantified at day 0 (D0) and day 10 (D10) of differentiation treatment to determine the number of hair cells that have differentiated. Cell colonies are incubated in Cell Recovery Solution to release the colonies from Matrigel and dissociated into single cells using TrypLE. The total number and percentage of GFP-positive cells are quantified using a flow cytometer for multiple culture conditions. ANOVA is used to compare means across conditions, and the two-tailed Student's T-test is used to compare each condition to the treatment with the highest yield.

Certain compounds were synthesized and tested. Activity of certain compounds is shown in the table below.

| Compound | Potency | % of Cells |
|---|---|---|
| Compound I-4 | 333.3 nM | 8.3 |
| Compound I-49 | 333.3 nM | 5.5 |

What is claimed is:

1. A compound of Formula (I) or (I'):

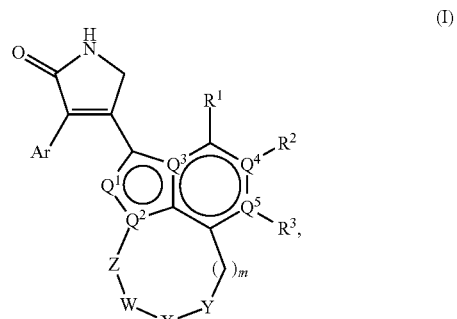

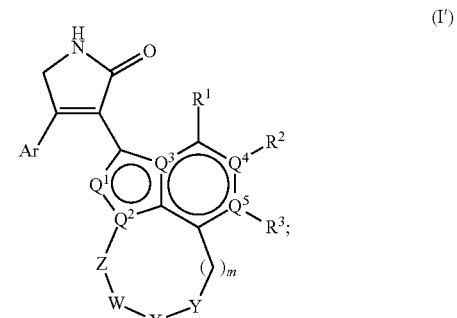

or a pharmaceutically acceptable salt or tautomer thereof, wherein:

$Q^1$ is CH or N;
$Q^2$ is C or N;
$Q^3$ is C or N;
$Q^4$ is C or N;
$Q^5$ is C or N;

wherein one to two of $Q^1$, $Q^2$, $Q^3$, $Q^4$, and $Q^5$ is N;

$R^1$ is selected from the group consisting of hydrogen, halo, $C_1$-$C_4$alkyl, $C_1$-$C_4$alkenyl, $C_1$-$C_4$alkynyl, —CN, —OH, —O—$C_1$-$C_4$alkyl, —NH$_2$, —NHC(O)$R^{1a}$, and —S(O)$_2$NH$_2$; wherein the alkyl is optionally substituted with one to 3 substituents independently selected from the group consisting of halo and —OH; and wherein $R^{1a}$ is $C_1$-$C_4$alkyl;

$R^2$ is selected from the group consisting of hydrogen, halo, $C_1$-$C_4$alkyl, $C_1$-$C_4$alkenyl, $C_1$-$C_4$alkynyl, —CF$_3$, —CN, —OH, —O—$C_1$-$C_4$alkyl, —NH$_2$, —NH($C_1$-$C_4$alkyl), —N($C_1$-$C_4$alkyl)$_2$, —NHC(O)$R^{2a}$, and —S(O)$_2$NH$_2$; wherein the alkyl is optionally substituted with one to 3 substituents independently selected from the group consisting of halo and OH; and wherein $R^{2a}$ is $C_1$-$C_4$alkyl; or $R^2$ is absent, if $Q^4$ is N;

$R^3$ is selected from the group consisting of hydrogen, halo, $C_1$-$C_4$alkyl, $C_1$-$C_4$alkenyl, $C_1$-$C_4$alkynyl, —CN, —OH, —O—$C_1$-$C_4$alkyl, —NH$_2$, —NHC(O)$R^{3a}$, and —S(O)$_2$NH$_2$; wherein the alkyl is optionally substituted with one to 3 substituents independently selected from the group consisting of halo and —OH; and wherein $R^{1a}$ is $C_1$-$C_4$alkyl; or $R^3$ is absent, if $Q^5$ is N;

Ar is selected from the group consisting of aryl, heteroaryl,

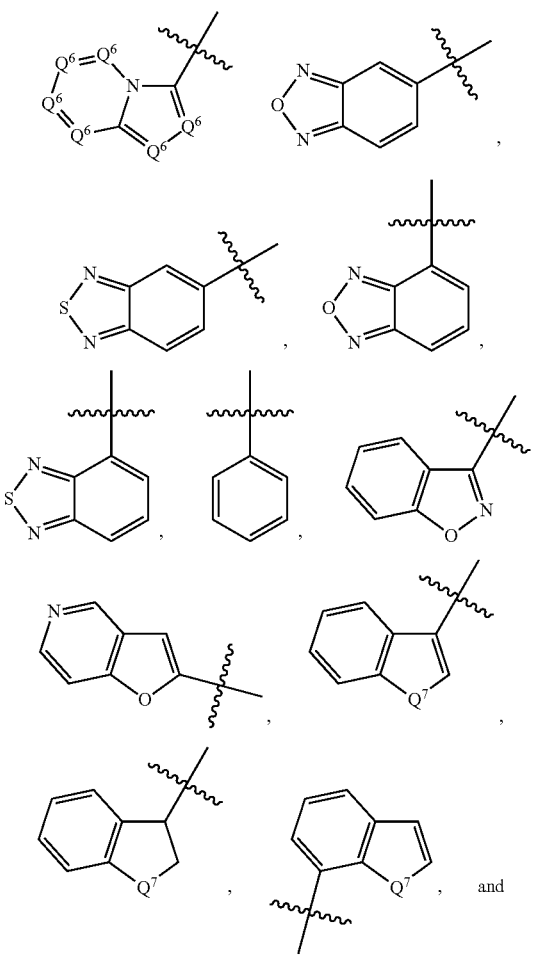

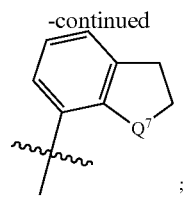
;

wherein Ar is optionally substituted with deuterium, halo, alkyl, alkoxy, aminoalkoxy, CF$_3$, and CN;

each $Q^6$ is independently selected from $CR^{Q6}$ and N; wherein $CR^{Q6}$ is hydrogen, halo, —CN, lower alkyl, or substituted alkyl;

each $Q^7$ is independently selected from S, O, CH$_2$, $NR^{Q7}$; where $R^{Q7}$ is hydrogen or optionally substituted $C_1$-$C_4$alkyl;

—Z—W—X—Y— is —C($R^Z$)$_2$—C($R^W$)$_2$—N($R^X$)—C($R^Y$)$_2$—, —C($R^Z$)$_2$—C($R^W$)$_2$—CH($R^X$)—C($R^Y$)$_2$—, or —C($R^W$)$_2$—CH($R^X$)—C($R^Y$)$_2$—;

each $R^Z$ is independently selected from the group consisting of hydrogen, deuterium, halo, and $C_1$-$C_4$alkyl, or both $R^Z$ groups together form $C_3$-$C_6$cycloalkyl or oxo;

each $R^W$ is independently selected from the group consisting of hydrogen, deuterium, halo, and $C_1$-$C_4$alkyl, or both $R^W$ groups together form $C_3$-$C_6$cycloalkyl or oxo;

or $R^Z$ and $R^W$ together with the carbons to which they are attached form a $C_3$-$C_6$cycloalkyl;

$R^X$ is selected from the group consisting of $R^{X1}$, —COR$^{X1}$, —SO$_2$R$^{X1}$, —CON(R$^{X2}$)$_2$, and —(C$_1$-C$_4$alkylene)-R$^{X1}$, and wherein the —(C$_1$-C$_4$alkylene)-R$^{X1}$ is optionally substituted with one to four halo on the C$_1$-C$_4$alkylene;

wherein $R^{X1}$ is $C_3$-$C_8$cycloalkyl, heteroaryl, or heterocyclic, wherein the heterocyclic is optionally substituted with one to twelve substituents independently selected from the group consisting of deuterium, halo, —CF$_3$, —[C(R$^{X1a}$)$_2$]$_p$—CN, C$_1$-C$_4$alkyl, —[C(R$^{X1a}$)$_2$]$_p$—OH, —[C(R$^{X1a}$)$_2$]$_p$—O—C$_1$-C$_4$alkyl, —[C(R$^{X1a}$)$_2$]$_p$—NHCOC$_1$-C$_4$alkyl, —[C(R$^{X1a}$)$_2$]$_p$—N(C$_1$-C$_4$alkyl)-COC$_1$-C$_4$alkyl, —[C(R$^{X1a}$)$_2$]$_p$—CON—(C$_1$-C$_4$alkyl), —[C(R$^{X1a}$)$_2$]$_p$—NH$_2$, —[C(R$^{X1a}$)$_2$]$_p$—NH—C$_1$-C$_4$alkyl, —[C(R$^{X1a}$)$_2$]$_p$—N—(C$_1$-C$_4$alkyl)$_2$; wherein p is 0, 1, 2, or 3; wherein each $R^{X1a}$ is independently selected from the group consisting of hydrogen, deuterium, halo, —CF$_3$, and C$_1$-C$_4$alkyl, or both $R^{X1a}$ groups together form $C_3$-$C_6$cycloalkyl;

wherein each $R^{X2}$ is independently hydrogen or $C_1$-$C_4$alkyl;

each $R^Y$ is independently selected from the group consisting of hydrogen, deuterium, halo, and $C_1$-$C_4$alkyl, or both $R^Y$ groups together form $C_3$-$C_6$cycloalkyl or oxo; and m is 0, 1, or 2.

2. The compound of claim 1, wherein $Q^1$ is CH; $Q^2$ is N; $Q^3$ is C; $Q^4$ is C; and $Q^5$ is C.

3. The compound of claim 1, wherein $Q^1$ is N; $Q^2$ is C; $Q^3$ is N; $Q^4$ is C; and $Q^5$ is C.

4. The compound of claim 1, wherein $Q^1$ is CH; $Q^2$ is C; $Q^3$ is N; $Q^4$ is C; and $Q^5$ is C.

5. The compound of claim 1, wherein $Q^1$ is N; $Q^2$ is N; $Q^3$ is C; $Q^4$ is C; and $Q^5$ is C.

6. The compound of claim 1, wherein $Q^1$ is CH; $Q^2$ is N; $Q^3$ is C; $Q^4$ is N; and $Q^5$ is C.

7. The compound of claim 1, wherein $Q^1$ is CH; $Q^2$ is N; $Q^3$ is C; $Q^4$ is C; and $Q^5$ is N.

8. The compound of claim 1, wherein $R^1$ is hydrogen or halo.

9. The compound of claim 1, wherein $R^2$ is hydrogen or halo.

10. The compound of claim 1, wherein $R^2$ is selected from the group consisting of hydrogen, halo, $C_1$-$C_4$alkyl, —$CF_3$, —CN, —C≡CH, and —$NH_2$.

11. The compound of claim 1, wherein $R^3$ is hydrogen or halo.

12. The compound of claim 1, wherein Ar is

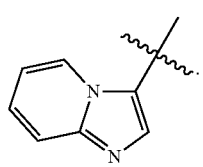 [SMILES: *c1cnc2ccccn12]

13. The compound of claim 1, wherein —Z—W—X—Y— is —C($R^Z$)$_2$—C($R^W$)$_2$—N($R^X$)—C($R^Y$)$_2$—.

14. The compound of claim 1, wherein —Z—W—X—Y— is —C($R^Z$)$_2$—C($R^W$)$_2$—CH($R^X$)—C($R^Y$)$_2$—.

15. The compound of claim 13, wherein each $R^Z$ is independently selected from the group consisting of hydrogen and halo.

16. The compound of claim 13, wherein both $R^Z$ groups together form $C_3$-$C_6$cycloalkyl.

17. The compound of claim 13, wherein both $R^Z$ groups together form oxo.

18. The compound of claim 1, wherein $R^Z$ and $R^W$ together with the carbons to which they are attached form a $C_3$-$C_6$cycloalkyl.

19. The compound of claim 1, wherein —Z—W—X—Y— is —C($R^W$)$_2$—CH($R^X$)—C($R^Y$)$_2$—.

20. The compound of claim 1, wherein each $R^W$ is independently selected from the group consisting of hydrogen and halo.

21. The compound of claim 1, wherein both $R^W$ groups together form $C_3$-$C_6$cycloalkyl.

22. The compound of claim 1, wherein both $R^W$ groups together form oxo.

23. The compound of claim 1, wherein each $R^Y$ is independently selected from the group consisting of hydrogen and halo.

24. The compound of claim 1, wherein both $R^Y$ groups together form $C_3$-$C_6$cycloalkyl.

25. The compound of claim 1, wherein both $R^Y$ groups together form oxo.

26. The compound of claim 1, wherein $R^X$ is $R^{X1}$, wherein $R^{X1}$ is heteroaryl.

27. The compound of claim 1, wherein $R^X$ is —CO$R^{X1}$.

28. The compound of claim 1, wherein $R^X$ is —SO$_2R^{X1}$.

29. The compound of claim 1, wherein $R^X$ is —($C_1$-$C_4$alkylene)-$R^{X1}$.

30. The compound of claim 27, wherein $R^{X1}$ is $C_3$-$C_8$cycloalkyl.

31. The compound of claim 27, wherein $R^{X1}$ is heterocyclic, wherein the heterocyclic is optionally substituted with one to twelve substituents that is halo.

32. The compound of claim 1, wherein $R^X$ is —CON($R^{X2}$)$_2$.

33. The compound of claim 32, wherein R' is hydrogen or methyl.

34. A compound selected from the group consisting of

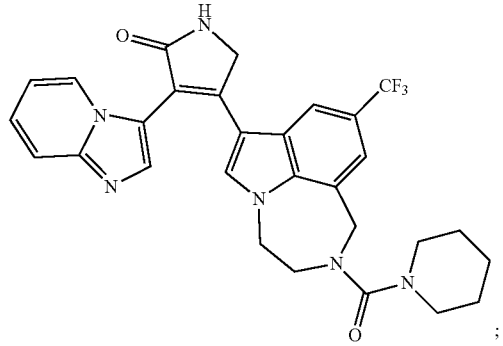

Compound I-1

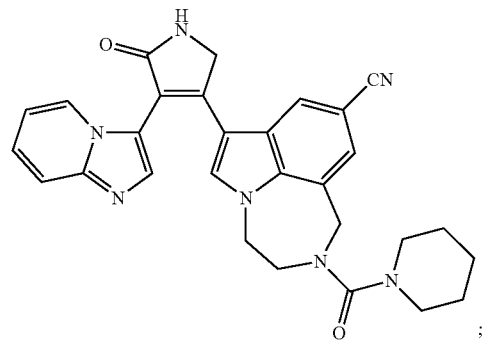

Compound I-2

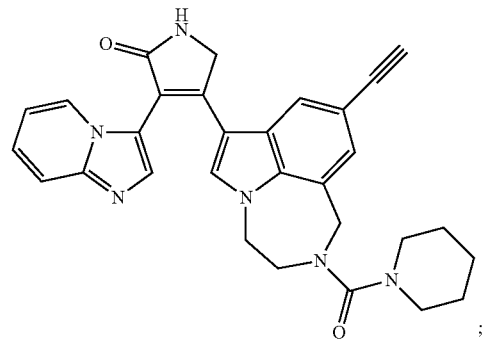

Compound I-3

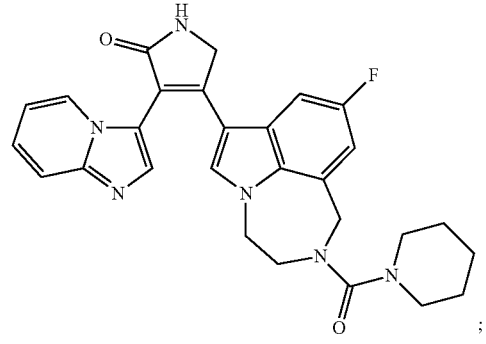

Compound I-4

-continued
Compound I-5
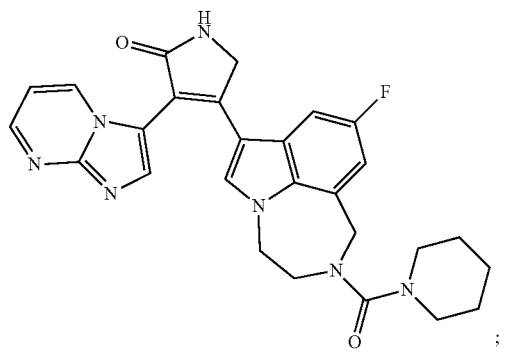
Compound I-6
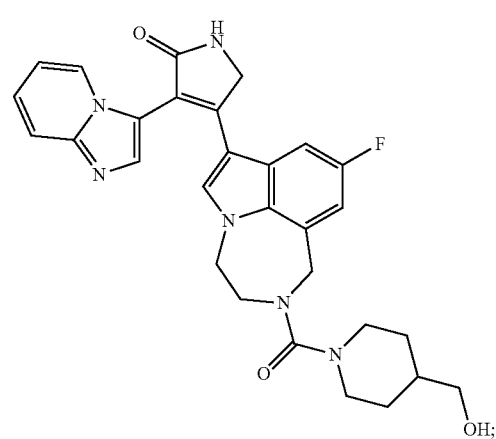
Compound I-7
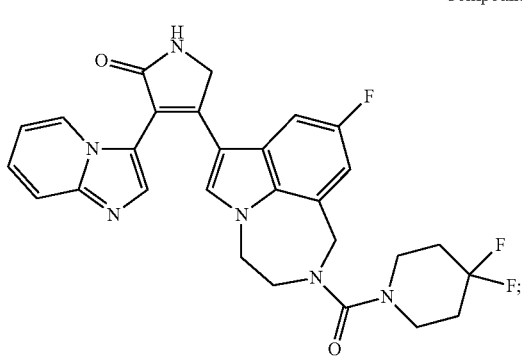
Compound I-8
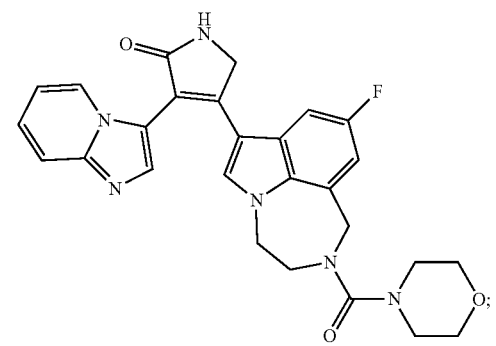
-continued
Compound I-9
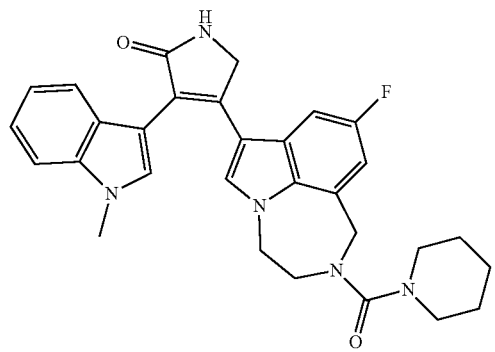
Compound I-10
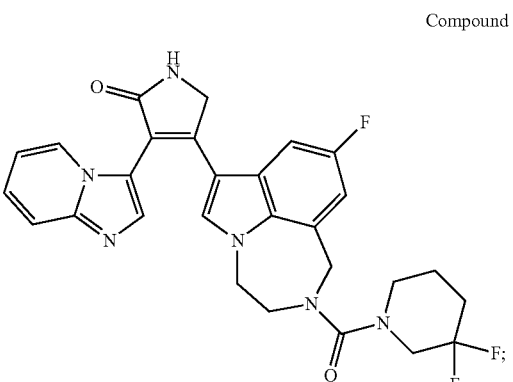
Compound I-11
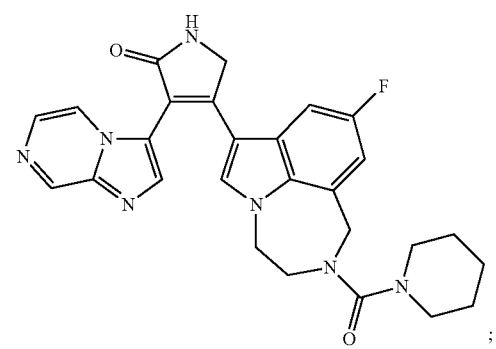
Compound I-12
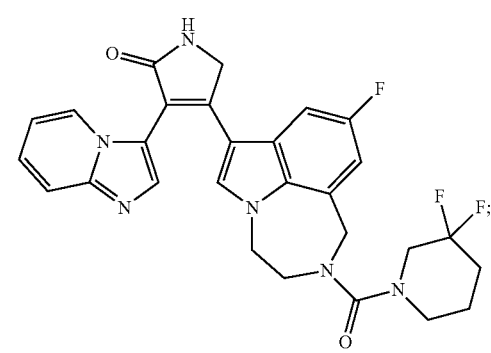

Compound I-13
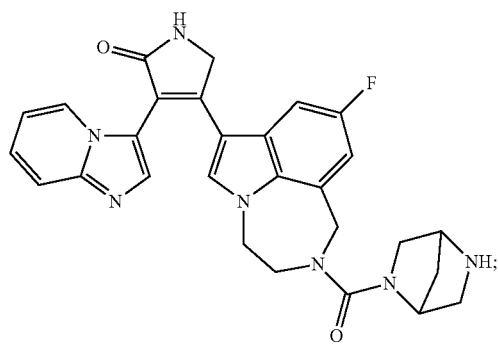
Compound I-17
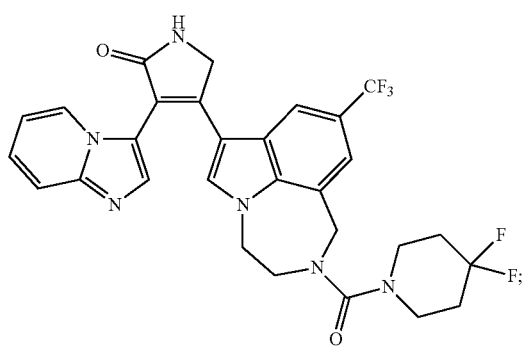
Compound I-14
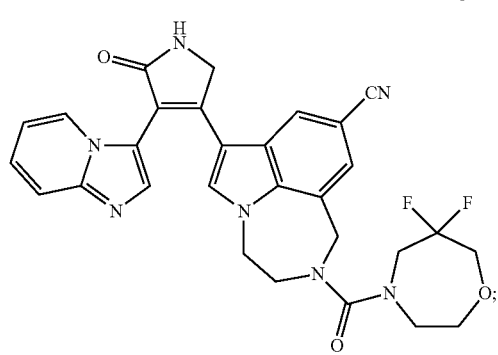
Compound I-18
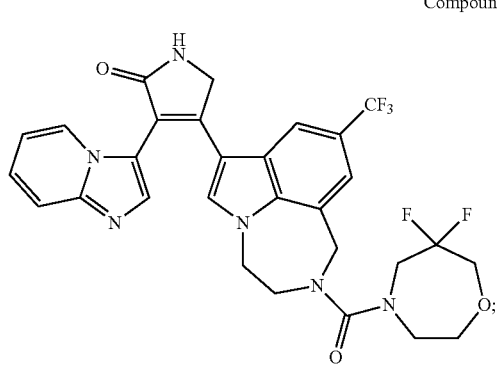
Compound I-15
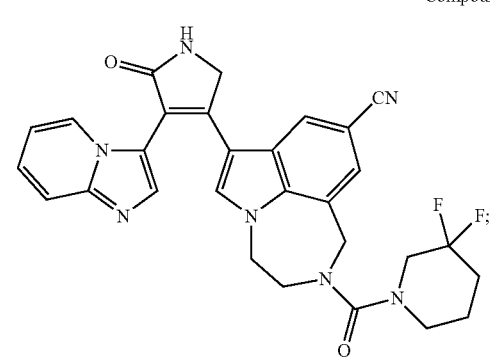
Compound I-19
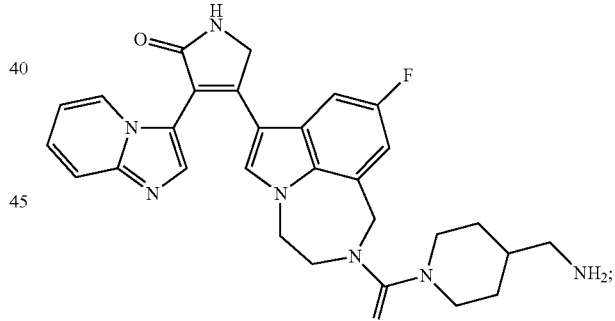
Compound I-16
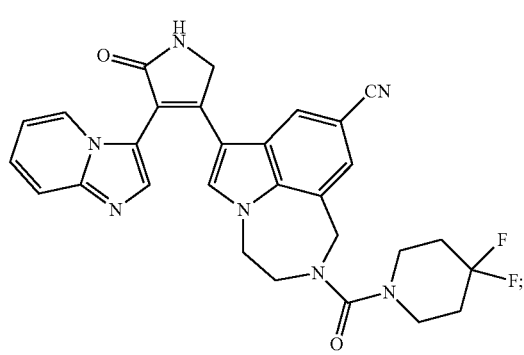
Compound I-20
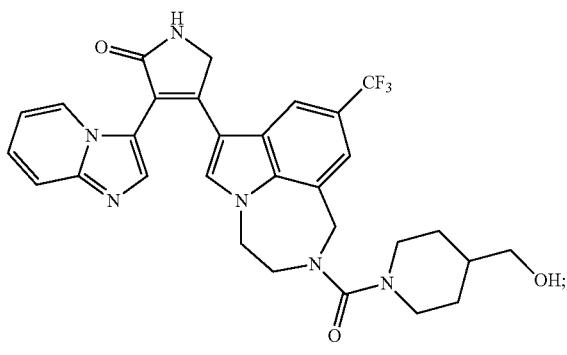

Compound I-21
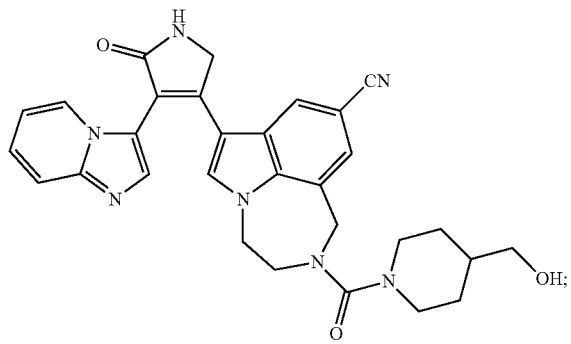
Compound I-25
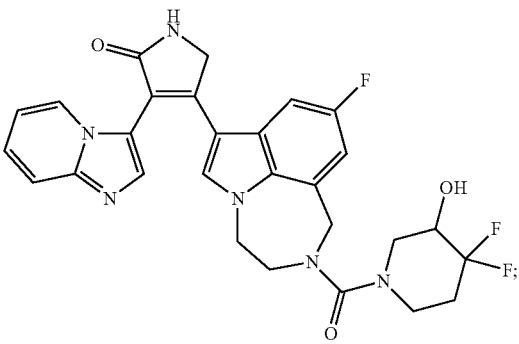
Compound I-22
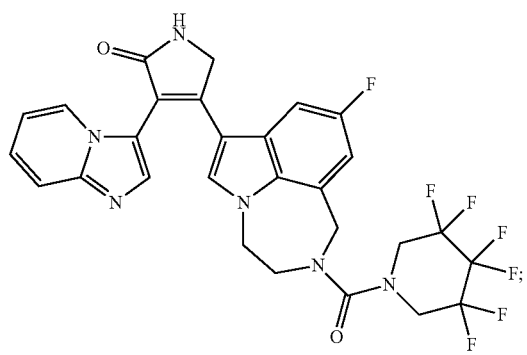
Compound I-26
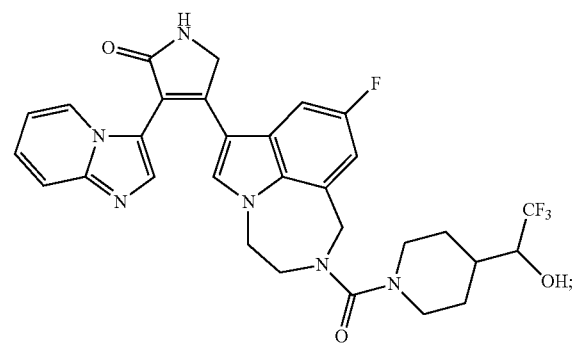
Compound I-23
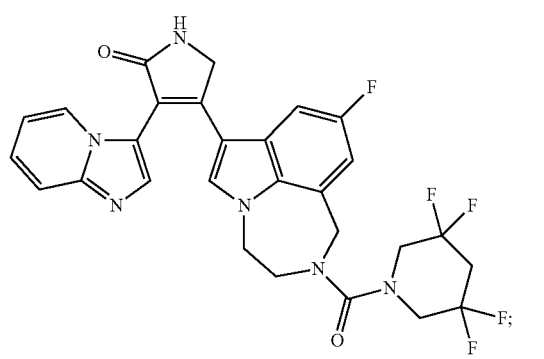
Compound I-27
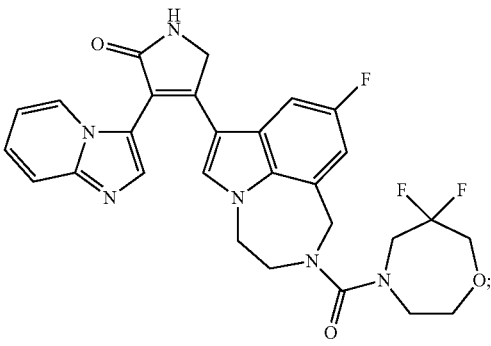
Compound I-24
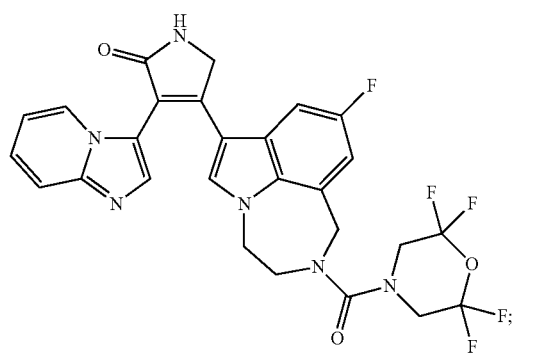
Compound I-28
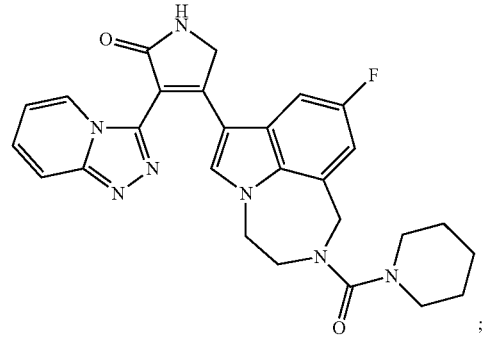

Compound I-29
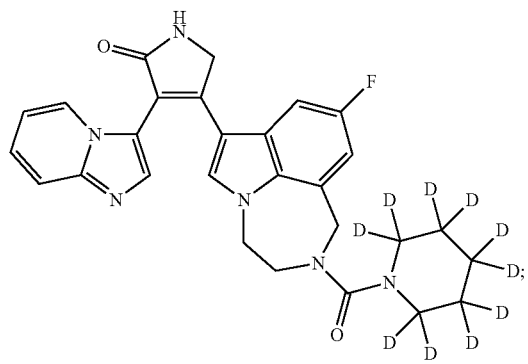
Compound I-33
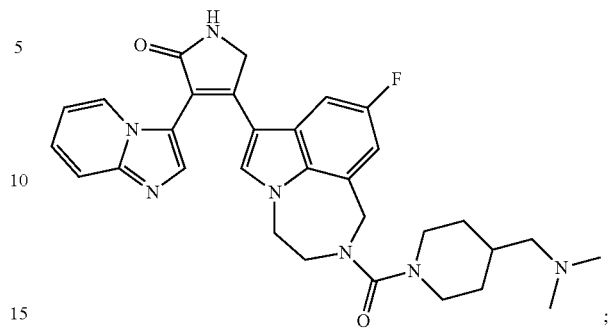
Compound I-30
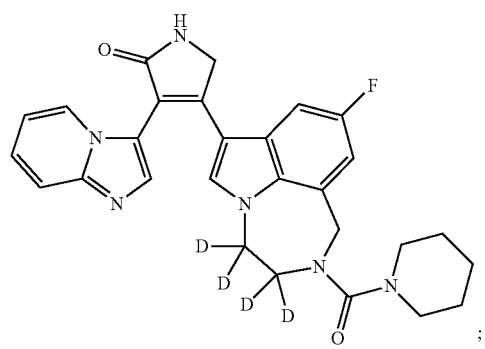
Compound I-34
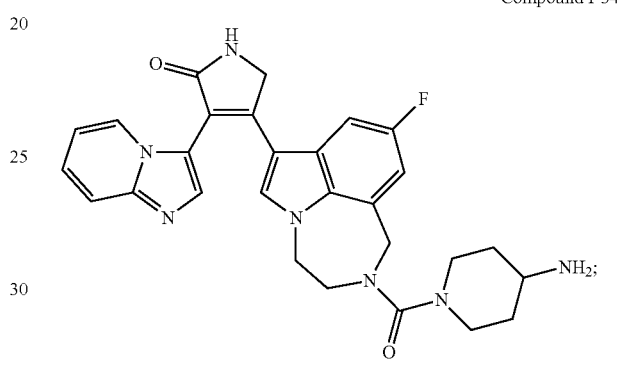
Compound I-31
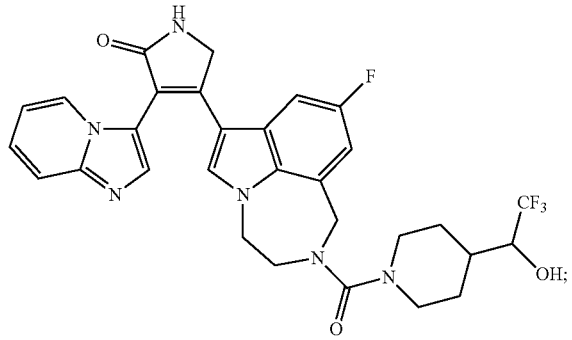
Compound I-35
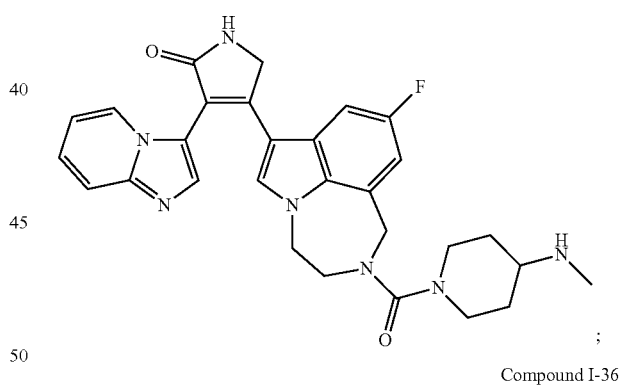
Compound I-32
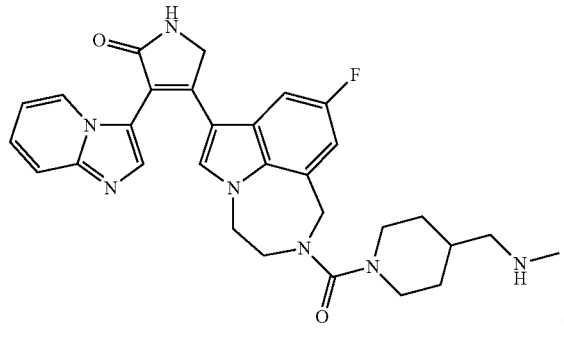
Compound I-36
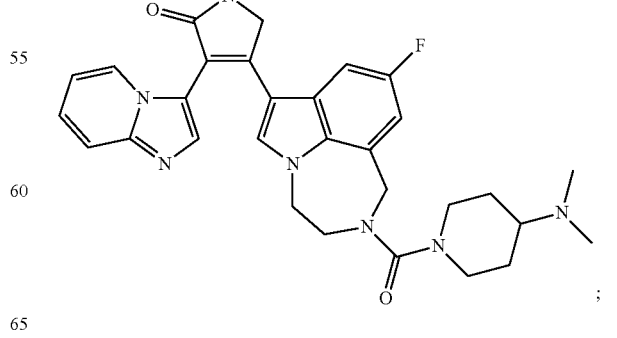

Compound I-37
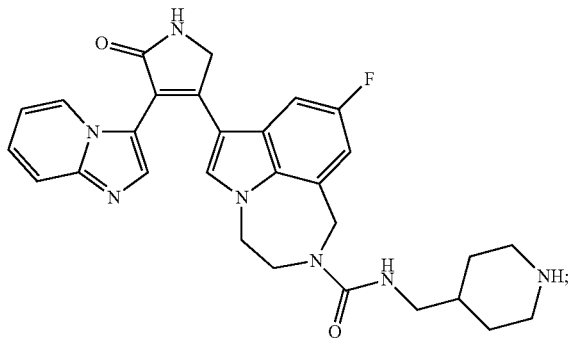
Compound I-41
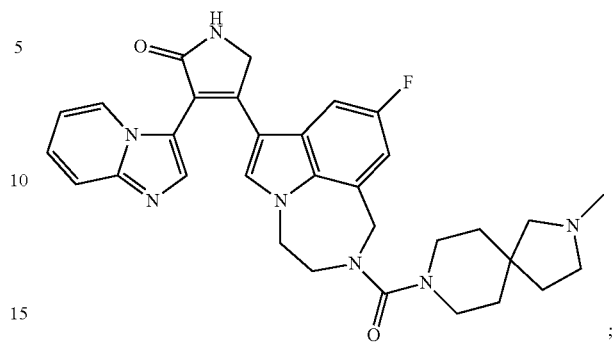
Compound I-38
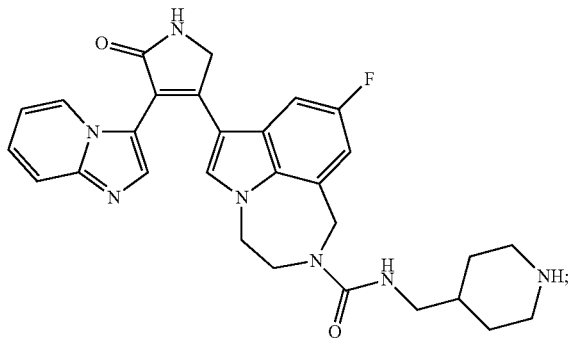
Compound I-42
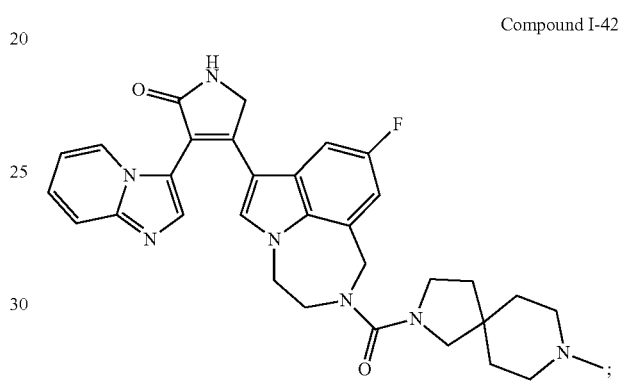
Compound I-39
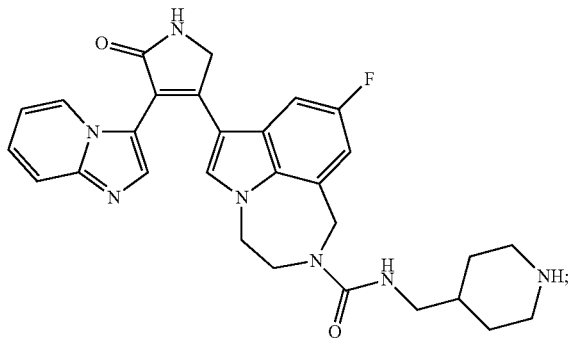
Compound I-43
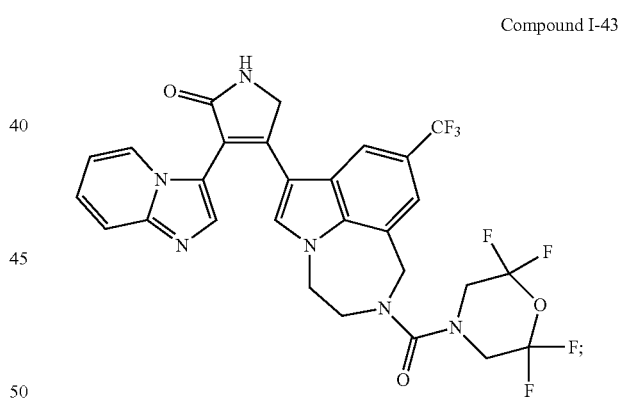
Compound I-40
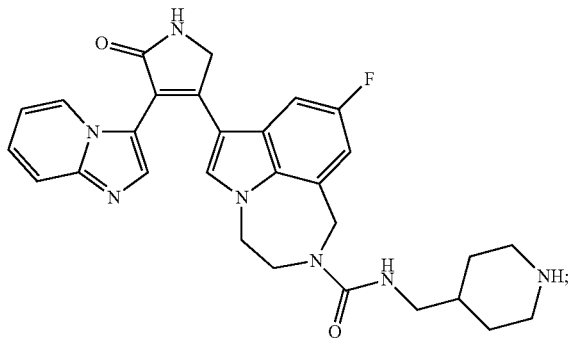
Compound I-44
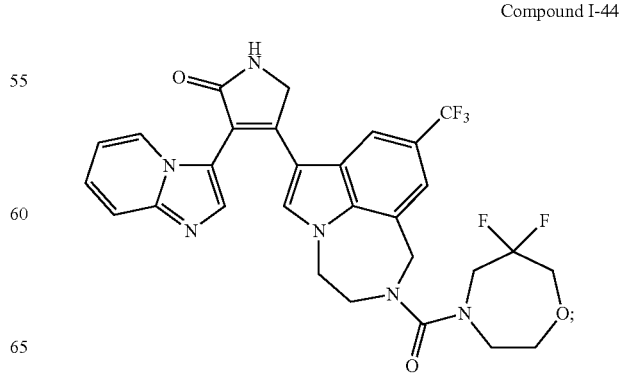

Compound I-45
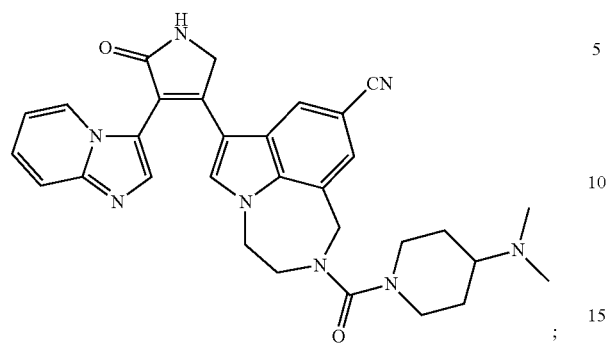
Compound I-49
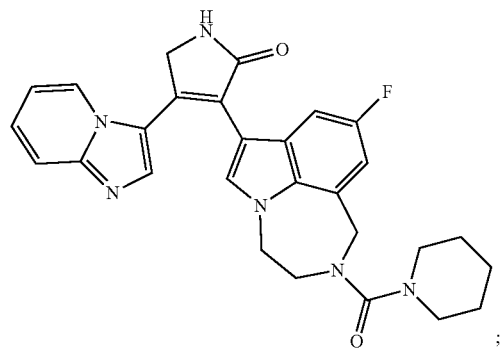
Compound I-46
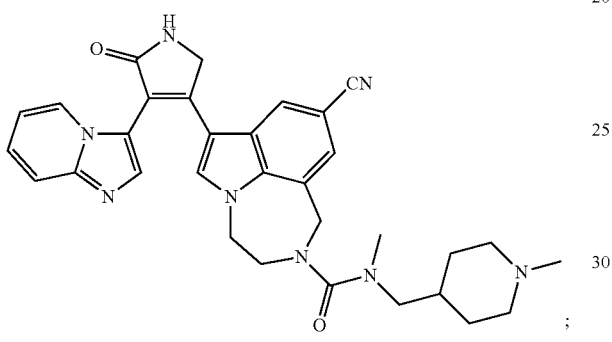
Compound I-50
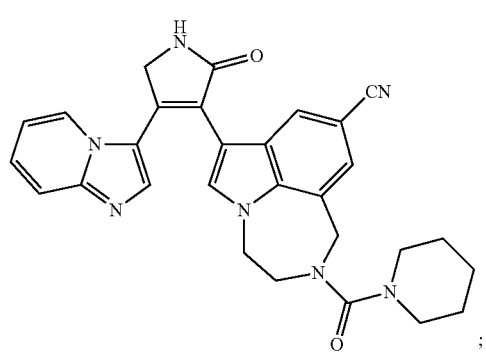
Compound I-47
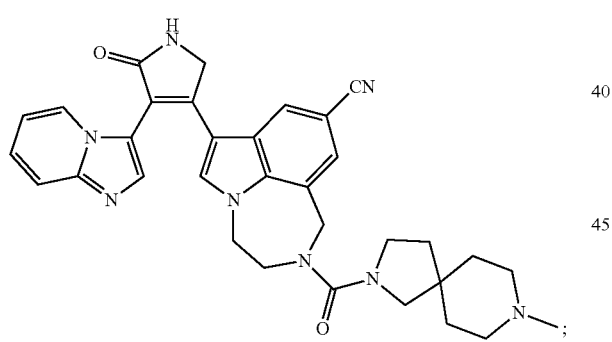
Compound I-51
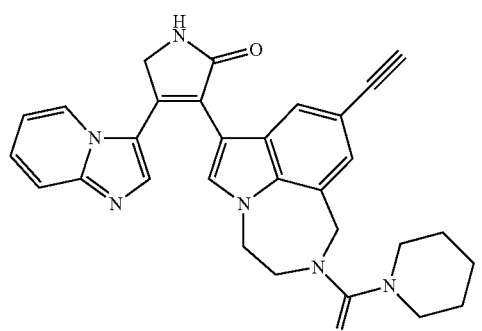
Compound I-48
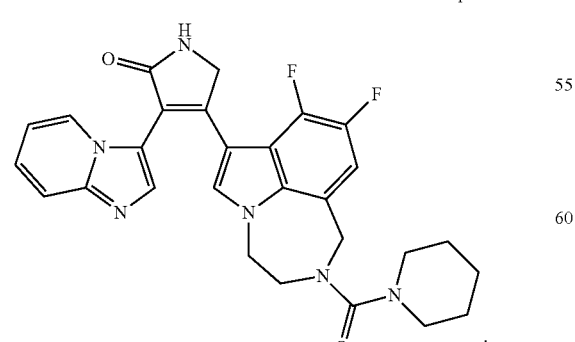
Compound I-52
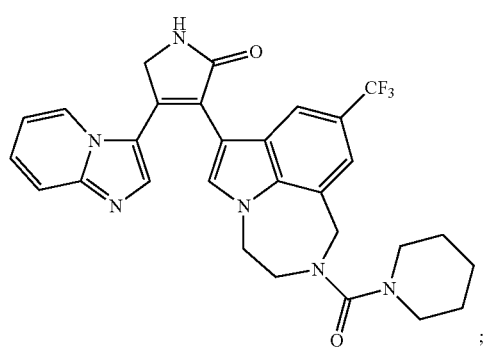

Compound I-53
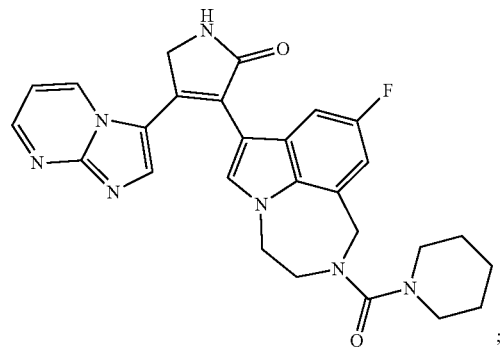
Compound I-54
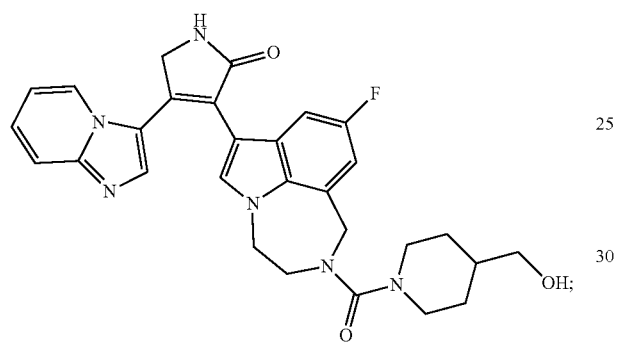
Compound I-55
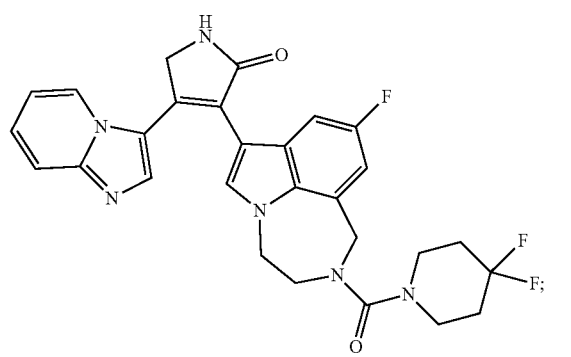
Compound I-56
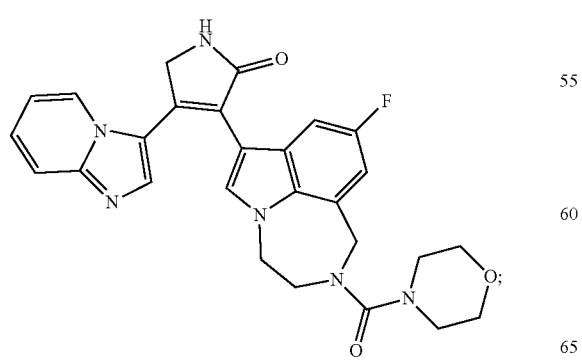
Compound I-57
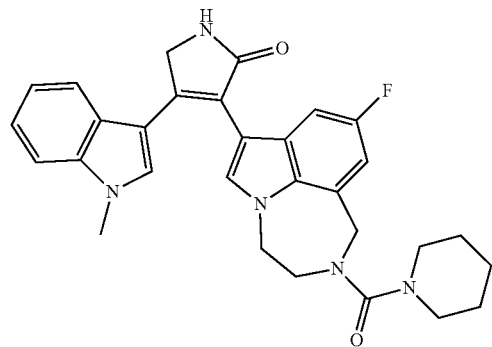
Compound I-58
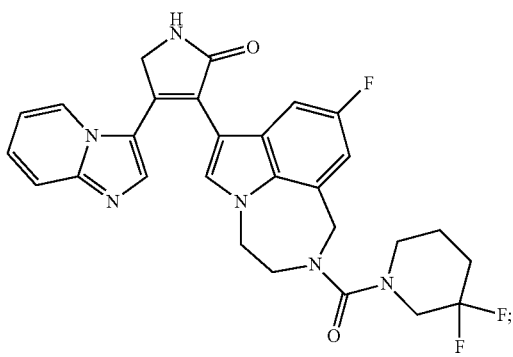
Compound I-59
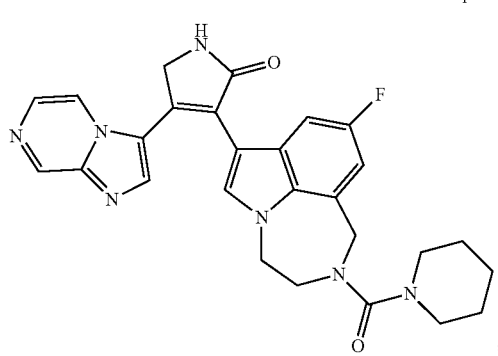
Compound I-60
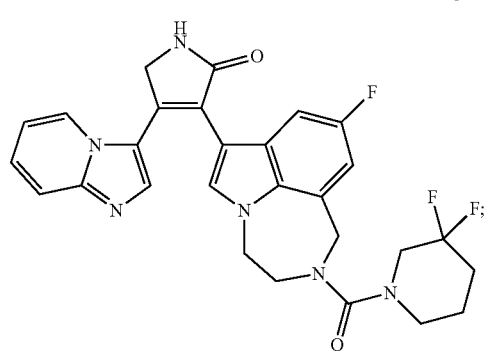

Compound I-61
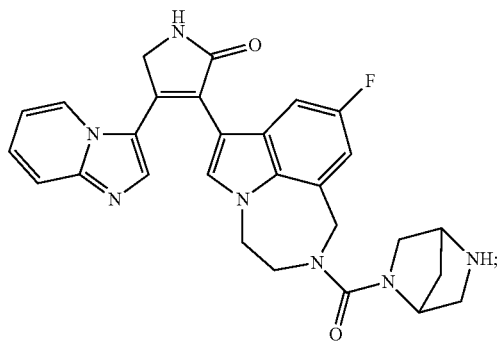
Compound I-65
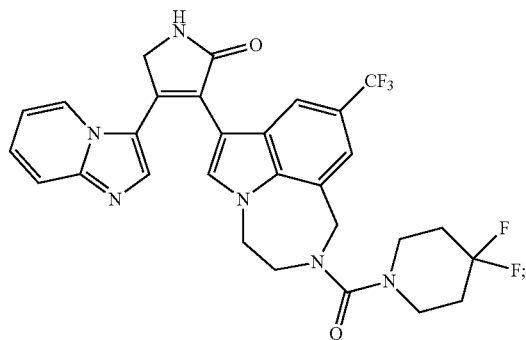
Compound I-62
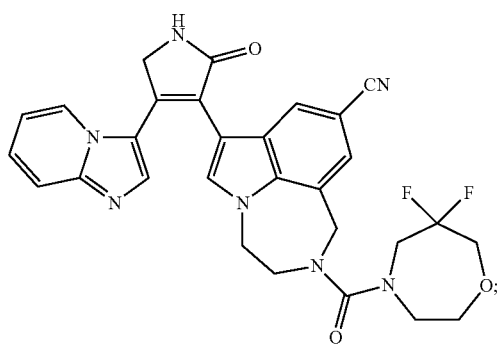
Compound I-66
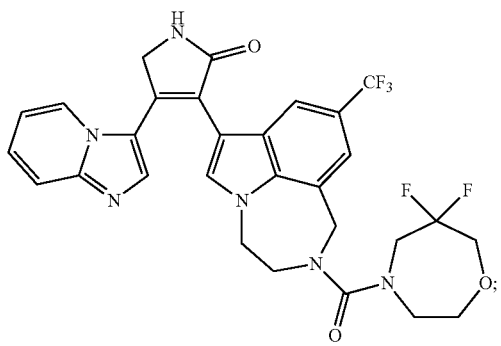
Compound I-63
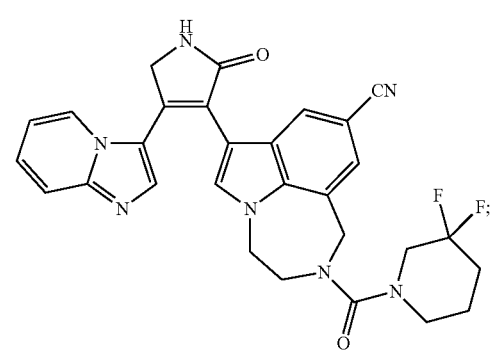
Compound I-67
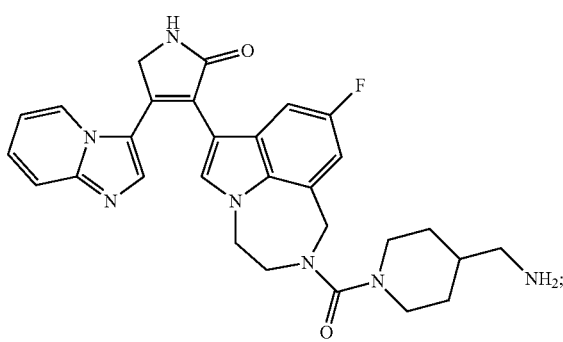
Compound I-64
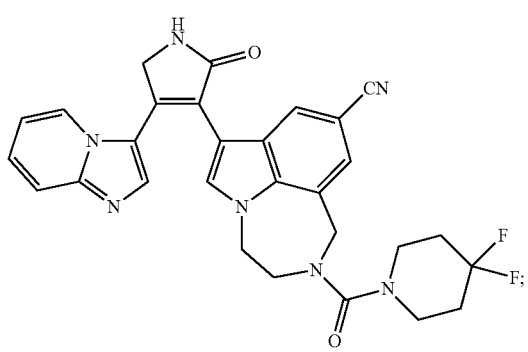
Compound I-68
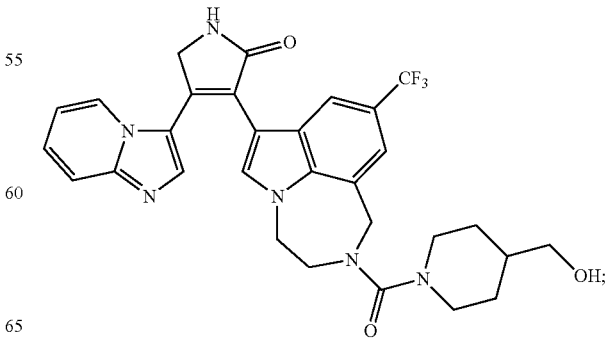

Compound I-69
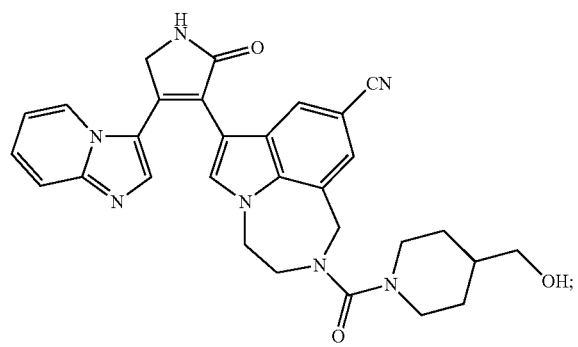
Compound I-73
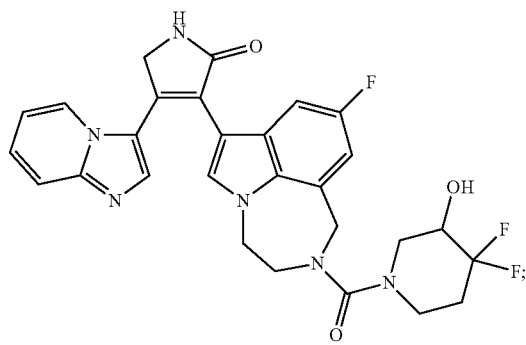
Compound I-70
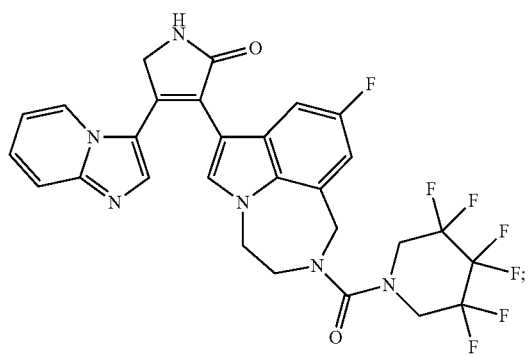
Compound I-74
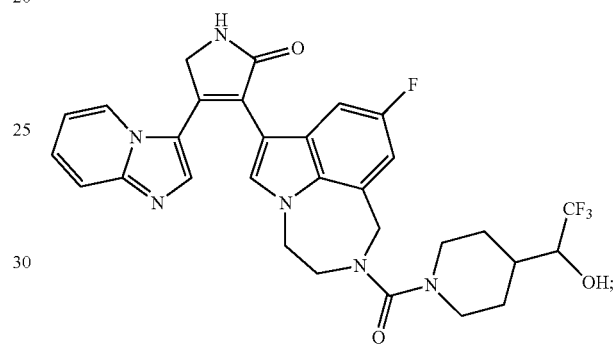
Compound I-71
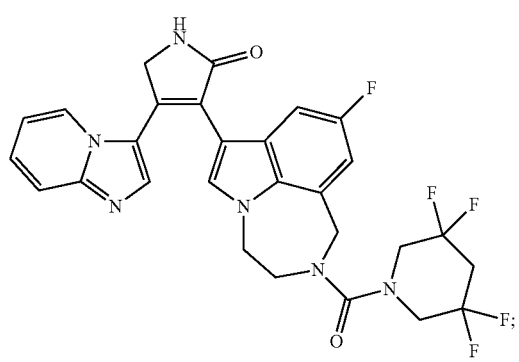
Compound I-75
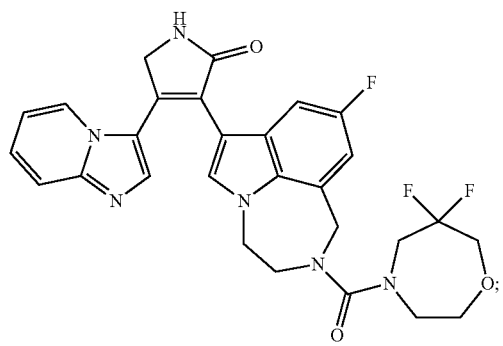
Compound I-72
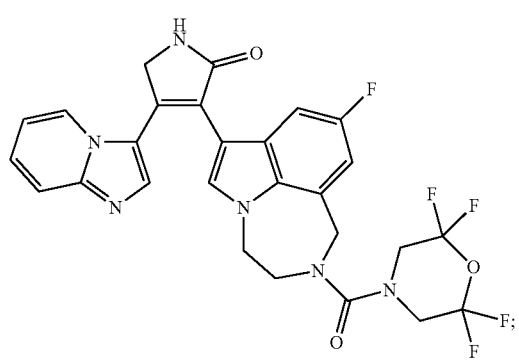
Compound I-76
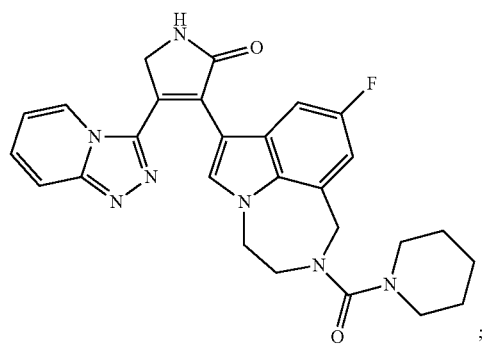

Compound I-77
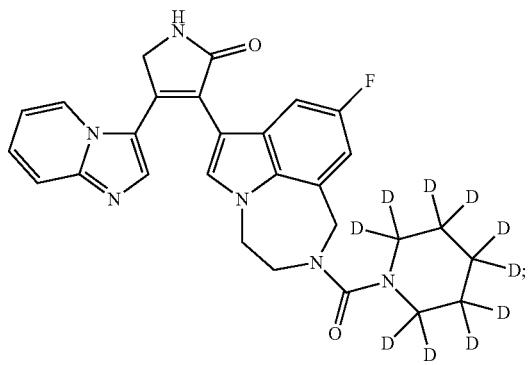
Compound I-81
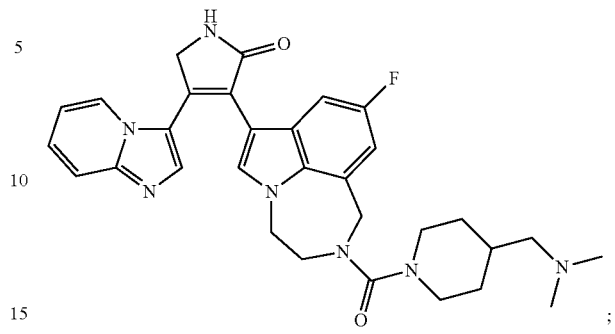
Compound I-78
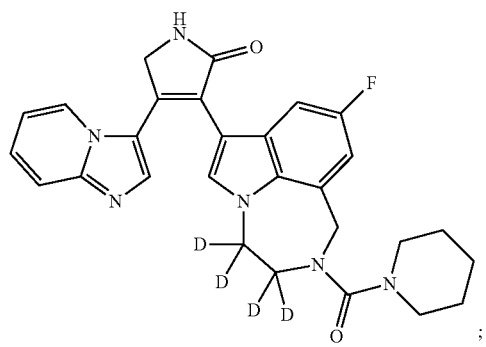
Compound I-82
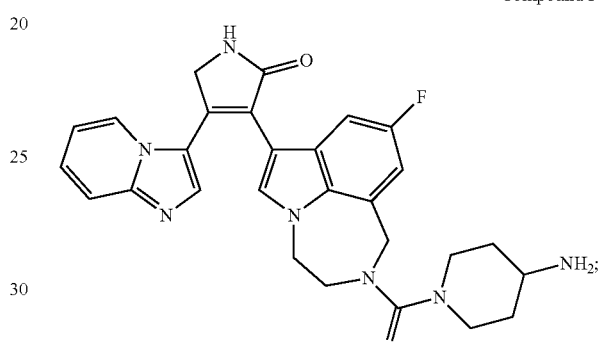
Compound I-79
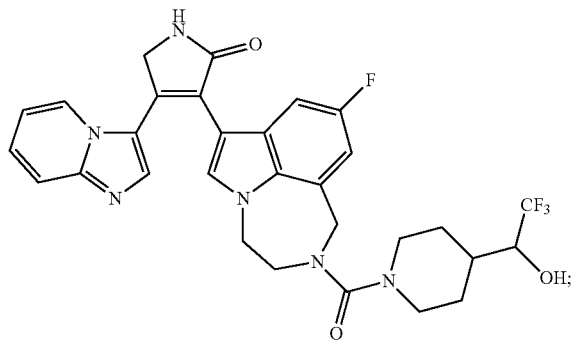
Compound I-83
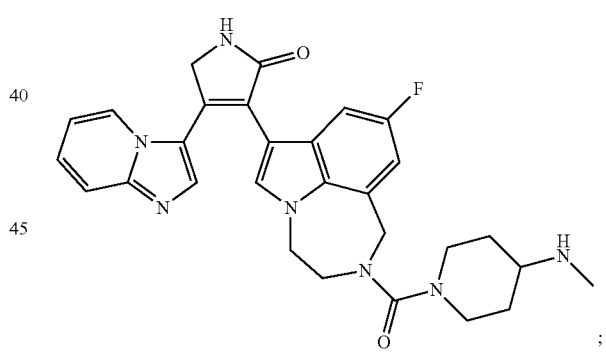
Compound I-80
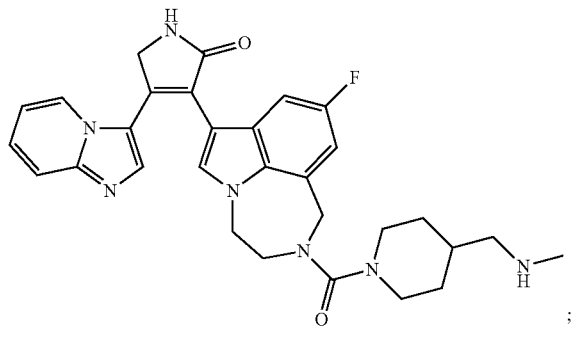
Compound I-84
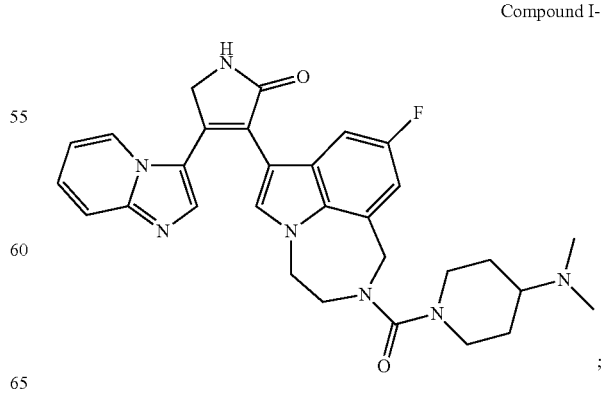

Compound I-85
Compound I-89
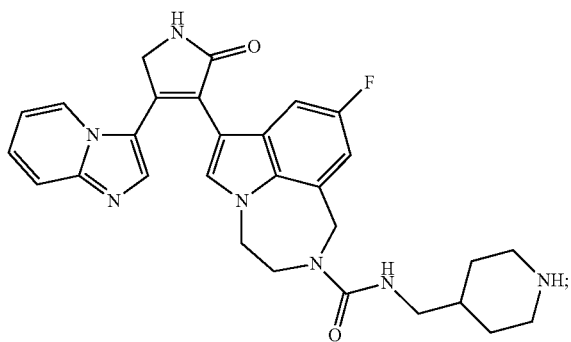
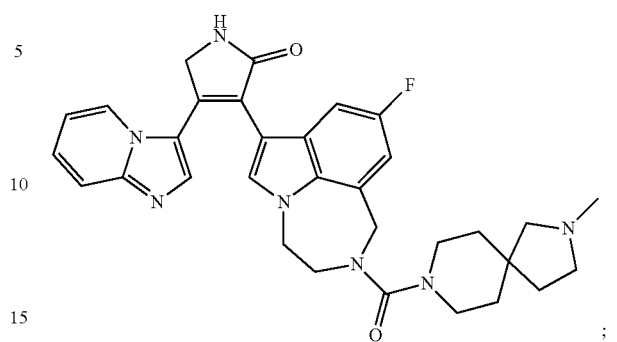
Compound I-86
Compound I-90
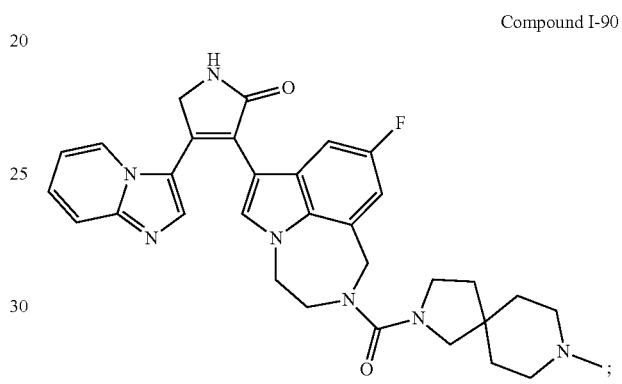
Compound I-87
Compound I-91
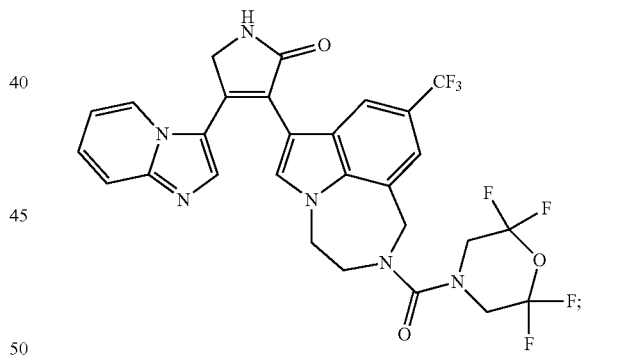
Compound I-88
Compound I-92
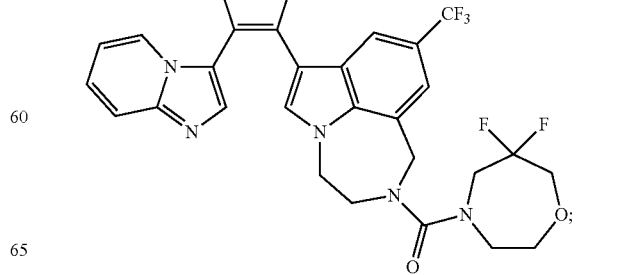

Compound I-93

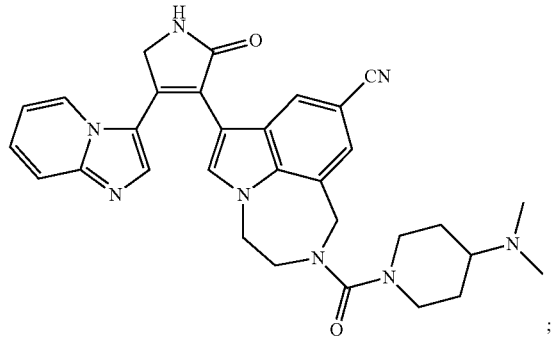

Compound I-94

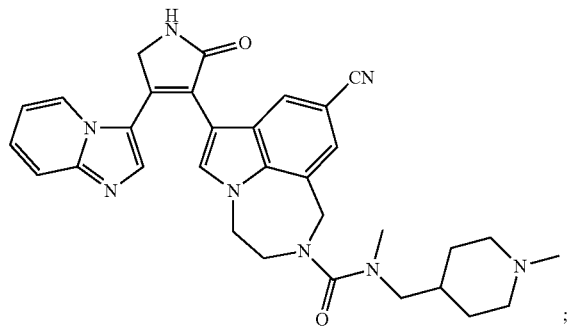

Compound I-95

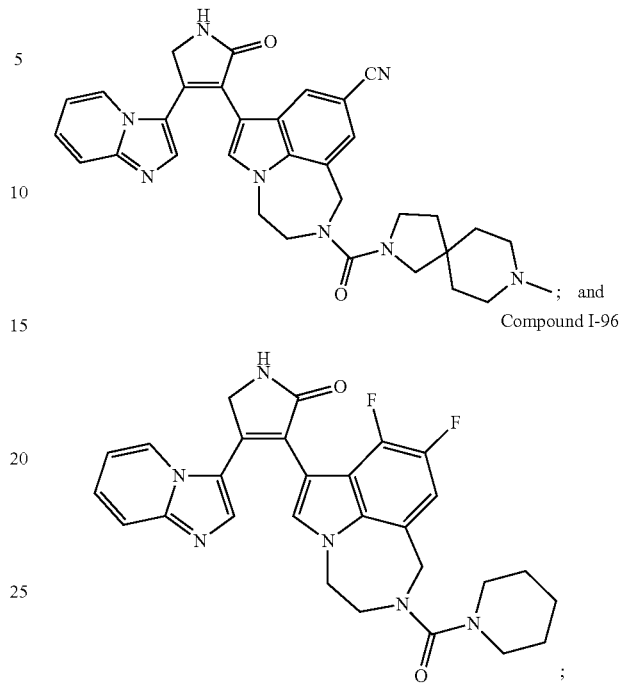

Compound I-96

; and and pharmaceutically acceptable salts and tautomers thereof.

35. A pharmaceutical composition comprising a compound of claim 1, or a pharmaceutically acceptable salt or tautomer thereof, and a pharmaceutically acceptable carrier.

36. The pharmaceutical composition of claim 35, further comprising HDAC inhibitor.

37. The pharmaceutical composition of claim 35, further comprising TGF beta inhibitor.

38. The pharmaceutical composition of claim 35, further comprising BMP inhibitor.

39. The pharmaceutical composition of claim 35, further comprising poloxamer.

* * * * *

UNITED STATES PATENT AND TRADEMARK OFFICE
CERTIFICATE OF CORRECTION

PATENT NO. : 10,383,881 B2
APPLICATION NO. : 15/852889
DATED : August 20, 2019
INVENTOR(S) : Christopher Loose et al.

It is certified that error appears in the above-identified patent and that said Letters Patent is hereby corrected as shown below:

In the Claims

At Column 123, Claim number 1, Line number 16:
"from the group consisting of halo and OH; and wherein"
Should read:
-- from the group consisting of halo and –OH; and wherein --

At Column 123, Claim number 1, Line number 25:
"wherein $R^{1a}$ is $C_1$-$C_4$alkyl; or $R^3$ is absent, if $Q^5$ is N;"
Should read:
-- wherein $R^{3a}$ is $C_1$-$C_4$alkyl; or $R^3$ is absent, if $Q^5$ is N; --

At Column 125, Claim number 33, Line number 66:
"33. The compound of claim 32, wherein $R^1$ is hydrogen or"
Should read:
-- 33. The compound of claim 32, wherein $R^{X2}$ is hydrogen or --

Signed and Sealed this
Eighth Day of October, 2019

Andrei Iancu
*Director of the United States Patent and Trademark Office*